United States Patent
MacMullin et al.

(10) Patent No.: US 10,948,471 B1
(45) Date of Patent: Mar. 16, 2021

(54) LEAK DETECTION EVENT AGGREGATION AND RANKING SYSTEMS AND METHODS

(71) Applicant: Picarro Inc., Santa Clara, CA (US)

(72) Inventors: Sean MacMullin, Santa Clara, CA (US); Chris W. Relia, Sunnyvale, CA (US); Aaron Van Pelt, Hayward, CA (US); Alex Balkanski, Woodside, CA (US); Yonggang He, Union City, CA (US); Sze Tan, Sunnyvale, CA (US); David Steele, San Francisco, CA (US); Tim Clark, Nottingham, PA (US)

(73) Assignee: Picarro, Inc., Santa Clara, CA (US)

( * ) Notice: Subject to any disclaimer, the term of this patent is extended or adjusted under 35 U.S.C. 154(b) by 331 days.

(21) Appl. No.: 15/996,069

(22) Filed: Jun. 1, 2018

Related U.S. Application Data

(60) Provisional application No. 62/513,957, filed on Jun. 1, 2017.

(51) Int. Cl.
*G01N 33/00* (2006.01)
*G01M 3/04* (2006.01)

(52) U.S. Cl.
CPC .......... *G01N 33/0075* (2013.01); *G01M 3/04* (2013.01); *G01N 33/0047* (2013.01)

(58) Field of Classification Search
CPC .. G01N 33/0075; G01N 33/0047; G01M 3/04
See application file for complete search history.

(56) References Cited

U.S. PATENT DOCUMENTS

| 4,690,689 A | 9/1987 | Malcosky et al. |
| 5,191,341 A | 3/1993 | Gouard et al. |

(Continued)

FOREIGN PATENT DOCUMENTS

| CA | 2339865 A1 | 7/2002 |
| JP | 61155932 A | 7/1986 |

(Continued)

OTHER PUBLICATIONS

Tan, U.S. Appl. No. 15/137,550, filed Apr. 25, 2016.
(Continued)

*Primary Examiner* — Bryan Bui
(74) *Attorney, Agent, or Firm* — Law Office of Andrei D Popovici, PC

(57) ABSTRACT

In some embodiments, data from multiple vehicle-based natural gas leak detection survey runs are used by computer-implemented machine learning systems to generate a list of natural gas leaks ranked by hazard level. A risk model embodies training data having known hazard levels, and is used to classify newly-discovered leaks. Hazard levels may be expressed by continuous variables, and/or probabilities that a given leak fits within a predefined category of hazard (e.g. Grades 1-3). Each leak is represented by a cluster of leak indications (peaks) originating from a common leak sources. Hazard-predictive features may include maximum, minimum, mean, and/or median CH4/amplitude of aggregated leak indications; estimated leak flow rate, determined from an average of leak indications in a cluster; likelihood of leak being natural gas based on other indicator data (e.g. ethane concentration); probability the leak was detected on a given pass; and estimated distance to leak source.

24 Claims, 27 Drawing Sheets

(56) References Cited

U.S. PATENT DOCUMENTS

| | | |
|---|---|---|
| 5,272,646 A | 12/1993 | Farmer |
| 5,297,421 A | 3/1994 | Hosonuma et al. |
| 5,390,530 A | 2/1995 | Hosonuma et al. |
| 5,832,411 A | 11/1998 | Schatzmann et al. |
| 5,946,095 A | 8/1999 | Henningsen et al. |
| 6,282,943 B1 | 9/2001 | Sanders et al. |
| 6,518,562 B1 | 2/2003 | Cooper et al. |
| 6,532,801 B1 | 3/2003 | Shan et al. |
| 6,664,533 B1 | 12/2003 | van der Laan et al. |
| 6,815,687 B1 | 11/2004 | Branch-Sullivan et al. |
| 6,822,742 B1 | 11/2004 | Kalayeh et al. |
| 6,995,846 B2 | 2/2006 | Kalayeh et al. |
| 7,075,653 B1 | 7/2006 | Rutheford |
| 7,260,507 B2 | 8/2007 | Kalayeh |
| 7,352,463 B2 | 4/2008 | Bounaix |
| 7,486,399 B1 | 2/2009 | Reichardt et al. |
| 7,588,726 B1* | 9/2009 | Mouradian .......... G01N 1/2205 422/83 |
| 7,602,277 B1 | 10/2009 | Daly et al. |
| 7,730,776 B2 | 6/2010 | Cornett et al. |
| 7,934,412 B2 | 5/2011 | Prince |
| 8,000,936 B2 | 8/2011 | Davis |
| 8,081,112 B2 | 12/2011 | Tucker et al. |
| 8,200,737 B2 | 6/2012 | Tarabzouni et al. |
| 9,322,735 B1 | 4/2016 | Tan et al. |
| 9,482,591 B2 | 11/2016 | Rella et al. |
| 9,500,556 B2 | 11/2016 | Rella et al. |
| 9,557,240 B1 | 1/2017 | Tan et al. |
| 9,599,529 B1 | 3/2017 | Steele et al. |
| 9,599,597 B1 | 3/2017 | Steele et al. |
| 9,618,417 B2 | 4/2017 | Rella et al. |
| 9,645,039 B1 | 5/2017 | Tan et al. |
| 9,719,879 B1 | 8/2017 | Tan et al. |
| 9,823,231 B1 | 11/2017 | Steele et al. |
| 10,330,555 B1 | 6/2019 | Tan et al. |
| 10,337,946 B1 | 7/2019 | Tan et al. |
| 10,466,132 B1* | 11/2019 | Tan .................... G06F 15/00 |
| 10,598,562 B2 | 3/2020 | Steele et al. |
| 2004/0012491 A1 | 1/2004 | Kulesz et al. |
| 2004/0263852 A1 | 12/2004 | Degtiarev et al. |
| 2005/0038825 A1 | 2/2005 | Tarabzouni et al. |
| 2006/0162428 A1 | 7/2006 | Hu et al. |
| 2006/0203248 A1 | 9/2006 | Reichardt et al. |
| 2008/0033693 A1 | 2/2008 | Andenna et al. |
| 2008/0052010 A1 | 2/2008 | Lee et al. |
| 2008/0092061 A1 | 4/2008 | Bankston et al. |
| 2008/0127726 A1 | 6/2008 | Elkins |
| 2008/0168826 A1 | 7/2008 | Saidi et al. |
| 2008/0225273 A1 | 9/2008 | Ershov et al. |
| 2010/0088031 A1 | 4/2010 | Nielsen et al. |
| 2010/0091267 A1 | 4/2010 | Wong |
| 2010/0094565 A1 | 4/2010 | Prince et al. |
| 2010/0268480 A1 | 10/2010 | Prince |
| 2011/0109464 A1 | 5/2011 | Lepley et al. |
| 2011/0119040 A1 | 5/2011 | McLennan |
| 2011/0161885 A1 | 6/2011 | Gonia et al. |
| 2011/0213554 A1* | 9/2011 | Archibald .............. G01V 9/007 702/6 |
| 2011/0249122 A1 | 10/2011 | Tricoukes et al. |
| 2011/0251800 A1 | 10/2011 | Wilkins |
| 2012/0019380 A1 | 1/2012 | Nielsen et al. |
| 2012/0050143 A1 | 3/2012 | Border et al. |
| 2012/0072189 A1 | 3/2012 | Bullen et al. |
| 2012/0092649 A1 | 4/2012 | Wong |
| 2012/0113285 A1 | 5/2012 | Baker et al. |
| 2012/0191349 A1 | 7/2012 | Lenz et al. |
| 2012/0194541 A1 | 8/2012 | Kim et al. |
| 2012/0194549 A1 | 8/2012 | Osterhout et al. |
| 2012/0204781 A1 | 8/2012 | Chun et al. |
| 2012/0232915 A1 | 9/2012 | Bromberger |
| 2013/0113939 A1 | 5/2013 | Strandemar |
| 2013/0179078 A1 | 7/2013 | Griffon |
| 2014/0026641 A1 | 1/2014 | Rella et al. |
| 2014/0032160 A1* | 1/2014 | Rella .................. G01N 21/3504 702/127 |
| 2016/0146696 A1 | 5/2016 | Steele et al. |
| 2016/0147583 A1 | 5/2016 | Simhon et al. |
| 2016/0210556 A1 | 7/2016 | Simhon et al. |

FOREIGN PATENT DOCUMENTS

| | | |
|---|---|---|
| JP | H07120344 | 5/1995 |
| JP | 2006118981 | 5/2006 |

OTHER PUBLICATIONS

Steele, U.S. Appl. No. 15/144,751, filed May 2, 2016.
Steele, U.S. Appl. No. 14/948,287, filed Nov. 21, 2015.
Tan, U.S. Appl. No. 15/418,367, filed Jan. 27, 2017.
Nottrott, U.S. Appl. No. 16/020,874, filed Jun. 27, 2018.
Steele, U.S. Appl. No. 15/462,533, filed Mar. 17, 2017.
USPTO, Office Action dated Sep. 28, 2017 for U.S. Appl. No. 15/462,533, filed Mar. 17, 2017.
USPTO, Office Action dated Jun. 4, 2018 for U.S. Appl. No. 15/418,367, filed Jan. 27, 2017.
USPTO, Office Action dated Sep. 22, 2016 for U.S. Appl. No. 13/733,861, filed Jan. 3, 2013.
USPTO, Office Action dated Aug. 25, 2016 for U.S. Appl. No. 13/733,864, filed Jan. 3, 2013.
USPTO, Office Action dated Aug. 28, 2015 for U.S. Appl. No. 13/733,857, filed Jan. 3, 2013.
USPTO, Office Action dated Nov. 5, 2015 for U.S. Appl. No. 13/733,864, filed Jan. 3, 2013.
USPTO, Office Action dated Nov. 20, 2015 for U.S. Appl. No. 13/733,861, filed Jan. 3, 2013.
USPTO, Office Action dated May 28, 2015 for U.S. Appl. No. 13/913,357, filed Jun. 7, 2013.
USPTO, Office Action dated May 28, 2015 for U.S. Appl. No. 13/913,359, filed Jun. 7, 2013.
USPTO, Office Action dated Jun. 26, 2015 for U.S. Appl. No. 13/733,868, filed Jan. 3, 2013.
USPTO, Office Action dated Apr. 20, 2016 for U.S. Appl. No. 13/733,857, filed Jan. 3, 2013.
USPTO, Office Action dated Mar. 10, 2016 for U.S. Appl. No. 13/913,357, filed Jun. 7, 2013.
USPTO, Office Action dated Mar. 9, 2016 for U.S. Appl. No. 13/913,359, filed Jun. 7, 2013.
USPTO, Office Action dated Jul. 1, 2016 for U.S. Appl. No. 14/139,388, filed Dec. 23, 2013.
USPTO, Office Action dated Jun. 28, 2016 for U.S. Appl. No. 14/139,348, filed Dec. 23, 2013.
USPTO, Office Action dated Mar. 8, 2017 for U.S. Appl. No. 14/319,236, filed Jun. 30, 2014.
USPTO, Office Action dated Nov. 16, 2017 for U.S. Appl. No. 15/418,367, filed Jan. 27, 2017.
USPTO, Office Action dated Jan. 2, 2018 for U.S. Appl. No. 15/137,550, filed Apr. 25, 2016.
EDF, "Boston: Snapshot of natural gas leaks", Environmental Defense Fund, https://web.archive.org/web/20141018170749/http://www.edf.org/climate/methanemaps/city-snapshots/boston, Boston, MA, Oct. 2014.
Gifford, Frank, "Statistical Properties of a Fluctuating Plume Dispersion Model," p. 117-137, U.S. Weather Bureau Office, Oak Ridge, Tennessee. 1959; the year of publication is sufficiently earlier than the effective U.S. filing date and any foreign priority date so that the particular month of publication is not in issue.
Turner, Bruce, "Workbook of Atmospheric Dispersion Estimates," p. 1-92. U.S. Environmental Protection Agency, Office of Air Programs. North Carolina, US, Jul. 1971.
EPA, "User's Guide for the Industrial Source Complex (ISC3) Dispersion Models, vol. II—Description of Model Algorithms." p. 1-128. U.S. Environmental Protection Agency. North Carolina, US, Sep. 1995.
Wainner et al., High Altitude Natural Gas Leak Detection System, DOE Program Final Report, DOE National Energy Technology Laboratory, Pittsburgh, PA, Apr. 2007.

(56) References Cited

OTHER PUBLICATIONS

Keats, Andrew, "Bayesian inference for source determination in the atmospheric environment," University of Waterloo, Waterloo, Ontario, Canada, 2009; the year of the publication is sufficiently earlier than the effective U.S. filing date and any foreign priority date so that the particular month of publication is not in issue.

Prasad Kuldeep R., "Quantification of Methane Emissions From Street Level Data,", http://www.nist.gov/manuscript-publication-search.cfm?pub_id=914433, Abstract #A53E-0213, American Geophysical Union (AGU), Fall Meeting, San Francisco, CA, Dec. 9-13, 2013.

Arata C. et al., "Fugitive Methane Source Detection and Discrimination with the Picarro Mobile Methane Investigator," http://adsabs.harvard.edu/abs/2013AGUFM.A53A0150A, Abstract #A53A-0150, American Geophysical Union (AGU), Fall Meeting, San Francisco, CA, Dec. 9-13, 2013.

Keats, Andrew et al., "Bayesian inference for source determination with applications to a complex urban environment," http://www.sciencedirect.com/science/article/pii/S1352231006008703, Atmospheric Environment 41.3, pp. 465-479, The Netherlands, Jan. 2007.

Pavlin G. et al., "Gas Detection and Source Localization: A Bayesian Approach," http://isif.org/fusion/proceedings/Fusion_2011/data/papers/054.pdf, 14th International Conference on Information Fusion, Chicago, Illinois, US, Jul. 2011.

Crosson E. et al., "Quantification of Methane Source Locations and Emissions in AN Urban Setting," http://www.slideserve.com/marly/quantification-of-methane-source-locations-and-emissions-in-an-urban-setting, uploaded on Jul. 31, 2014.

Cosson E. et al., "Quantification of Methane Source Locations and Emissions in AN Urban Setting," http://adsabs.harvard.edu/abs/2011AGUFM.B51Q..04C, American Geophysical Union (AGU), Fall Meeting, San Francisco, CA, Dec. 5-9, 2011.

Gas Trak Ltd., "Specializing in: Leak Detection Services for: Natural Gas Pipelines," http://www.slideserve.com/yama/specializing-in-leak-detection-services-for-natural-gas-pipelines, uploaded on Jul. 28, 2013.

Monster et al., "Measurements of Methane Emissions from Landfills Using Mobile Plume Method with Trace Gas and Cavity Ring-down Spectroscopy.", Geophysical Research Abstracts, EGU General Assembly, Vienna, Austria, Apr. 2012; listed in PTO-892 as Jan. 2012.

Carlbom et al., "Planar Geometric Projections and Viewing Transformations," Computing Surveys, vol. 10: 4, p. 465-502, ACM, New York, NY, Dec. 1978.

Lenz et al., "Flight Testing of an Advanced Airborne Natural Gas Leak Detection System," Final Report, ITT Industries Space Systems LLC, Rochester, NY, Oct. 2005.

Eorpean Patent Office (ISA), International Search Report and Written Opinion for International Application No. PCT/US2015/062038, dated Mar. 4, 2016, international filing date Nov. 21, 2015, priority date Nov. 21, 2014.

EDF, "Methodology: How the data was collected", Environmental Defense Fund, http://web.archive.org/web/20141019130933/http://www.edf.org/climate/methanemaps/methodology, New York, NY, Oct. 2014.

Redding, Steve, "Road Map to . . . Redefining the Leak Management Process", https://www3.epa.gov/gasstar/documents/workshops/2014_AIW/Advances_Leak_Detection.pdf, May 2014.

USPTO, Office Action dated Jun. 4, 2018 for U.S. Appl. No. 15/462,533, filed Mar. 17, 2017.

USPTO, Office Action dated Jul. 31, 2018 for U.S. Appl. No. 15/137,550, filed Apr. 25, 2016.

USPTO, Office Action dated Dec. 12, 2016 for U.S. Appl. No. 13/913,357, filed Jun. 7, 2013.

USPTO, Office Action dated Jun. 16, 2017 for U.S. Appl. No. 13/913,359, filed Jun. 7, 2013.

USPTO, Office Action dated Oct. 11, 2018 for U.S. Appl. No. 15/144,751, filed May 2, 2016.

De Nevers, Noel, "Air Pollution Control Engineering," p. 135-137, Waveland Press, Inc., Long Grove, IL., US, 2010; the year of publication is sufficiently earlier than the effective U.S. filing date and any foreign priority date so that the particular month of publication is not in issue.

Atherton et al., "Mobile measurement of methane emissions from natural gas developments in northeastern British Columbia, Canada,", Copernicus Publications on behalf of the European Geosciences Union, Munich, Germany, Oct. 19, 2017.

Humphries et al., "Atmospheric Tomography: A Bayesian Inversion Technique for Determining the Rate and Location of Fugitive Emissions," Environmental Science and Technology, 46, 3, pp. 1739-1746, Berkeley, CA, US, Dec. 12, 2011.

Rao, Shankar K., "Source estimation methods for atmospheric dispersion," Atmospheric Environment, vol. 41, Issue 33, pp. 6964-6973, Elsevier Ltd., Netherlands, Oct. 2007.

Yee et al., "Bayesian inversion of concentration data: Source reconstruction in the adjoint representation of atmospheric diffusion," 4th International Symposium on Computational Wind Engineering, Journal of Wind Engineering and Industrial Aerodynamics, vol. 96, Issues 10-11, pp. 1805-1816, Elsevier Ltd., Netherlands, Oct. 2008.

Von Fischer et al., "Rapid, Vehicle-Based Identification of Location and Magnitude of Urban Natural Gas Pipeline Leaks," Environmental Science and Technology, vol. 51, No. 7, pp. 4091-4099, Berkeley, CA, US, Mar. 22, 2017.

Schall et al., "Handheld Augmented Reality for underground infrastructure visualization," Personal and Ubiquitous Computing, V. 13, London, UK, May 2009.

USPTO, Offfice Action dated Feb. 26, 2019 for U.S. Appl. No. 14/948,287, filed Nov. 21, 2015.

mathisfun.com, "Definition of Tangent", https://mathisfun.com/definitions/tangent-line-.html, 2007; the year of publication is sufficiently earlier than the effective U.S. filing date and any foreign priority date so that the particular month of the publication is not in issue.

USPTO, Office Action dated Jun. 24, 2020 for U.S. Appl. No. 16/020,874, filed Jun. 27, 2018.

Tan, U.S. Appl. No. 16/450,970, filed Jun. 24, 2019.

Steele, U.S. Appl. No. 16/826,265, filed Mar. 22, 2020.

USPTO, Office Action dated Aug. 12, 2019 for U.S. Appl. No. 16/450,970, filed Jun. 24, 2019.

USPTO, Office Action dated Jan. 7, 2020 for U.S. Appl. No. 16/450,970, filed Jun. 24, 2019.

USPTO, Office Action dated Aug. 28, 2019 for U.S. Appl. No. 14/948,287, filed Nov. 21, 2015.

USPTO, Office Action dated Apr. 17, 2020 for U.S. Appl. No. 16/826,265, filed Mar. 22, 2020.

\* cited by examiner

| Surface wind speed at 10 m (m/s) | Day | | | Night | |
|---|---|---|---|---|---|
| | Incoming Solar radiation | | | Cloud Cover | |
| | Strong | Moderate | Slight | Thinly Overcast (>1/2 cloudy) | Mostly Cloudy |
| <2 | A | A-B | B | | |
| 2-3 | A-B | B | C | E | F |
| 3-5 | B | B-C | C | D | E |
| 5-6 | C | C-D | D | D | D |
| >6 | C | D | D | D | D |

FIG. 18

| u | 1/u | $\Delta\sigma/\Delta v$ | $ac = u\,\Delta\sigma/\Delta v$ |
|---|---|---|---|
| 0.5 | 2 | 4/3 | 2/3 |
| 1.0 | 1 | 2/3 | 2/3 |
| 2.0 | 0.5 | 1/3 | 2/3 |

LEAK DETECTION EVENT AGGREGATION AND RANKING SYSTEMS AND METHODS

RELATED APPLICATION DATA

This application claims the benefit of the filing date of U.S. Provisional Patent Application No. 62/513,957, filed Jun. 1, 2017, entitled "Leak Detection Aggregation and Ranking Systems and Methods," which is herein incorporated by reference.

BACKGROUND

The invention relates to systems and methods for detecting gas leaks such as methane leaks.

A common means of distributing energy around the world is by the transmission of gas, usually natural gas. In some areas of the world manufactured gasses are also transmitted for use in homes and factories. Gas is typically transmitted through underground pipelines having branches that extend into homes and other buildings for use in providing energy for space and water heating. Many thousands of miles of gas pipeline exist in virtually every major populated area. Since gas is highly combustible, gas leakage is a serious safety concern. Recently, there have been reports of serious fires or explosions caused by leakage of gas in the United States as the pipeline infrastructure becomes older. For this reason, much effort has been made to provide instrumentation for detecting small amounts of gas so that leaks can be located to permit repairs.

Conventionally, search teams are equipped with gas detectors to locate a gas leak in the immediate proximity of the detector. When the plume of gas from a leak is detected, the engineers may walk to scan the area slowly and in all directions by trial and error to find the source of the gas leak. This process may be further complicated by wind that quickly disperses the gas plume. Such a search method is time consuming and often unreliable, because the engineer walks around with little or no guidance while trying to find the source of the gas leak.

Another approach to gas leak detection is to mount a gas leak detection instrument on a moving vehicle, e.g., as considered in U.S. Pat. No. 5,946,095. A natural gas detector apparatus is mounted to the vehicle so that the vehicle transports the detector apparatus over an area of interest at speeds of up to 20 miles per hour. The apparatus is arranged such that natural gas intercepts a beam path and absorbs representative wavelengths of a light beam. A receiver section receives a portion of the light beam onto an electro-optical etalon for detecting the gas. Although a moving vehicle may cover more ground than a surveyor on foot, there is still the problem of locating the gas leak source (e.g., a broken pipe) if a plume of gas is detected from the vehicle. Thus, there is still a need to provide a method and apparatus to locate the source of a gas leak quickly and reliably.

SUMMARY

According to one aspect, a system comprises: a vehicle-borne gas concentration measurement device configured to perform a sequence of geospatially-referenced mobile gas concentration measurements along one or more survey paths to collect data including gas concentration and location; and at least one hardware processor coupled to the gas concentration measurement device and configured to: automatically analyze the collected data to identify a plurality of natural gas leaks, each leak corresponding to a cluster of leak identifications in the collected data; and generate a list of leaks sorted by hazard level by applying a risk model to the collected data.

According to another aspect, a method comprises: employing a vehicle-borne gas concentration measurement device to perform a sequence of geospatially-referenced mobile gas concentration measurements along one or more survey paths to collect data including gas concentration and location; and employing at least one hardware processor coupled to the gas concentration measurement device to: automatically analyze the collected data to identify a plurality of natural gas leaks, each leak corresponding to a cluster of leak identifications in the collected data; and generate a list of leaks sorted by hazard level by applying a risk model to the collected data.

According to another aspect, a non-transitory computer-readable medium encodes instructions which, when executed by a computer system, cause the computer system to: receive data collected by a vehicle-borne gas concentration measurement device performing a sequence of geospatially-referenced mobile gas concentration measurements along one or more survey paths, the collected data including gas concentration and location; and employ at least one hardware processor coupled to the gas concentration measurement device to: automatically analyze the collected data to identify a plurality of natural gas leaks, each leak corresponding to a cluster of leak identifications in the collected data; and generate a list of leaks sorted by hazard level by applying a risk model to the collected data.

According to another aspect, a method comprises: collecting a set of training data for training a risk model configured to rank natural gas leaks by hazard level, the training data including a hazard level value and values of a set of hazard-predictive features for each of a plurality of natural gas leaks, the values of the set of hazard-predictive features being determined according to data collected by a vehicle-borne gas concentration measurement device performing a sequence of geospatially-referenced mobile gas concentration measurements along one or more survey paths, the collected data including gas concentration and location; and configuring a set of parameters of the risk model according to the training data to generate predicted hazard level values for the plurality of natural gas leaks that match hazard level values in the training data.

According to another aspect, a non-transitory computer-readable medium encodes instructions which, when executed by a computer system comprising a hardware processor and an associated memory, cause the computer system to: collect a set of training data for training a risk model configured to rank natural gas leaks by hazard level, the training data including a hazard level value and values of a set of hazard-predictive features for each of a plurality of natural gas leaks, the values of the set of hazard-predictive features being determined according to data collected by a vehicle-borne gas concentration measurement device performing a sequence of geospatially-referenced mobile gas concentration measurements along one or more survey paths, the collected data including gas concentration and location; and configure a set of parameters of the risk model according to the training data to generate predicted hazard level values for the plurality of natural gas leaks that match hazard level values in the training data.

BRIEF DESCRIPTION OF THE DRAWINGS

The foregoing aspects and advantages of the present invention will become better understood upon reading the following detailed description and upon reference to the drawings where:

FIG. 18 is a table of dispersion coefficients for various atmospheric conditions according to some embodiments of the present invention.

DETAILED DESCRIPTION

Apparatus and methods described herein may include or employ one or more interconnected computer systems such as servers, personal computers and/or mobile communication devices, each comprising one or more processors and associated memory, storage, input and display devices. Such computer systems may run software implementing methods described herein when executed on hardware. In the following description, it is understood that all recited connections between structures can be direct operative connections or indirect operative connections through intermediary structures. A set of elements includes one or more elements. Any recitation of an element is understood to refer to at least one element. A plurality of elements includes at least two elements. Unless otherwise required, any described method steps need not be necessarily performed in a particular illustrated order. A first element (e.g. data) derived from a second element encompasses a first element equal to the second element, as well as a first element generated by processing the second element and optionally other data. Making a determination or decision according to a parameter encompasses making the determination or decision according to the parameter and optionally according to other data. Unless otherwise specified, an indicator of some quantity/data may be the quantity/data itself, or an indicator different from the quantity/data itself. Computer programs described in some embodiments of the present invention may be stand-alone software entities or sub-entities (e.g., subroutines, code objects) of other computer programs. Computer readable media encompass storage (non-transitory) media such as magnetic, optic, and semiconductor media (e.g. hard drives, optical disks, flash memory, DRAM), as well as communications links such as conductive cables and fiber optic links. According to some embodiments, the present invention provides, inter alia, computer systems programmed to perform the methods described herein, as well as computer-readable media encoding instructions to perform the methods described herein.

Figure 1:
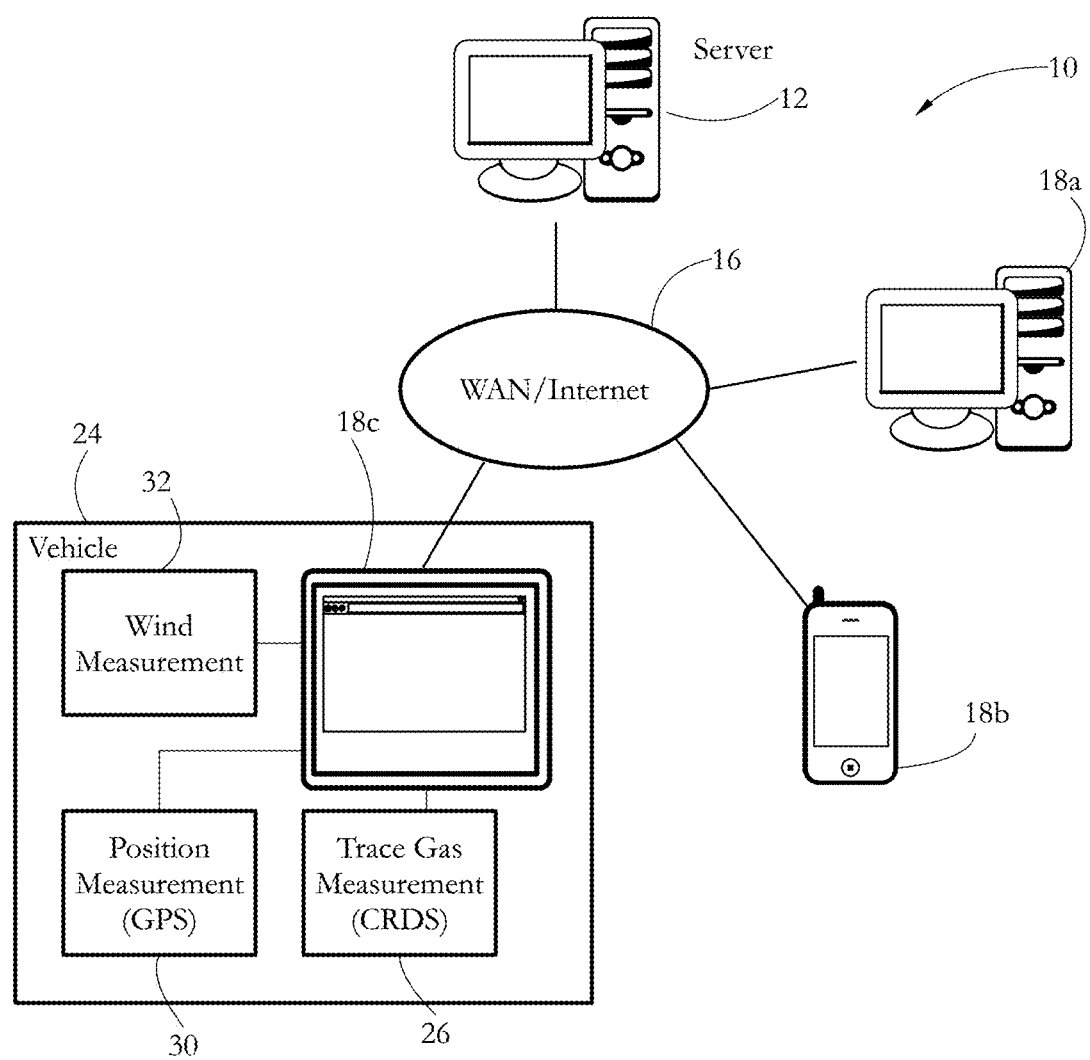
FIG. 1 shows a gas leak detection apparatus according to some embodiments of the present invention.

FIG. 1 shows a gas leak detection system 10 according to some embodiments of the present invention. System 10 comprises a service provider server computer system 12 and a set of client computer systems 18a-c all connected through a wide area network 16 such as the Internet. Client computer systems 18a-c may be personal computers, laptops, smartphones, tablet computers and the like. A vehicle 24 such as an automobile may be used to carry at least some client computer systems (e.g. an exemplary client computer system 18c) and associated hardware including a mobile gas measurement device 26, a location/GPS measurement device 30, and a wind measurement device 32. In a preferred embodiment, the mobile gas measurement device 26 may be a Picarro analyzer using Wavelength-Scanned Cavity Ring Down Spectroscopy (CRDS), available from Picarro, Inc., Santa Clara, Calif. Such analyzers may be capable of detecting trace amounts of gases such as methane, acetylene, carbon monoxide, carbon dioxide, hydrogen sulfide, and/or water. In particular applications suited for detection of natural gas leaks, a Picarro G2203 analyzer capable of detecting methane concentration variations of 3 ppb may be used. Wind measurement device 32 may include a wind anemometer and a wind direction detector (e.g. wind vane). GPS measurement device 30 may be a stand-alone device or a device built into client computer system 18c.

Figure 2:
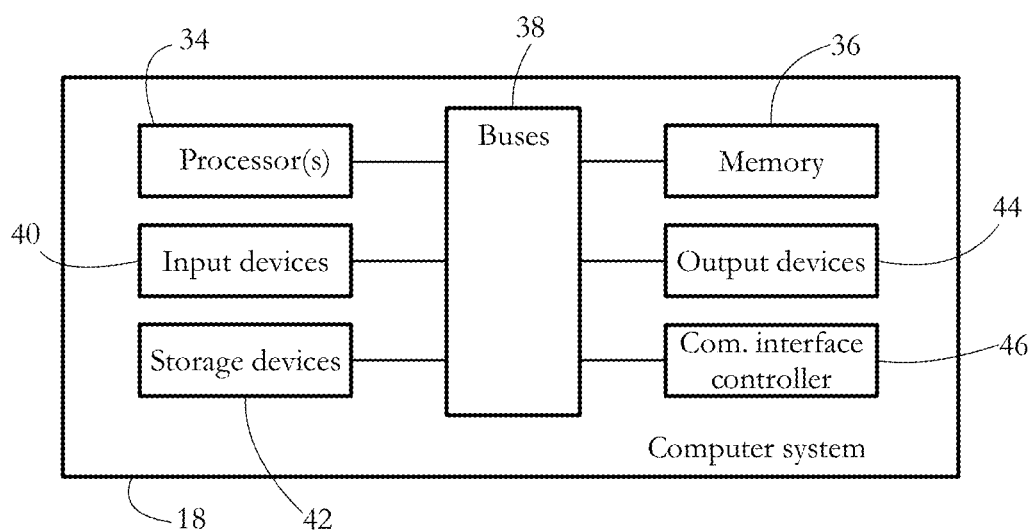
FIG. 2 illustrates hardware components of a computer system according to some embodiments of the present invention.

FIG. 2 schematically illustrates a plurality of hardware components that each computer system 18 may include. Such computer systems may be devices capable of web browsing and have access to remotely-hosted protected websites, such as desktop, laptop, tablet computer devices, or mobile phones such as smartphones. In some embodiments, computer system 18 comprises one or more processors 34, a memory unit 36, a set of input devices 40, a set of output devices 44, a set of storage devices 42, and a communication interface controller 46, all connected by a set of buses 38. In some embodiments, processor 34 comprises a physical device, such as a multi-core integrated circuit, configured to execute computational and/or logical operations with a set of signals and/or data. In some embodiments, such logical operations are delivered to processor 34 in the form of a sequence of processor instructions (e.g. machine code or other type of software). Memory unit 36 may comprise random-access memory (RAM) storing instructions and operands accessed and/or generated by processor 34. Input devices 40 may include touch-sensitive interfaces, computer keyboards and mice, among others, allowing a user to introduce data and/or instructions into system 18. Output devices 44 may include display devices such as monitors. In some embodiments, input devices 40 and output devices 44 may share a common piece of hardware, as in the case of touch-screen devices. Storage devices 42 include computer-readable media enabling the storage, reading, and writing of software instructions and/or data. Exemplary storage devices 42 include magnetic and optical disks and flash memory devices, as well as removable media such as CD and/or DVD disks and drives. Communication interface controller 46 enables system 18 to connect to a computer network and/or to other machines/computer systems. Typical communication interface controllers 46 include network adapters. Buses 38 collectively represent the plurality of system, peripheral, and chipset buses, and/or all other circuitry enabling the inter-communication of devices 34-46 of computer system 18.

Figure 3:
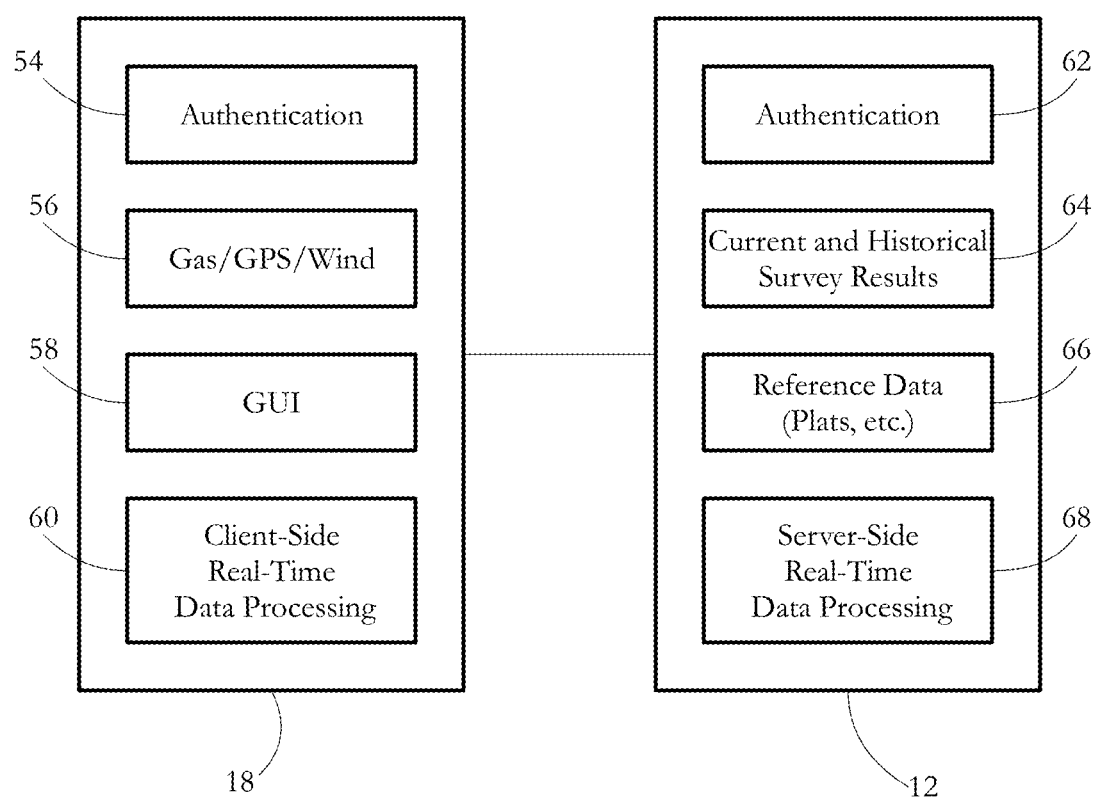
FIG. 3 shows a number of application or modules running on a client computer system and a corresponding server computer system according to some embodiments of the present invention.

FIG. 3 shows a number of applications or modules running on an exemplary client computer system 18 and corresponding server computer system 12. Authentication applications 54, 62 are used to establish secure communications between computer systems 12, 18, allowing client computer system 18 selective access to the data of a particular customer or user account. A client data collection module 56 collects real-time gas concentration, location data such as global positioning system (GPS) data, as well as wind speed and wind direction data. A graphical user interface (GUI) module 58 is used to receive user input and display survey results and other GUI displays to system users. A client-side real-time data processing module 60 may be used to perform at least some of the data processing described herein to generate survey results from input data. Data processing may also be performed by a server-side data processing module 68. Server computer system 12 also maintains one or more application modules and/or associated data structures storing current and past survey results 64, as well as application modules and/or data structures storing reference data 66 such as plats indicating the geographic locations of natural gas pipelines.

Figure 4:
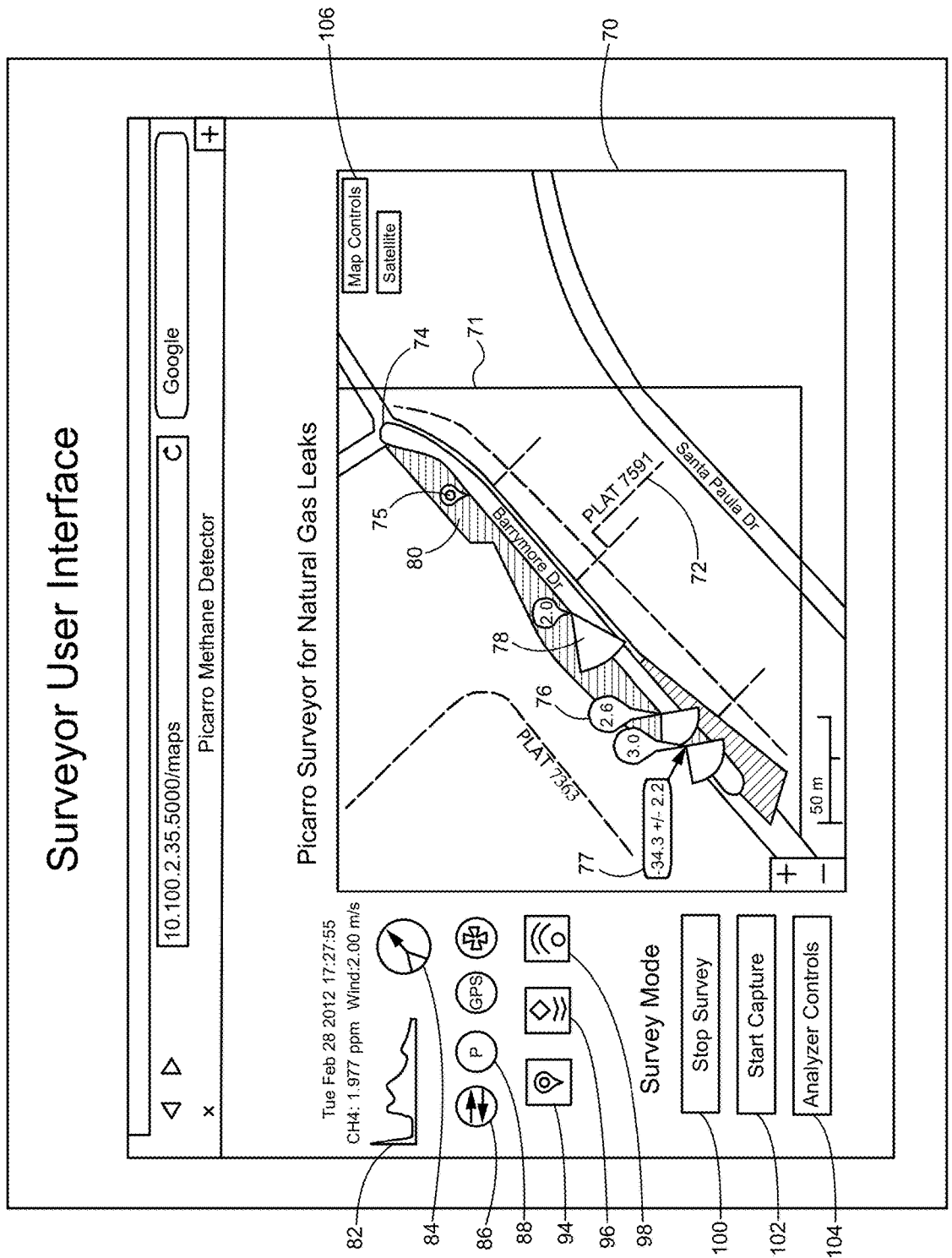
FIG. 4 is a schematic drawing of a screen shot on a graphical user interface displaying survey results on a street map according to some embodiments of the present invention.

FIG. 4 is a schematic drawing of a screen shot on a graphical user interface, displaying survey results on a street map 70 according to some embodiments of the present invention. The GUI screenshots are most preferably displayed on a client device in the vehicle, which may be connected to a server as described above. The illustrated screenshots show both exemplary user input, which may be used to control system operation, and exemplary real-time displays of collected/processed data. In the example, it includes the geo-referenced street map 70 showing plat lines 72. The plat lines 72 are preferably derived from gas company records. An active pipeline plat boundary 71 may also be displayed on the map 70. A user-selectable button 96 may be selected to overlay a selected pipeline plat on the map 70. Superimposed on the map 70 are one or more lines (preferably in a distinguishing color not shown in patent drawings) indicating the path 74 driven by the vehicle with the mobile gas measurement device on one or more gas survey routes. In this example, the path 74 shows the vehicle U-turned at the Y-shaped intersection. Optionally, a current location icon 75 may be overlaid on the map 70 to indicate the current surveyor location, e.g., the position of the vehicle with a gas measurement device and wind measurement device. A user-selectable button 94 may be selected to center the map 70 by current surveyor location. Also provided is a user-selectable start button 102 and stop button 100 to start/stop capturing gas for analysis. An analyzer control button 104 is user-selectable to control analyzer operations (e.g., shut down, start new trace, run isotopic analysis, etc.).

Peak markers 76 show the locations along the path 74 where peaks in the gas concentration measurements, which satisfy the conditions for being likely gas leak indications, were identified. The colors of the peak markers 76 may be used to distinguish data collected on different runs. The annotations within the peak markers 76 show the peak concentration of methane at the locations of those measurement points (e.g., 3.0, 2.6, and 2.0 parts per million). An isotopic ratio marker 77 may be overlaid on the map 70 to indicate isotopic ratio analysis output and tolerance (e.g., −34.3+/−2.2). Also displayed on the map 70 are search area indicators 78, preferably shown as a sector of a circle having a distinguishing color. Each of the search area indicators 78 indicates a search area suspected to have a gas leak source. The opening angle of the search area indicator 78 depicts the variability in the wind direction. The axis of the search area indicator 78 (preferably an axis of symmetry) indicates the likely direction to the potential gas leak source. Also displayed on the map 70 are one or more survey area indicators 80 (shown as hatched regions in FIG. 4) that indicate a survey area for a potential gas leak source. The survey area indicator 80 adjoins the path 74 and extends in a substantially upwind direction from the path. The survey area marked by each indicator 80 is preferably displayed as a colored swath overlaid or superimposed on the map 70. For example, the colored swaths may be displayed in orange and green for two runs. In preferred embodiments, the parameters of the search area indicators 78 and the survey area indicators 80 (described in greater detail with reference to FIGS. 8-11 below) are derived from measurements of the wind, the velocity of the vehicle, and optionally the prevailing atmospheric stability conditions.

Referring still to FIG. 4, the surveyor user interface also preferably includes a real-time CH4 concentration reading 82. A wind indicator symbol 84 preferably displays real-time wind information, which may be corrected for the velocity vector of the vehicle to represent the true wind rather than the apparent wind when the vehicle is in motion. Average wind direction is preferably indicated by the direction of the arrow of the wind indicator symbol 84, while wind direction variability is indicated by the degree of open angle of the wedge extending from the bottom of the arrow. Wind speed is preferably indicated by the length of the arrow in the wind indicator symbol 84. An internet connection indicator 98 blinks when the internet connection is good. A data transfer status button 86 is user-selectable to display data transfer status (e.g., data transfer successful, intermittent data transfer, or data transfer failed). An analyzer status button 88 is user-selectable to display current analyzer status such as cavity pressure, cavity temperature, and warm box temperature. A map control button 106 is user-selectable to open a map controls window with user-selectable layer options, discussed below with reference to FIG. 7.

Figure 5:
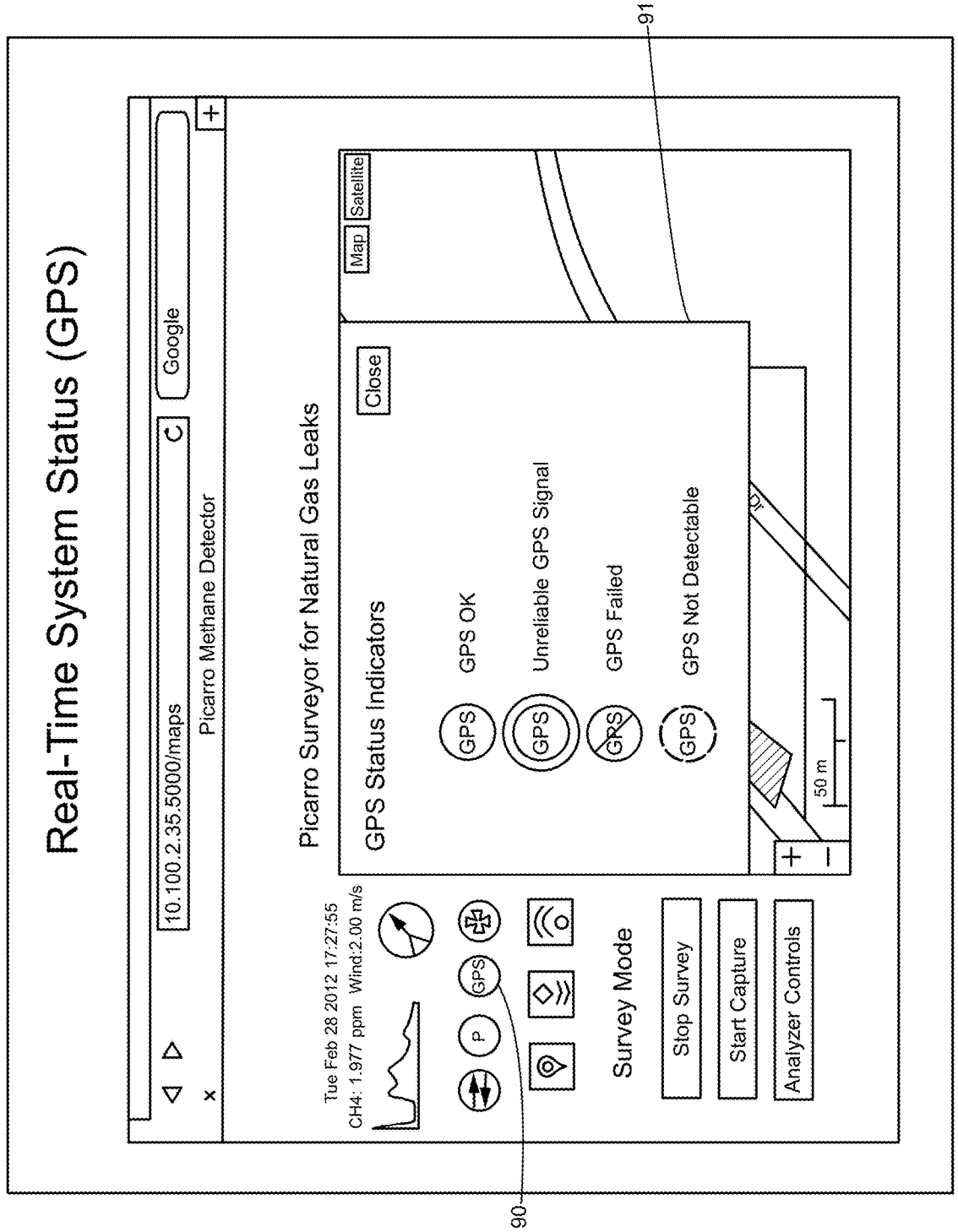
FIG. 5 is a schematic drawing of a screen shot on a graphical user interface with GPS indicators according to some embodiments of the present invention.

FIG. 5 is a schematic drawing of a screen shot on the graphical user interface, displaying a GPS status window 91, according to some embodiments of the present invention. A user-selectable GPS status button 90 may be selected to open the GPS status window 91. The GPS status window 91 preferably includes indicators of the current GPS status, such as "GPS OK", "Unreliable GPS signal", "GPS Failed", or "GPS Not Detectable".

Figure 6:
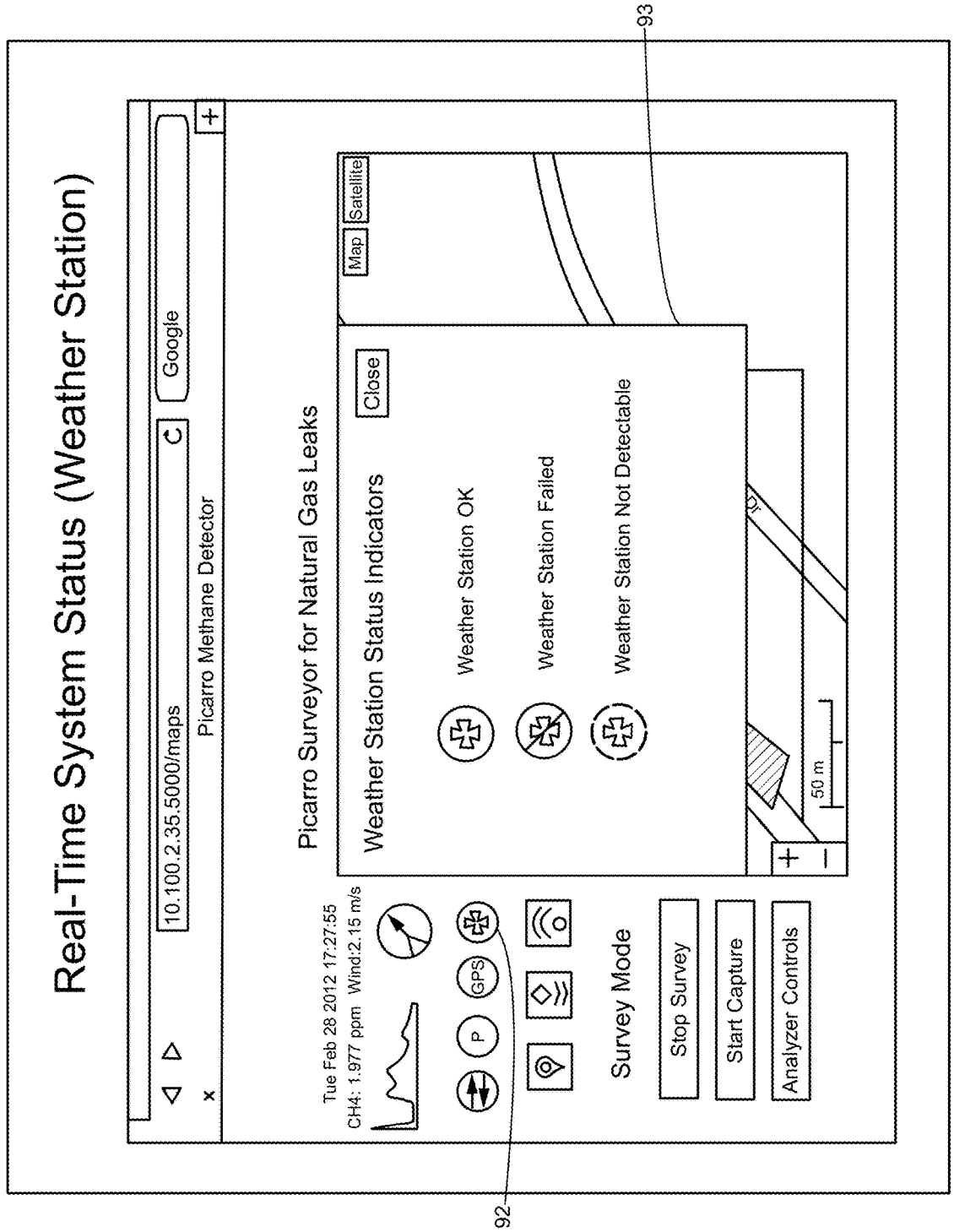
FIG. 6 is a schematic drawing of a screen shot on a graphical user interface with weather station status indicators according to some embodiments of the present invention.

FIG. 6 is a schematic drawing of a screen shot on the graphical user interface, displaying a weather station status window 93, according to some embodiments of the present invention. A user-selectable weather station status button 92 may be selected to open the weather station status window 93. The weather station status window 93 preferably includes indicators of the current weather station status, such as "Weather Station OK", "Weather Station Failed", or "Weather Station Not Detectable". Weather station data are preferably received in real-time and may include wind data and atmospheric stability conditions data relevant to the area being surveyed.

Figure 7:
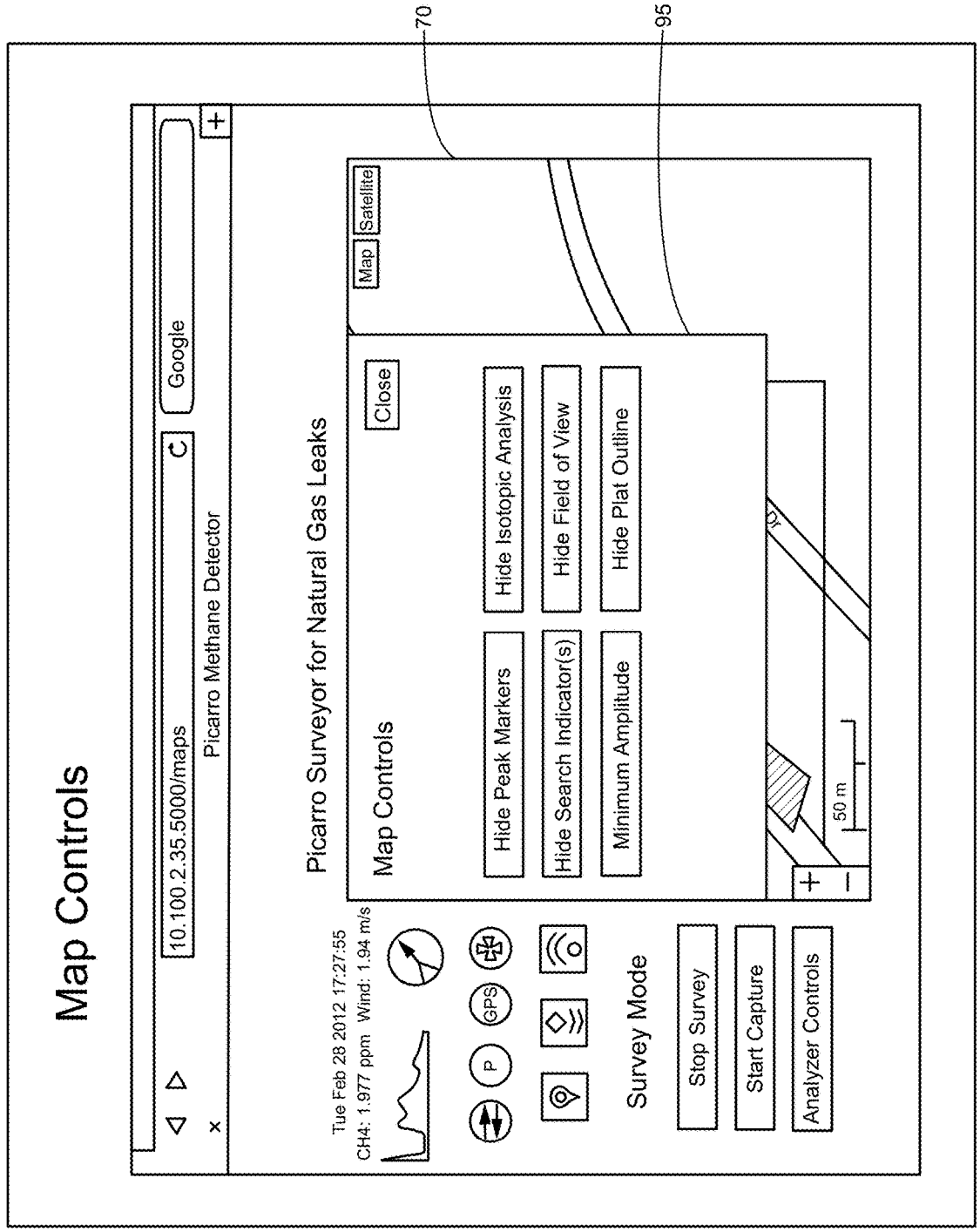
FIG. 7 is a schematic drawing of a screen shot on a graphical user interface with map controls according to some embodiments of the present invention.

FIG. 7 is a schematic drawing of a screen shot on the graphical user interface, displaying a map control window 95. Various elements displayed on the map 70 are regarded as layers which may be turned on or off. In this example, map controls window 95 includes six user-selectable buttons named "Hide Peak Markers", "Hide Search Area Indicators", "Minimum Amplitude", "Hide Isotopic Analysis", "Hide Field of View", and "Hide Plat Outline". The "Hide Peak Markers" button may be selected so that the markers indicating peak gas concentration measurements are not displayed on the map 70. The "Hide Search Area Indicators" button may be selected so that the search area indicators are not displayed on the map 70. The "Minimum Amplitude" button may be selected so that gas concentration peaks not meeting a minimum amplitude requirement are not displayed on the map 70. The "Hide Isotopic Analysis" button may be selected so that isotopic ratio analysis information is not displayed on the map 70 next to the peak markers. The "Hide Field of View" button may be selected so that the survey area indicator(s) are not displayed on the map 70. The "Hide Plat Outline" button may be selected so that the plat lines are not displayed on the map 70.

Figure 8:
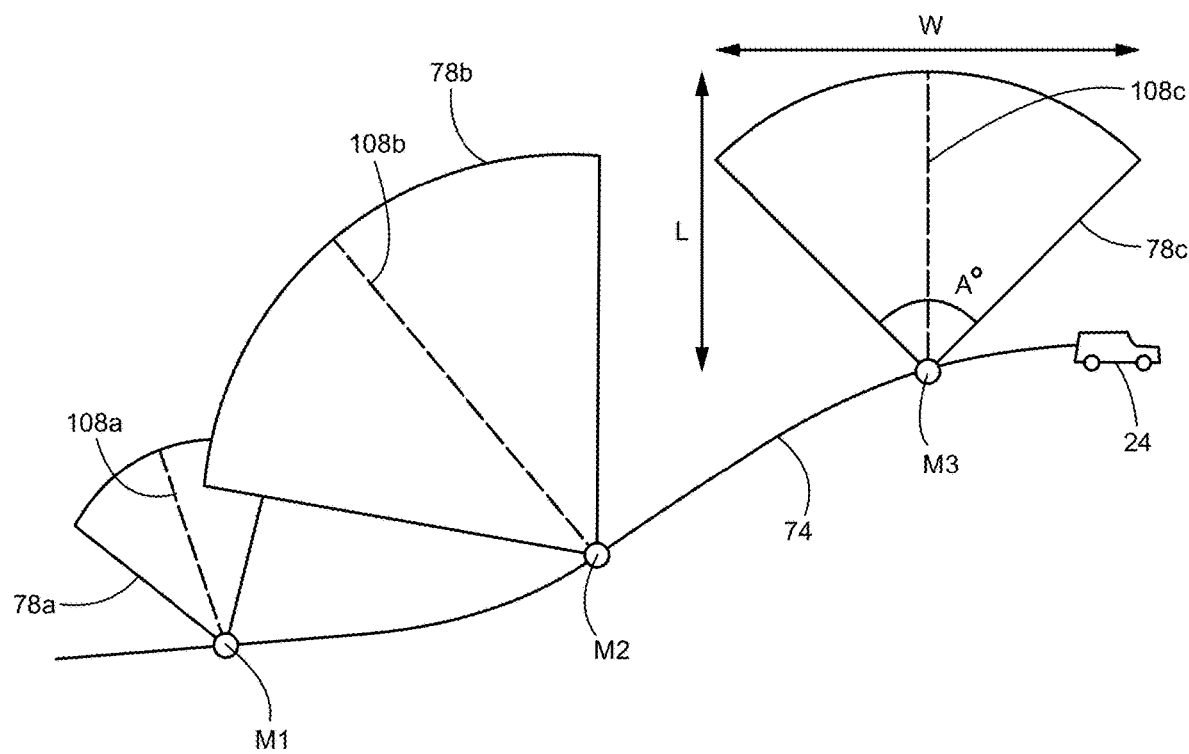
FIG. 8 is a schematic diagram of three search area indicators according to some embodiments of the present invention.

FIG. 8 is a schematic diagram of three search area indicators 78a, 78b, and 78c according to some embodiments of the present invention. Each of the search area indicators 78a, 78b, and 78c has a respective axis 108a, 108b, and 108c indicating a representative wind direction relative to a geo-referenced location of a corresponding gas concentration measurement point M1, M2, and M3. The gas concentration measurement points M1, M2, and M3 are positioned along the path 74 traveled by the vehicle 24 that carries a GPS device, a mobile gas measurement device, and wind measurement device for taking wind direction measurements and wind speed measurements. Each of the search area indicators, such as the search area indicator 78c, preferably has a width W relative to its axis 108c. The width W is indicative of a wind direction variability associated with wind direction measurements in the area of the gas concentration measurement point M3. In preferred embodiments, the width W is indicative of a variance or standard deviation of the wind direction measurements. Also in preferred embodiments, the search area indicator 78c has the shape of a sector of a circle, with the center of the circle positioned on the map at the location of the gas concentration measurement point M3. Most preferably, the angle A subtended by the sector of the circle is proportional to a standard deviation of the wind direction measurements taken at or nearby the measurement point M3. For example, the angle A may be set to a value that is twice or four times the angular standard deviation of the wind direction measurements. It is not necessary to display the gas concentration measurement points M1, M2, and M3 on the map along with the search area indicators 78a, 78b, and 78c. As previously shown in FIGS. 4 and 7, the measurement points and associated gas concentration measurements are preferably map layer options for an end-user that may be turned on or off.

Referring again to FIG. 8, the axis 108c of the search area indicator 78c is preferably an axis of symmetry and points in a representative wind direction relative to the gas concentration measurement point M3. The representative wind direction is preferably a mean, median or mode of the wind direction measurements taken at or nearby the measurement point M3, and indicates the likely direction to a potential gas leak source. The wind direction measurements may be taken from the vehicle 24 as it moves and converted to wind direction values relative to the ground (e.g., by subtracting or correcting for the velocity vector of the vehicle). In some embodiments, the axis 108c has a length L indicative of a maximum detection distance value representative of an estimated maximum distance from a potential gas leak source at which a gas leak from the source can be detected. For example, the length may be proportional to the maximum detection distance value, or proportional to a monotonically increasing function of the maximum detection distance value, such that longer maximum detection distance values are represented by longer axis lengths. In preferred embodiments, the maximum detection distance value and corresponding length L are determined according to data representative of wind speed in the search area. In some embodiments, the maximum detection distance value and the corresponding length L are determined according to data representative of atmospheric stability conditions in the search area. Each of the search area indicators 78a, 78b, and 78c may thus provide a visual indication of a likely direction and estimated distance to a potential gas leak source. Although a sector of a circle is the presently preferred shape for a search area indicator, alternative shapes for a search area indicator include, but are not limited to, a triangle, a trapezoid, or a wedge.

Figure 9:
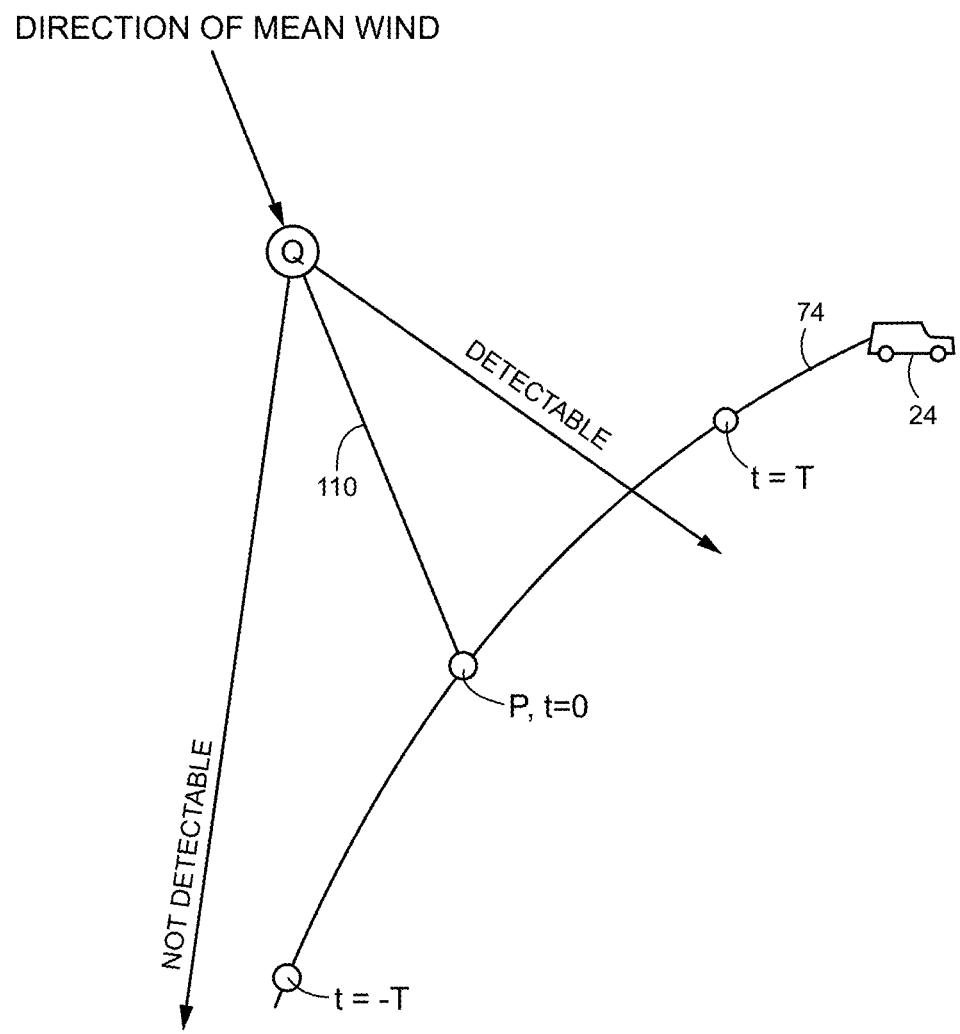
FIG. 9 is a schematic diagram illustrating wind lines relative to the path of a mobile gas measurement device for detecting or not detecting a gas leak from a potential gas leak source according to some embodiments of the present invention.

FIG. 9 is a schematic diagram illustrating an example of detecting or not detecting a gas leak from a potential gas leak source, according to some embodiments of the present invention. An indicator of a survey area (also sometimes referred to as a "field of view") is intended as an indication of how well the measurement process surveys the area around the path 74 traveled by the vehicle 24 that carries a GPS device, a mobile gas measurement device, and wind measurement device. The survey area indicator is designed such that if a potential gas leak source is located in the survey area and has a rate of leakage meeting a minimum leak rate condition, then an estimated probability of detection of a gas leak from the potential gas leak source at one or more measurement points P along the path 74 satisfies a probability condition.

Whether or not a potential gas leak source of a given strength is detectable by a gas measurement device of a given sensitivity depends on the separation distance of the source from the gas measurement device and on whether the wind is sufficient to transport gas from the gas leak source to the gas measurement device at some point along the path 74. In some embodiments, a physical model is employed that relates the measured gas concentration peak at the location of the vehicle 24 (in ppm, for example) to the emission rate of the potential gas leak source (in g/sec, for example) and the distance between the source and the detection point.

There are multiple possible models that describe the propagation of a gas leak as a plume through the atmosphere. One well-validated physical model for a plume (Gifford, F. A., 1959. "Statistical properties of a fluctuating plume dispersion model". Adv. Geophys, 6, 117-137) is to model the plume as a Gaussian distribution in the spatial dimensions transverse to the wind direction, or (for a ground level source), the concentration c (x, y, z) at a distance x downwind, y crosswind, and at a height z from a gas leak source of strength Q located on the ground is given by Equation (1):

$$C(x, y, z) = \frac{Q}{\pi v \sigma_y \sigma_z} e^{-y^2/2\sigma_y^2 - z^2/2\sigma_z^2} \qquad (1)$$

where v is the speed of the wind, and the plume dispersion half-widths $\sigma_y$ and $\sigma_z$ depend on x via functions that are empirically determined for various atmospheric stability conditions.

If we consider the plume center, where y=z=0, the concentration at the center is given by Equation (2):

$$C_{peak} = \frac{Q}{\pi v \sigma_y \sigma_z} \qquad (2)$$

The dimensions of the Gaussian distribution horizontally and vertically, half-widths $\sigma_y$ and $\sigma_z$, increase with increasing distance from the source. The amount they increase can be estimated from measurements of wind speed, solar irradiation, ground albedo, humidity, and terrain and obstacles, all of which influence the turbulent mixing of the atmosphere. However, if one is willing to tolerate somewhat more uncertainty in the distance estimation, the turbulent mixing of the atmosphere can be estimated simply from the wind speed, the time of day, and the degree of cloudiness, all of which are parameters that are available either on the vehicle 24 or from public weather databases in real time. Using these available data, estimates of the Gaussian width parameters can be estimated using the Pasquill-Gifford-Turner turbulence typing scheme (Turner, D. B. (1970). "Workbook of atmospheric dispersion estimates". US Department of Health, Education, and Welfare, National Center for Air Pollution Control), or modified versions of this scheme.

For a given sensitivity of the gas measurement device, there is a minimum concentration which may be detected. Given a gas leak source of strength greater than or equal to the minimum concentration, the source will be detected if it is closer than an estimated maximum distance $X_{max}$, where this is the distance such that $\sigma_y \sigma_z = Q/(\pi v c)$. If the wind is blowing gas directly from the gas leak source to the gas measurement device, the estimated maximum distance $X_{max}$ is the distance beyond which the source may be missed. This estimated maximum detection distance may depend upon atmospheric stability conditions as well as wind speed. The formula diverges to infinity when the wind speed is very small, so it is advisable to set a lower limit (e.g., 0.5 m/s) for this quantity.

The minimum leak rate $Q_{min}$ is determined by the requirements of the application. For natural gas distribution systems, a minimum leak rate of 0.5 scfh (standard cubic feet per hour) may be used; below this level, the leak may be considered unimportant. Other minimum leaks rates (e.g. 0.1 scfh, 1 scfh, or other values within or outside this range) may be used for natural gas or other leak detection applications. The minimum detection limit of the plume $C_{min}$ is given either by the gas detection instrument technology itself, or by the spatial variability of methane in the atmosphere when leaks are not present. A typical value for $C_{min}$ is 30 ppb (parts-per-billion) above the background level (typically 1,800 ppb). Given these two values for $Q_{min}$ and $C_{min}$, and by predicting $\sigma_y$ and $\sigma_z$ given atmospheric measurements (or with specific assumptions about the state of the atmosphere, such as the stability class), one may then determine the estimated maximum detection distance $X_{max}$ by determining the value for $X_{max}$ that satisfies the following equality, Equation (3):

$$C_{min} = \frac{Q_{min}}{\pi v \sigma_y \sigma_z}. \quad (3)$$

In some embodiments the relationship between $\sigma_y$ and $\sigma_z$ and $X_{max}$ is provided by a functional relationship, a lookup table, or similar method. Because $\sigma_y$ and $\sigma_z$ are monotonically increasing functions of $X_{max}$, a unique value can be determined from this process. For example, one useful functional form is a simple power law, where the coefficients a, b, c, and d depend on atmospheric conditions: $\sigma_y = ax^b$; $\sigma_z = cx^d$.

In some embodiments, the concentration C measured close to the ground of a Gaussian plume due to a gas leak source on the ground depends on the rate of emission Q of the source, the distance x between the source and the gas measurement device, and the speed of the wind blowing from the source to the gas measurement device, in accordance with an expression of the form (Equation 4):

$$C = \frac{Q}{\pi v \sigma_y(x) \sigma_z(x)} \quad (4)$$

The expressions for $\sigma_y(x)$ and $\sigma_z(x)$ depend on the stability class of the atmosphere at the time of measurement. In some embodiments, the stability class of the atmosphere is inferred from the answers to a set of questions given to the operator, or from instruments of the vehicle, or from data received from public weather databases. As shown in the table of FIG. 18, coefficients A, B, C, D, E and F may depend on surface wind speed and atmospheric conditions such as day or night, incoming solar radiation, and cloud cover. Mathematical forms for $\sigma_y(x)$ and $\sigma_z(x)$ are documented in Section 1.1.5 of the User's Guide for Industrial Source Complex (ISC3), Dispersion Models Vol. 2 (US Environmental Protection Agency document EPA-454/B955-003b September 1995). Given the sensitivity of the gas measurement device and the rate of emission of the smallest potential gas leak source of interest, equation (4) may be solved to find the estimated maximum distance $X_{max}$ beyond which a potential gas leak source may be missed by the gas measurement device.

Figure 16:
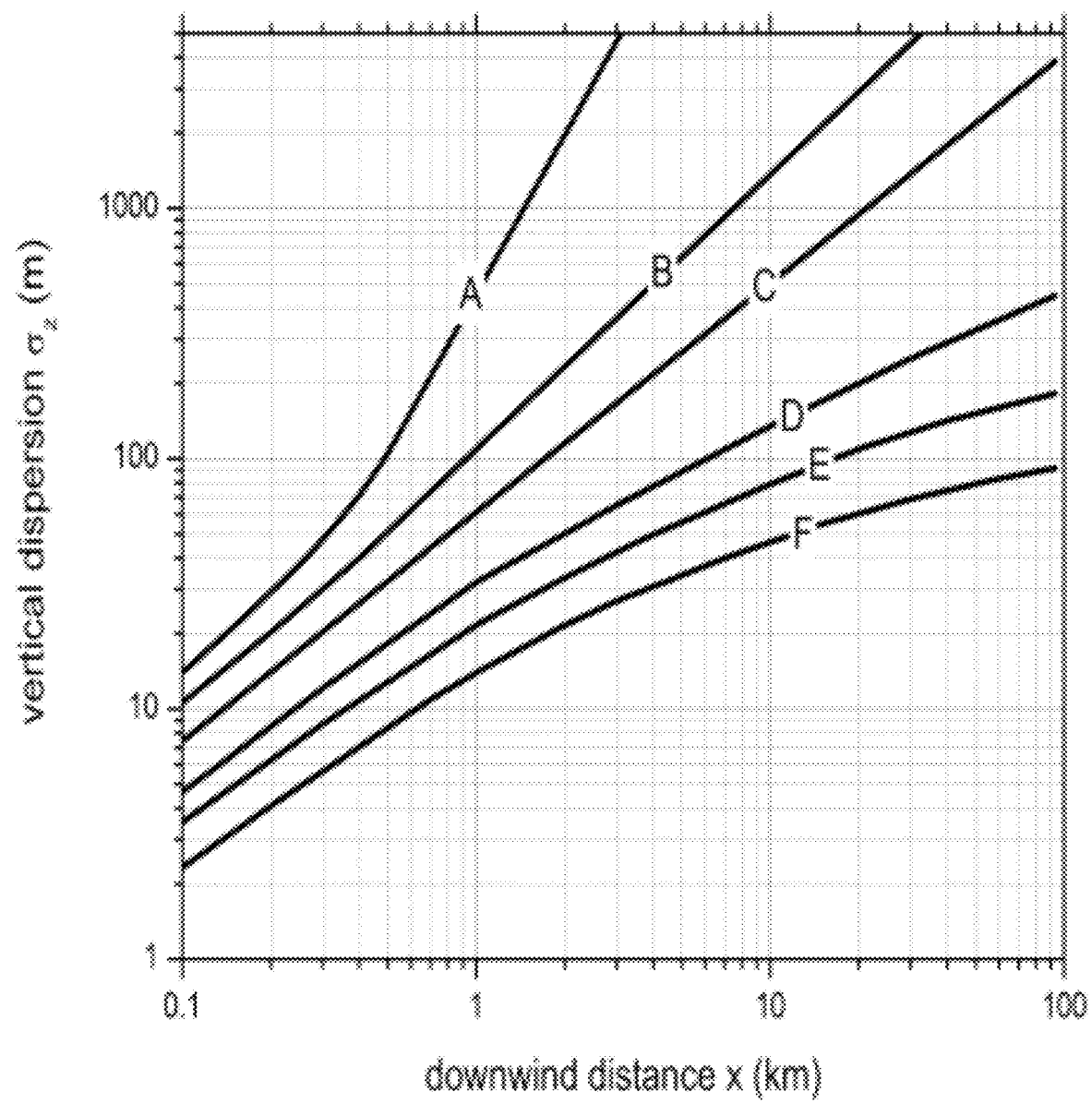
FIG. 16 is a graph of vertical dispersion coefficients of a gas plume as a function of downwind distance from a gas leak source according to some embodiments of the present invention.
Figure 17:
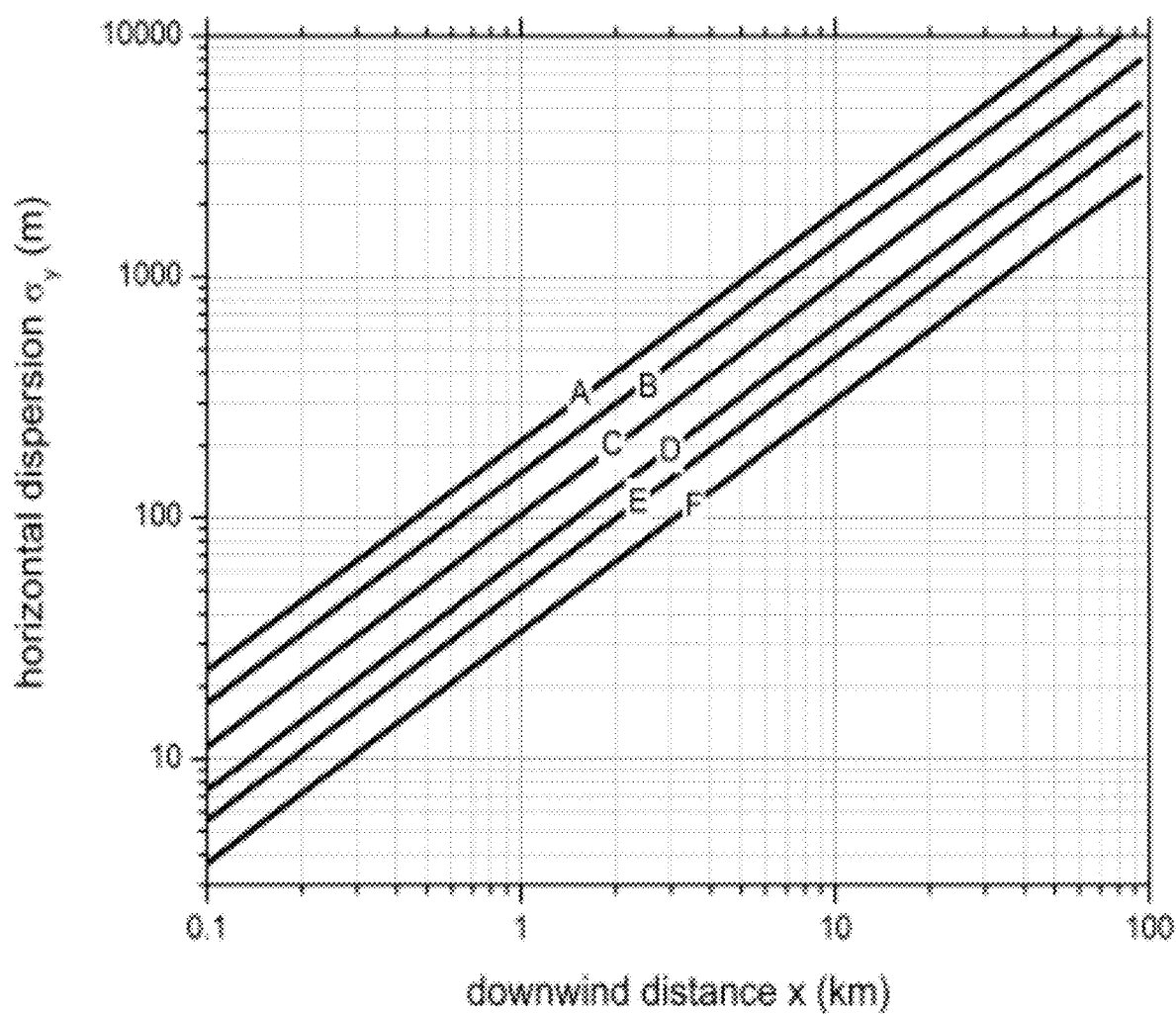
FIG. 17 is a graph of crosswind dispersion coefficients of a gas plume as a function of downwind distance from a gas leak source according to some embodiments of the present invention.

FIG. 16 is a graph of vertical $\sigma_z(x)$ dispersion coefficients of a gas plume as a function of downwind distance from a gas leak source according to some embodiments of the present invention. FIG. 17 is a graph of crosswind $\sigma_y(x)$ dispersion coefficients of a gas plume as a function of downwind distance from a gas leak source according to some embodiments of the present invention. The graphs are from from de Nevers, 2000, Air Pollution Control Engineering, The McGraw-Hill Companies, Inc. The dispersion coefficients are functions of downwind distance x. In this example, dispersion coefficients are calculated based on atmospheric stability. The table of FIG. 18 gives the atmospheric stability class as a function of wind speed, day or night, cloud cover, and solar radiation. In some embodiments, the dispersion coefficients and/or the estimated maximum distance $X_{max}$ may depend upon an urban or rural environment for the gas concentration measurements and plume dispersion. For example, the estimated maximum distance $X_{max}$ may be less in an urban environment with buildings or other structures than in a rural environment.

The actual distance at which a gas leak source may be detected is reduced if there is some variability or uncertainty in the direction of the wind. This is because there is a probability that the wind blows gas in a direction such that it does not intercept the path 74 of the vehicle 24 (FIG. 9). In practice this uncertainty is usually larger than the intrinsic angular uncertainty $\sigma_y/x$ implied by the Gaussian plume model. In order to determine the effective survey area of the mobile gas measurement device, assume for this example that the wind speed remains approximately constant within a time interval $-T<t<T$ bounding the time $t=0$ at which the vehicle 24 passes through a particular point P on the path 74, but that the wind direction (angle) is distributed as a Gaussian with a known mean and standard deviation.

As shown in FIG. 9, we consider the line 110 through the measurement point P pointing toward the direction of the mean wind, and whether a candidate point Q on this line qualifies to be within the boundary of the survey area (i.e., within the field of view of the mobile gas measurement device of the vehicle 24). We also consider drawing a sample from the distribution of wind directions and drawing a line through the candidate point Q in this direction. If this line intersects the path 74 of the vehicle 24 within the time interval $-T<t<T$, and the distance from the candidate point Q to the point of intersection with the path 74 is less than or equal to the estimated maximum distance $X_{max}$, then this is regarded as detectable by the mobile gas measurement device since the potential gas leak source at the candidate point Q would have been detected along the path 74. The quantity T sets the time interval during which it is expected to detect the gas coming from the candidate point Q at measurement point P. Theoretically, the time interval can be large, but it may not be reasonable to assume that the wind statistics remain unchanged for an extended period of time. In some embodiments, the wind direction measurements are taken during a time interval less than or equal to about 2 minutes, during which time interval a gas concentration is measured at the gas concentration measurement point P. More preferably, the time interval is in the range of 10 to 20 seconds.

Figure 10:
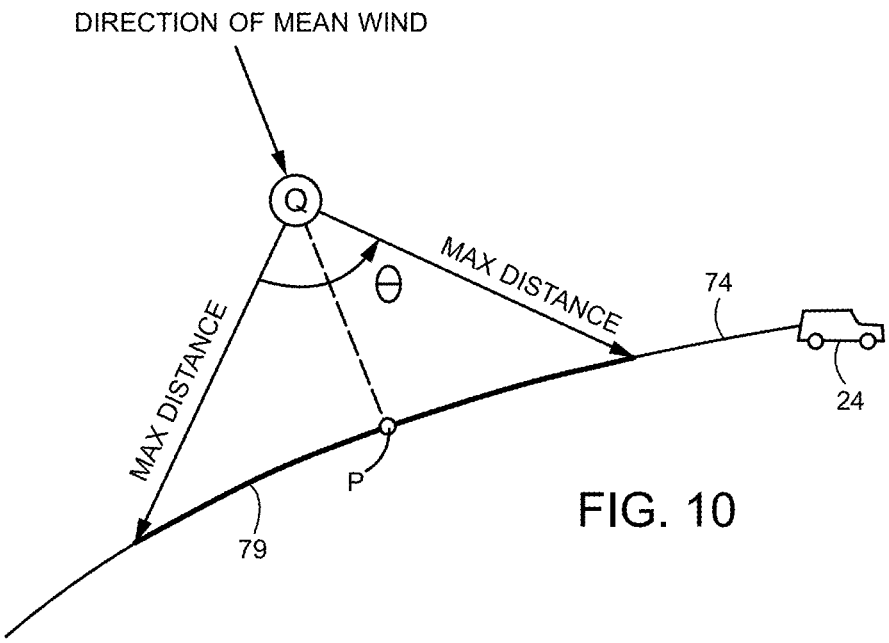
FIG. 10 is a schematic diagram of wind direction and a path of a mobile gas measurement device used to estimate a probability of detection of a gas leak from a potential gas leak source at one or more measurement points along the path according to some embodiments of the present invention.

FIG. 10 is a schematic diagram showing the estimation of a probability of detection at the measurement point P of a gas leak from a potential gas leak source at the candidate point Q, according to some embodiments of the present invention. The probability of detection at measurement point P is estimated according to an angle $\theta$ subtended by a segment 79 of the path 74 relative to the candidate point Q for the potential gas leak source. The path segment 79 is positioned within a distance of the candidate point Q that is less than or equal to the estimated maximum distance $X_{max}$. The probability of detection is preferably estimated according to a cumulative probability of wind directions with respect to the subtended angle $\theta$. The cumulative probability of wind directions may be determined according to a representative wind direction (e.g., a mean, median, or mode of the wind direction measurements) and a wind direction variability (e.g., variance or standard deviation) calculated from the wind direction measurements.

The candidate point Q is deemed to be within the boundary of the survey area if the probability of successful detection of a potential gas leak source at the candidate point Q, over the distribution of wind directions, satisfies a probability condition. In some embodiments, the probability condition to be satisfied is an estimated probability of successful detection greater than or equal to a threshold value, typically set at 70%. In general, as the candidate point Q is moved a farther distance from the gas concentration measurement point P, the range of successful angles becomes smaller and the probability of success decreases, reaching a probability threshold at the boundary of the territory deemed to be within the survey area.

Figure 11:
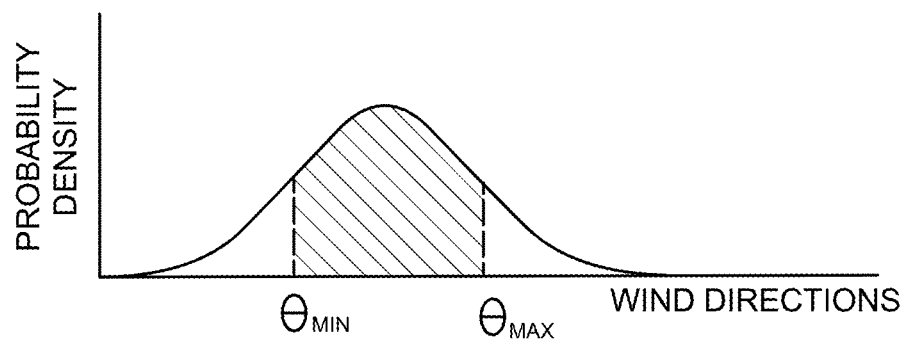
FIG. 11 is a graph of probability density vs. wind directions for estimating a probability of detection of a gas leak from a potential gas leak source according to some embodiments of the present invention.

FIG. 11 is a graph of probability density vs. wind directions for estimating a probability of detection of a gas leak from a potential gas leak source, according to some embodiments of the present invention. The area under the curve spans a range of possible angles θ for the successful detection of a potential gas leak from a candidate point. The probability density is preferably generated as a Gaussian or similar distribution from the calculated mean and standard deviation of the wind direction measurements in the area of the gas concentration measurement point P, FIG. 10. If the angle θ subtended by the path segment 79 relative to the candidate point Q encompasses a percentage of possible wind vectors that is greater than equal to a threshold percentage (e.g., 70%, although the percentage may be adjusted to other values such as 50%, 60%, 67%, 75%, 80%, or 90% in some embodiments), and if the distance from the candidate point Q to the measurement point P is less than the estimated maximum distance $X_{max}$, then the candidate point Q is deemed to be within the survey area.

The above process is repeated as different measurement points along the path 74 are chosen and different candidate points are evaluated for the probability of successful detection of a potential gas leak source. The cumulative distribution of the wind direction function together with a root finding algorithm are useful for efficiently determining the boundary of the survey area. For example, referring again to FIG. 10, the root finding algorithm may consider candidate points along the line of mean wind direction starting at the estimated maximum distance $X_{max}$ from measurement point P, and iteratively (e.g. using a bisection or other method) moving closer to the measurement point P along the mean wind direction line until the angle θ subtended by the path segment 79 is sufficient to meet the probability threshold, as determined from the cumulative probability of wind directions over the subtended angle θ, FIG. 11. Referring again to FIG. 4, the survey area indicator 80 may be displayed on the map 70 as a colored "swath" adjoining the path 74 and extending in a substantially upwind direction from the path.

Figure 12:
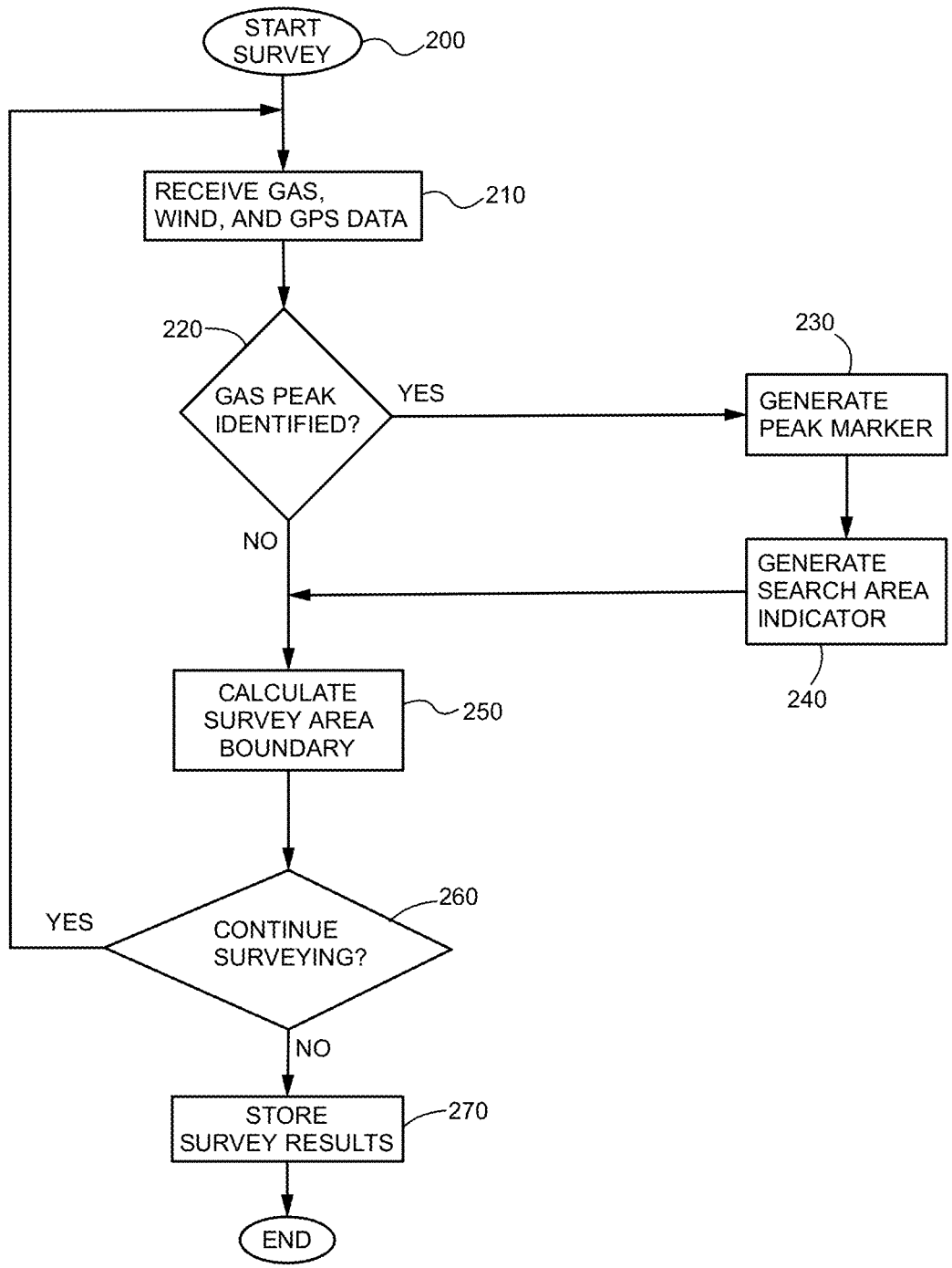
FIG. 12 is a flow chart showing steps for performing a gas leak survey according to some embodiments of the present invention.

FIG. 12 is a flow chart showing a sequence of steps to perform a gas leak survey according to some embodiments of the present invention. In step 200, the survey program is started, preferably by an operator in the vehicle using a graphical user interface (GUI). The operator begins to drive the vehicle on a survey route while the GUI displays a street map (FIG. 4). Gas concentration measurements are preferably performed rapidly along the survey route (e.g., at a rate of 0.2 Hz or greater, more preferably 1 Hz or greater). This enables the practice of driving the vehicle at normal surface street speeds (e.g., 35 miles per hour) while accumulating useful data. The gas concentration is measured initially as a function of time, and is combined with the output of the GPS receiver in order to obtain the gas concentration as a function of distance or location. Interpolation can be used to sample the data on a regularly spaced collection of measurement points. The concentration of methane typically varies smoothly with position, for the most part being equal to the worldwide background level of 1.8 parts per million together with enhancements from large and relatively distant sources such as landfills and marshes.

In step 210, at least one processor (e.g. of a client device, server device, or a combination) receives data representative of measured gas concentrations, wind direction measurements, wind speed measurements, and GPS data. In decision block 220, it is determined if a peak in gas concentration is identified. A peak may be identified from a gas concentration measurement above a certain threshold (or within a certain range), or exceeding background levels by a certain amount, which may be predetermined or user-selected. In some embodiments, the gas concentration and GPS data are analyzed using a peak-location method, and then each identified peak is subsequently fit (using linear or nonlinear optimization) for center and width. The functional form used for this fitting step may be a Gaussian pulse, since a Gaussian is commonly the expected functional form taken by gas plumes propagating through the atmosphere.

If a peak in gas concentration is not identified, then the program proceeds to step 250. If a peak in gas concentration is identified, then a peak marker is generated in step 230. The peak marker may be displayed on the map as a user-selectable layer, as previously discussed with reference to FIG. 4. In step 240, a search area indicator is generated to indicate the likely location of a gas leak source corresponding to the identified peak in gas concentration. The search area indicator may be displayed on the map as a user-selectable layer, as shown in FIG. 4. In step 250, the survey area boundary is calculated, and a survey area indicator may be displayed on the map as a user-selectable layer (hatched region in FIG. 4). In decision step 260, it is determined if the operator wishes to continue surveying (e.g., by determining if the "Stop Survey" button has been selected). If yes, the survey program returns to step 210. If not, the survey results are stored in memory in step 270 (e.g., in the survey results 64 of FIG. 3), and the survey program ends.

Figure 13:
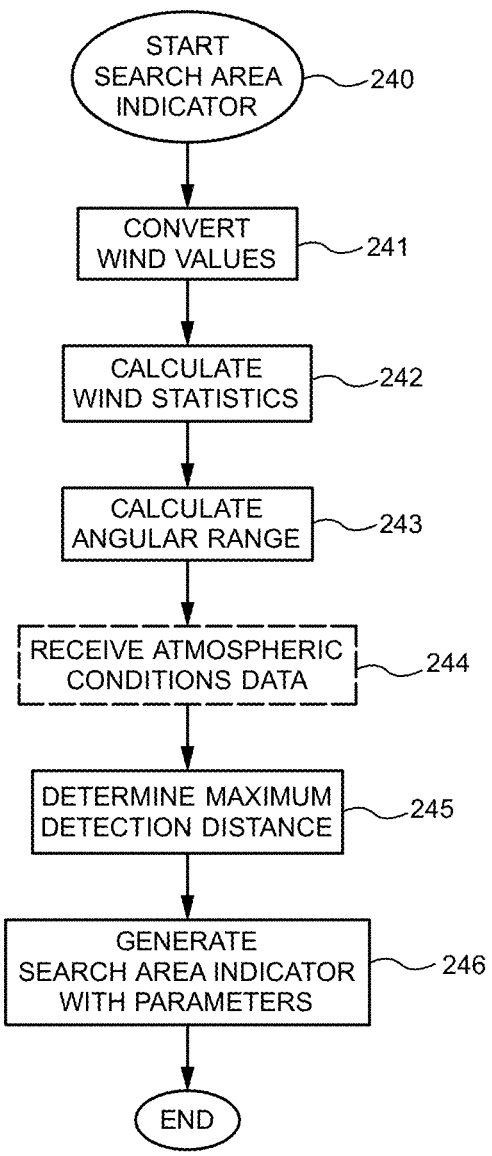
FIG. 13 is a flow chart showing steps for generating a search area indictor according to some embodiments of the present invention.

FIG. 13 is a flow chart showing a sequence of steps performed to generate a search area indicator according to some embodiments of the present invention. When a local enhancement in the gas concentration is detected, the likely direction and estimated distance to the potential gas leak source is preferably calculated from data representative of wind direction and wind speed measured during a time interval just prior to or during which the gas concentration was measured. The time interval is preferably fewer than 2 minutes, and more preferably in the range of 5 to 20 seconds. Calculating statistics from wind measurements may require some conversion if the measurements are made using sensors on a moving vehicle. A sonic anemometer is preferably used to measure wind along two perpendicular axes. Once the anemometer has been mounted to the vehicle, these axes are preferably fixed with respect to the vehicle. In step 241, wind speed and wind direction values that were measured relative to the vehicle are converted to wind speed and wind direction values relative to the ground by subtracting the velocity vector of the vehicle, as obtained from the GPS data. When the vehicle is stationary, GPS velocity may be ineffective for determining the orientation of the vehicle and wind direction, so it is preferable to use a compass (calibrated for true north vs. magnetic north) in addition to the anemometer.

In step 242, wind statistics are calculated from the converted wind values to provide the parameters for the search area indicator. The statistics include a representative wind direction that is preferably a mean, median, or mode of the wind direction measurements. The statistics also include a wind direction variability, such as a standard deviation or variance of the wind direction measurements. In step 243, an angular range of search directions, extending from the location of the gas concentration measurement point where the local enhancement was detected, is calculated according to the variability of the wind direction measurements. In optional step 244, atmospheric conditions data are received. Step 245 is determining a maximum detection distance value representative of the estimated maximum distance from the suspected gas leak source at which a leak can be detected. In some embodiments, the maximum detection distance value is determined according to Equation (3) or Equation (4), and the data representative of wind speed and/or atmospheric stability conditions. Alternatively, the maximum detection distance value may be a predetermined number, a user-defined value, empirically determined from experiments, or a value obtained from a look-up table. In step 246, the search area indicator is generated with the determined parameters, previously discussed with reference to FIG. 8.

Figure 14:
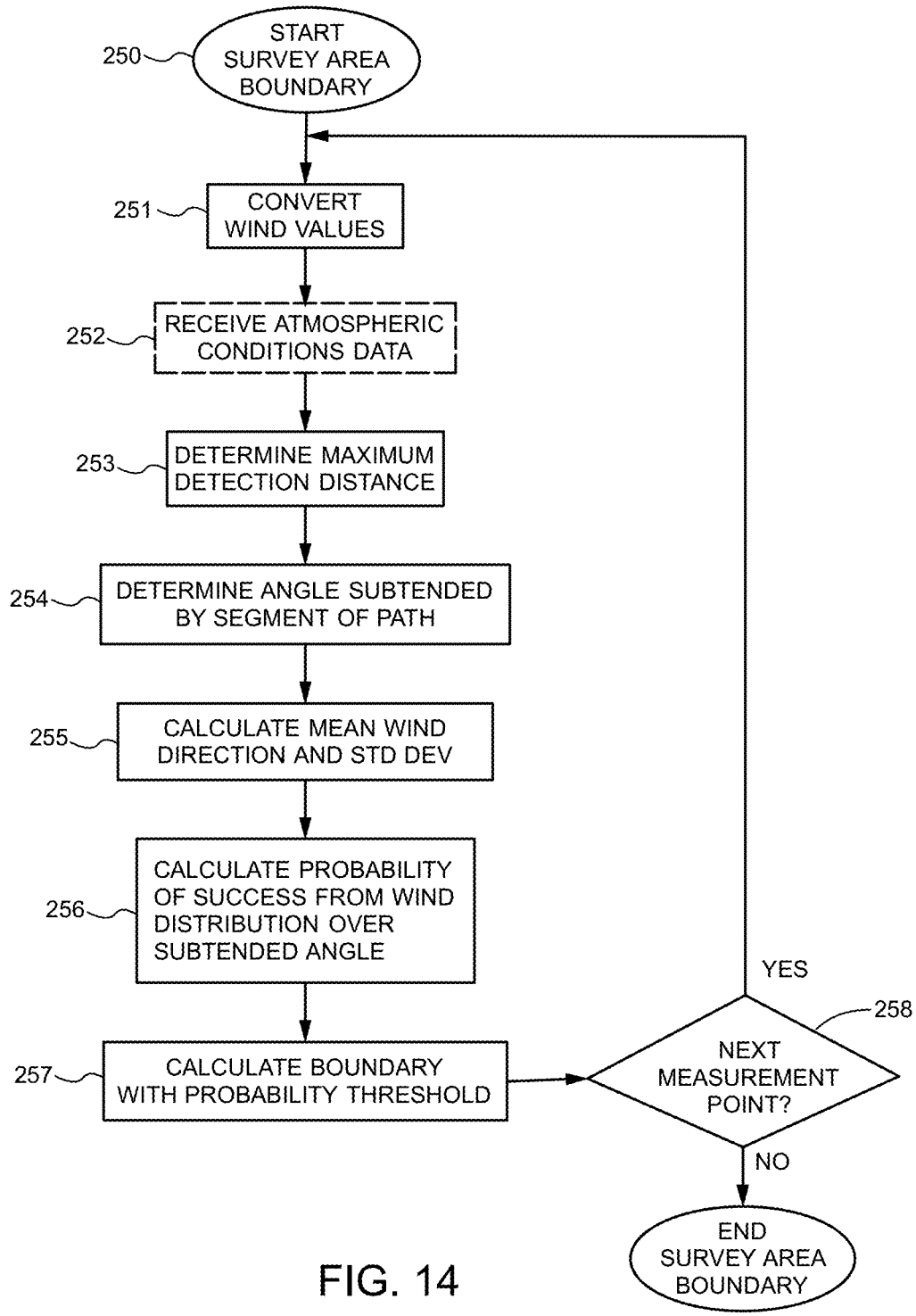
FIG. 14 is a flow chart showing steps for calculating a boundary of a survey area according to some embodiments of the present invention.

FIG. 14 is a flow chart showing a sequence of step performed to calculate a boundary of a survey area according to some embodiments of the present invention. In step 251, wind speed and wind direction values that were measured relative to the vehicle are converted to wind speed and wind direction values relative to the ground by subtracting the velocity vector of the vehicle, as previously described in step 241 above. In optional step 252, atmospheric conditions data are received. Step 253 is determining a maximum detection distance value representative of the estimated maximum distance from a suspected gas leak source at which a leak can be detected. In some embodiments, the maximum detection distance value is determined according to Equation (3) or Equation (4), and the data representative of wind speed and/or atmospheric stability conditions. Alternatively, the maximum detection distance value may be a predetermined number, a user-defined value, empirically determined from experiments, or a value obtained from a look-up table. In step 254, it is determined what angle $\theta$ is subtended by a segment of the path of the vehicle relative to the candidate point Q for the potential gas leak source. The path segment is positioned within a distance of the candidate point Q that is less than or equal to the estimated maximum distance.

In step 255, a representative wind direction (e.g., a mean, median, or mode of the wind direction measurements) and a wind direction variability (e.g., variance or standard deviation) are calculated from the wind direction measurements. In step 256, the probability of detection is estimated according to a cumulative probability of wind directions with respect to the subtended angle $\theta$. In step 257, the survey area boundary is calculated with a probability threshold. For example, if the angle $\theta$ subtended by the path segment relative to the candidate point encompasses a percentage of possible wind vectors that is greater than equal to a threshold percentage (e.g., 70%), and if the distance from the candidate point Q to the measurement point P is less than the estimated maximum distance $X_{max}$, then the candidate point Q is deemed to be within the survey area. In decision step 258, it is determined if the survey area boundary function is to continue with the next measurement point. If yes, steps 251-257 are repeated as different measurement points along the path are chosen and different candidate points are evaluated for the probability of successful detection of a potential gas leak source. If not, then the boundary function ends.

Figure 15:
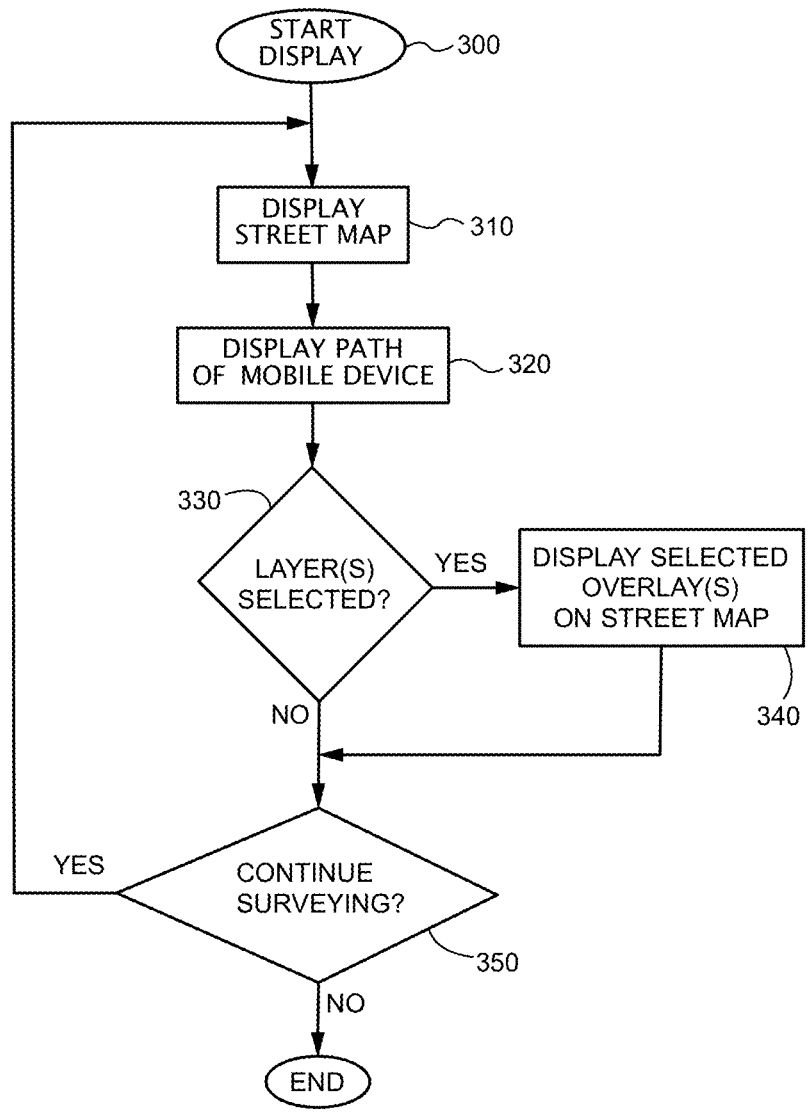
FIG. 15 is a flow chart showing steps for displaying layers overlaid or superimposed on a street map according to some embodiments of the present invention.

FIG. 15 is a flow chart showing steps for displaying layers overlaid or superimposed on a street map according to some embodiments of the present invention. In step 310, a street map is displayed, preferably on a GUI visible to the operator in the vehicle. In step 320, the path of the vehicle with the mobile gas measurement device is displayed on the map. Various elements displayed on the map are regarded as layers which may be turned on or off. In this example, the map controls window (FIG. 7) includes six user-selectable buttons named "Hide Peak Markers", "Hide Search Area Indicators", "Minimum Amplitude", "Hide Isotopic Analysis", "Hide Field of View", and "Hide Plat Outline". In decision step 330, it is determined if one or more of these layers is selected. If yes, the selected layer is displayed overlaid or superimposed on the street map in step 340. If not, it is determined if the survey is to continue. If yes, display steps 310-350 are repeated. If not, the display options may end.

The exemplary systems and methods described above allow a surveyor to locate potential gas leak sources efficiently and effectively in highly populated areas. The search area indicators provide likely direction and estimated maximum distance to the source of detected gas leaks, while the survey area indicators provide an estimated statistical measure of confidence that an area was successfully surveyed for potential gas leaks. These aspects provide significant improvement in finding gas leak sources over conventional methods where engineers scan the area very slowly and in all directions by trial and error to find the source of a gas leak. These aspects also account for wind that may quickly disperse a gas plume.

Figure 20:
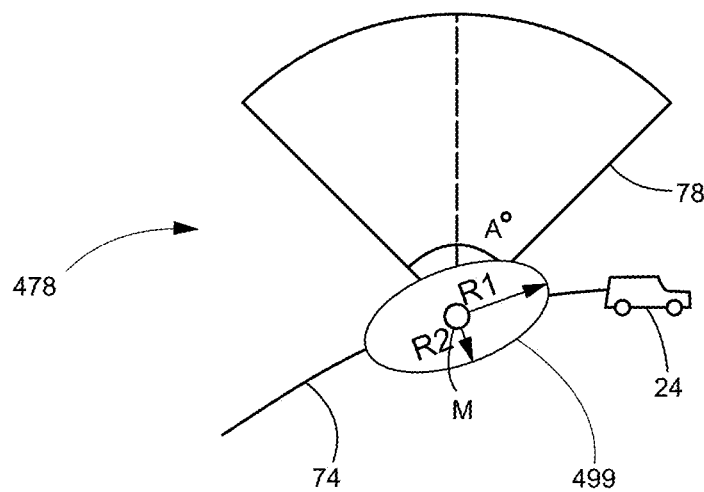
FIG. 20 shows an exemplary dual-zone search area indicator comprising an angular search area indicator and a positional uncertainty indicator according to some embodiments of the present invention.

Exemplary Systems and Methods Accounting for Uncertainties in Wind and/or Position Measurements In some embodiments, calculated uncertainties in wind and/or position measurements are taken into account in one or more of the steps described herein, in particular to generate search area indicators as illustrated in FIGS. 4 and 8, survey area indicators as illustrated in FIGS. 4 and 9, and/or dual-zone search area indicators as illustrated in FIG. 20, described below.

Wind Direction Uncertainty

Consider the exemplary search area indicator 78c shown in FIG. 8. As noted above, the search area indicator 78c may have the shape of a sector of a circle, with the center of the circle positioned on the map at the location of the gas concentration measurement point M3. The angle A subtended by the sector of the circle may be proportional to a standard deviation of the wind direction measurements taken at or nearby the measurement point M3. For example, the angle A may be set to a value that is twice or four times the angular standard deviation of the wind direction measurements.

Figure 19:
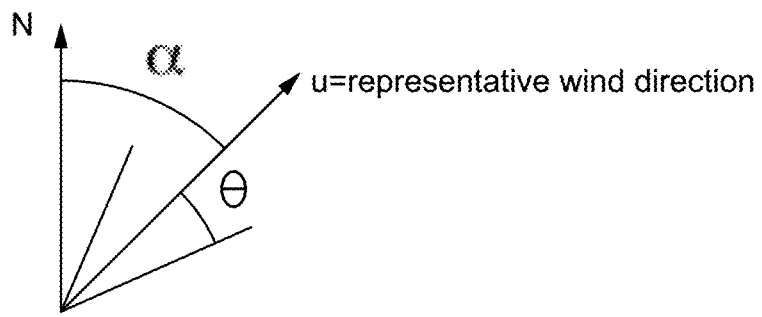
FIG. 19 illustrates an exemplary relationships between a reference (fixed) direction, a wind direction, and a wind direction variability and/or uncertainty indicator according to some embodiments of the present invention.

Consider now the exemplary configuration shown in FIG. 19, wherein N represents a reference direction (e.g. a North-South axis), and u is a representative wind direction. For example, u may be taken to the mean direction calculated over n samples, each characterized by an associated wind direction $u_1, u_2, \ldots, u_n$. The angle $\alpha$ represents the angle between the reference and representative wind directions, while the angle $\theta$ represents the angle between the representative wind direction and the search area indicator boundary, i.e. $\theta=A/2$, or half the angular extent of a search area indicator.

In some embodiments, a calculation of the angle $\theta$ (or A) may take into account both a variability of wind direction measurements, as described above, and a determined uncertainty in measured wind direction with respect to ground. For measurements taken using a moving vehicle, the wind speed and direction with respect to the ground are calculated by removing the effect of the survey vehicle motion from the apparent wind speed and direction measured onboard the vehicle. Possible sources of uncertainty in the wind direction with respect to the ground include, for example: the instrumental error of the wind sensor, the instrumental error of the sensor or system used to measure the speed of the vehicle, and compression or other distortion of the air stream at the location where the wind measurement is made as the survey vehicle moves.

In some embodiments, a value of the angular extent θ is determined according to a relation:

$$\theta = \beta(\theta_{variability}^2 + \sigma_{uncertainty}^2)^{1/2}$$

wherein the variability term represents a variability (e.g. standard deviation) of values relative to the mean, while the uncertainty term is a function of the magnitudes of the wind speed u and car speed v, for example $$\sigma_{variability} = \left(\frac{1}{N}\sum_{i=1}^{N}(\alpha - \alpha_i)^2\right)^{1/2}, \quad (6A)$$

with $\bar{\alpha} = 1/N \Sigma_i \alpha_i$ representing the mean value of $\alpha_i$, and $$\sigma_{uncertainty} = f(u,v), \quad (6B)$$

for example $$\sigma_{uncertainty} = \min\left(180°, a\frac{b+cv}{u+\varepsilon}\right), \quad (6C)$$

wherein $\alpha_i$ are measured wind directions each characterizing a sample, a, b, c, β and ε are parameter values, v represents a magnitude of a vehicle velocity vector, and u represents a magnitude of a wind direction vector.

In some embodiments, the overall scaling factor β has a value between 1 and 3, for example about 2. A larger overall scaling factor leads to the inclusion of a larger peripheral area in each search area indicator, while a smaller scaling factor leads to a narrower, more focused search area indicator.

The number N represents the number of samples used to generate a given search area indicator. In some embodiments, the number N has a fixed, peak-independent value. In some embodiments, the number N may depend on one or more determined characteristics of the peak, such as a spatial width of the peak and/or an estimate of a propagation distance (or time) for the plume. In general, the farther away a source is, the better a determined average wind direction and directional variability describes how good our knowledge of the true source direction is. Conversely, the closer the source, and the narrower the width of the peak in concentration, the more likely it is that an instantaneous wind direction indicates the direction to the source.

In some embodiments, a measurement uncertainty after averaging over n measurements may be determined as a function of the number of measurements, for example $$\sigma_{uncertainty} = \min\left(180°, \frac{a}{\sqrt{n}}\sum_i \frac{b+cv_i}{u_i}\right), \quad (6D)$$

which reduced to eq. (6C) for n=1. In other embodiments, the term a in eq. (6C) may be dependent on n, for example include a 1/sqrt(n) factor such as the one illustrated in eq. (6D).

Eq. (6D) illustrates embodiments in which a measurement uncertainty is calculated using a variable window, rather than a fixed window. In some embodiments, the averaging window may be chosen according to parameters such as peak width, wind speed, wind speed variability, wind direction variability, and car trajectory parameters such as parameters characterizing changes in direction. For example, a shorter averaging window may be used for narrower peaks, since narrower peaks are more likely to originate from nearby leaks, and in such cases an instantaneous wind direction may better constrain the direction of the leak than wind direction measurements taken at more distant time points. Additionally, when the wind direction is less variable, less averaging time may be needed to obtain a representative range of direction. Conversely, when the wind speed is low, the wind direction is likely to be more variable, and a longer averaging time may be useful. Parameters based on the trajectory of the car may be particularly useful in urban areas such as urban canyons, where the true wind direction may change abruptly after the survey vehicle turns onto a new street. In some embodiments, a shorter averaging window is used immediately after a sharp (e.g. more than 45 degrees, or 90 degrees) is made, since older wind measurement values are not representative of the instantaneous wind direction and/or speed.

In some embodiments, using a variable measurement window as described above may affect the determination of parameters other than measurement uncertainty. Such parameters may include a representative wind direction, a determined wind direction variability, and/or other parameters described above.

The minimum selection operation illustrated in eqs. (6C-D) may be used to constrain the angular uncertainty to a maximum angle of 180 degrees. Such an angle implies that no direction is more likely than any other, i.e. that the wind direction is considered to contain no useful information regarding the source location.

The parameters a, b, c, and ε may have empirically-determined values reflecting measurement uncertainties in a given experimental context. In exemplary embodiments, an overall uncertainty scaling factor a has a value between 0.5 and 1.5, a vehicle velocity added factor b has a value between 0 and 1, a vehicle velocity scaling factor c has a value between 1 and 5, and a wind velocity added factor ε has a value between 0.001 and 0.1. In one exemplary embodiment, a, b, c, and ε have values of about 0.33, 0, 2 and 0.01, respectively.

In some embodiments, a magnitude of the uncertainty in the reconstructed true wind direction due to multiple sources of measurement error, as well as its functional dependence on the speed of the vehicle and the true wind speed and direction with respect to the car's direction of travel may be determined using a Monte-Carlo simulation as described below. In a single realization of the simulation, a particular combination of a true vehicle velocity and true wind velocity is chosen. The effects of instrumental uncertainty on the measurements of car velocity and apparent wind velocity may be simulated by introducing measurement errors, such as Gaussian errors, according to the known specifications of the measurement devices. The true wind speed and direction are then reconstructed from the simulated noisy measurements of vehicle velocity and apparent wind speed as described above. Multiple realizations of the measurement are simulated for each combination of true wind and vehicle velocity. The uncertainty in the reconstructed true wind direction for a particular combination of true car velocity and true wind velocity may be taken to be the standard deviation of the distribution of the reconstructed wind direction about the true direction, or another indicator of the variability of the distribution. After performing the simulation for multiple combinations of true car velocity and wind velocity, a functional form for the dependence of reconstructed direction on wind speed and car speed may be generated.

In an exemplary embodiment, a simulated measurement error was determined in the presence of two sources of error which were taken to be equal in magnitude: the measurement error due to the wind sensor, described above, and a measurement error due to compression of the air stream above the vehicle, as described below. Equation (6C) was found to be a good approximation of the functional dependence of the reconstructed true wind direction uncertainty for car speeds less than 20 m/s when the values 1, 0, 2, 0.01, were chosen for parameters a, b, c, and ε, respectively, for a single measurement, and 0.33-1/sqrt(10), 0, 2, 0.01 for 10 measurements, respectively.

In some embodiments, wind sensors that employ ultrasonic time-of-flight or phase shift techniques often quote specs for measurement errors that are proportional to the measured wind speed, with typical relative uncertainties of 2% or better. We have found that the uncertainty in the speed of the vehicle as determined using a series of timed location measurements made with a high-precision (sub-meter) GPS system is usually much smaller than the measurement error given by common wind sensor specification. In addition, we have found that a correction to the component of apparent wind speed in the direction of motion by a simple multiplicative factor can reasonably account for the effect of the compression of the airstream by the profile of the vehicle, and that the precision with which one can measure the correction factor is typically better than 2%. When taken together, such sources of measurement error affect the uncertainty in the calculated true wind direction in a manner that increases approximately in proportion to car speed and inversely with wind speed, according to the form of eq. (6C).

Eq. (6C) may be better understood by considering FIG. 21, which shows an exemplary reconstructed mean wind bearing uncertainty (in degrees) after ten measurements as a function of vehicle speed (in m/s) for four different wind speed values, and for a, b, c, and ε values of 0.33, 0, 2 and 0.01, respectively, according to some embodiments of the present invention. As illustrated, the computed uncertainty increases with vehicle speed and decreases with wind velocity; the highest uncertainties correspond to high vehicle speeds and low wind velocities. For the sources of measurement error simulated here, we found that the reconstructed mean wind bearing uncertainty had a slight dependence on the angle between the true wind direction and the direction of the vehicle's motion, which could be safely disregarded.

Figures 21, 22:
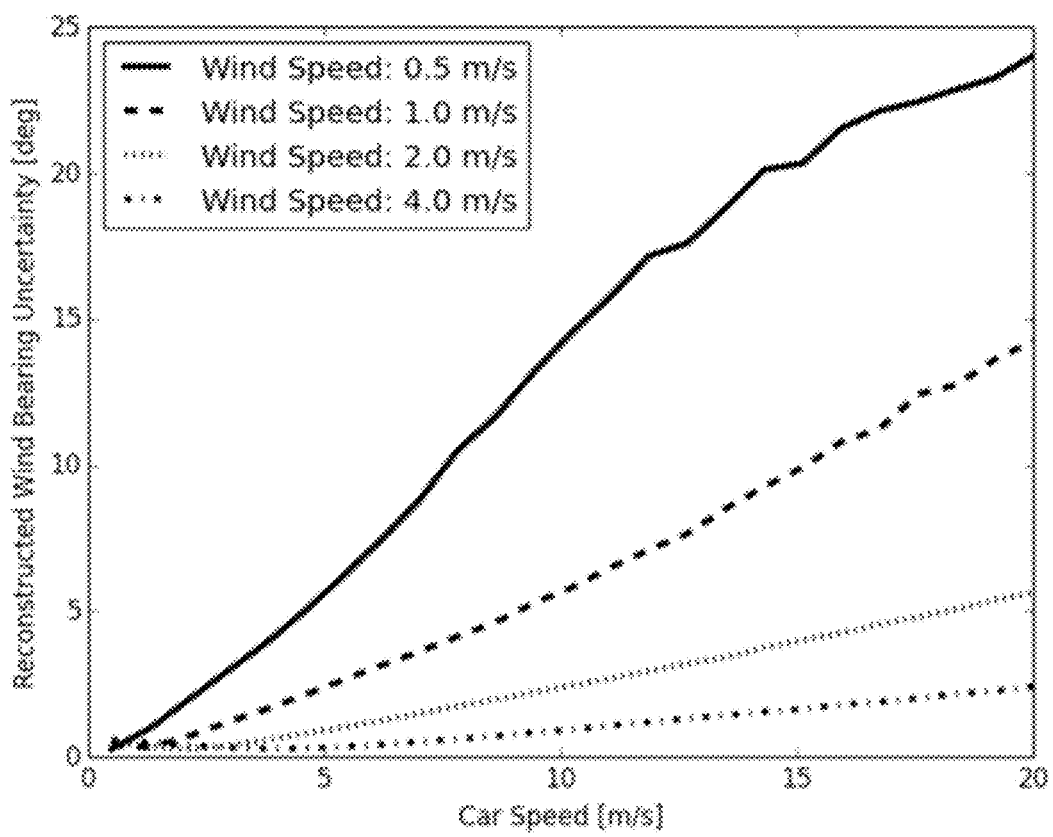
FIG. 21 illustrates an exemplary reconstructed wind bearing uncertainty as a function of vehicle speed for a fixed wind bearing and five different wind speed values according to some embodiments of the present invention.
FIG. 22 shows computed values of a number of parameters for three exemplary wind speeds according to some embodiments of the present invention.

FIG. 22 shows computed values of a number of parameters for three exemplary wind speeds according to some embodiments of the present invention. In particular, the derivative of uncertainty (eq. (6C)) with respect to wind speed, $d\sigma/dv$, is equal to $ac/u$, or approximately $2/u$ for the exemplary parameter values above. FIG. 22 illustrates how the results of a simulation (e.g. Monte-Carlo simulation) can be used to deduce or confirm a dependence of the uncertainty term on car speed and wind speed.

Figure 23:
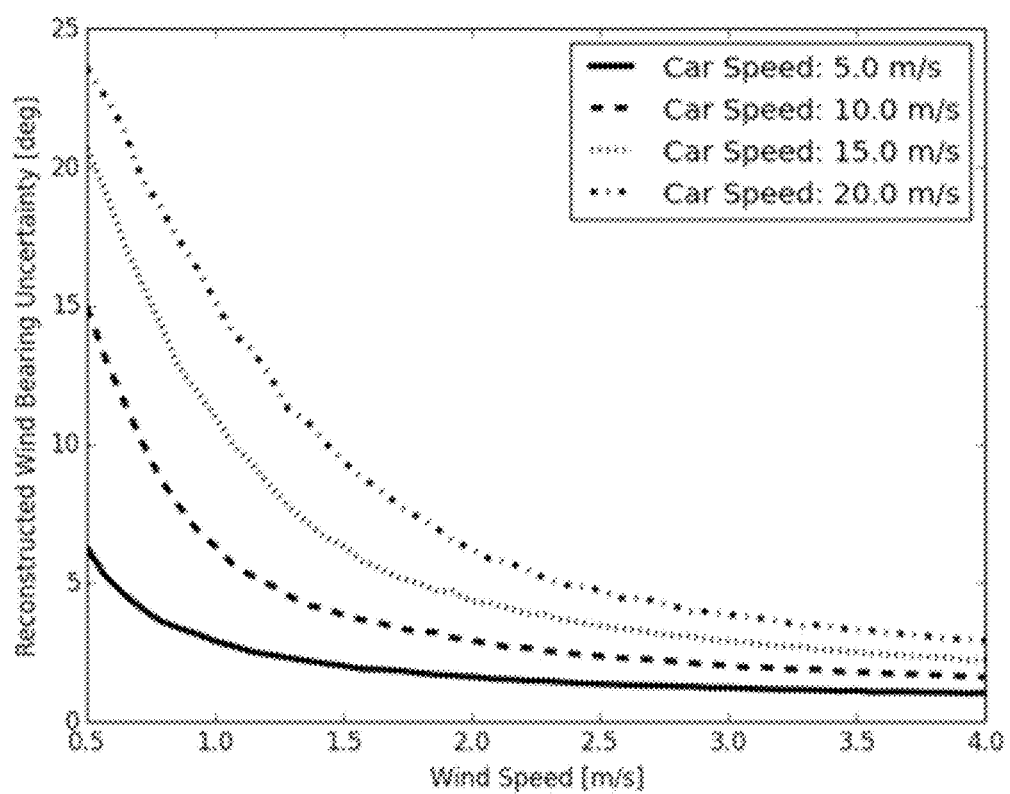
FIG. 23 shows an exemplary computed (simulated) pointing uncertainty and an associated analytical function as a function of wind speed for a vehicle speed of 10 m/s according to some embodiments of the present invention.

FIG. 23 shows an exemplary computed (simulated) pointing uncertainty (in degrees) after ten measurements, as a function of wind speed (in m/s) for four vehicle speeds, according to some embodiments of the present invention. It can be seen that the computed pointing uncertainty exhibits an inverse-dependence on wind speed as in equation 6C. We found that that the illustrated curves are sufficiently well described by equation 6C when the appropriate values of a, b, c and ε are chosen (0.33, 0, 2, and 0.01, respectively, for the curves of FIG. 23).

Peak Position Uncertainty

Figure 24:
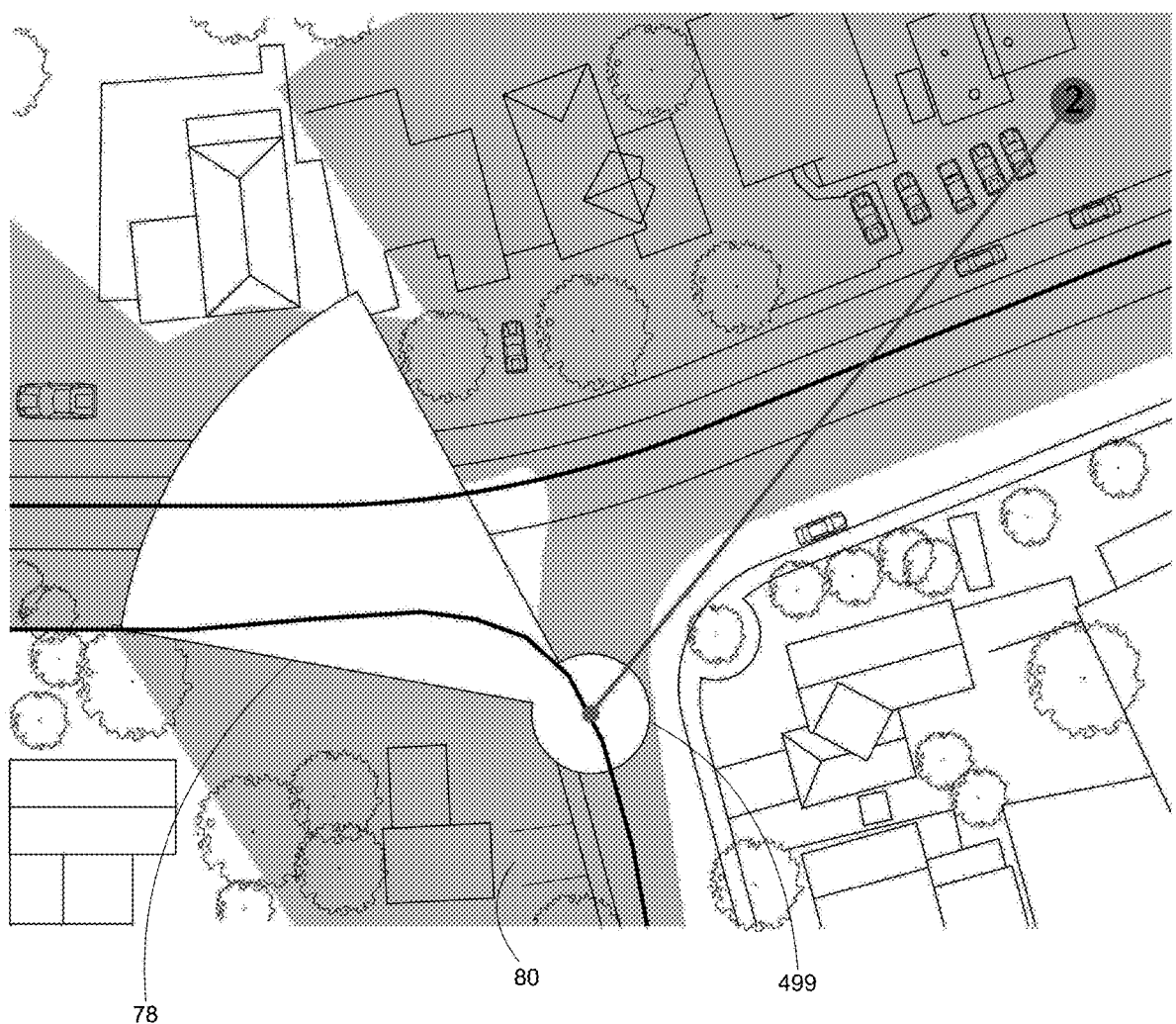
FIG. 24 shows an angular search area indicator and an associated positional uncertainty indicator, as well as a survey area indicator, all superimposed on a map display according to some embodiments of the present invention.

In some embodiments, an uncertainty in determined peak position is determined and represented graphically as described below. FIG. 20 shows an exemplary dual-zone search area indicator 478 that includes an angular indicator 78 reflecting wind variability and/or measurement uncertainty as described above, and a central positional uncertainty indicator 499 reflecting an uncertainty in the geospatially-referenced position determined to be associated with a peak event. Positional uncertainty indicator 499 may have a rounded shape, e.g. a circle or an ellipse centered at the determined event location. Positional uncertainty indicator 499 reflects a probability of near- or under-vehicle leaks, some of which may be present downwind from a recorded vehicle location. FIG. 24 shows an angular indicator 78 and an associated positional uncertainty indicator 499, as well as a survey area indicator 80, all superimposed on a map display, according to some embodiments of the present invention.

In some embodiments, positional uncertainty indicator 499 is formed by a circle or other symmetrical shape at vehicle speeds below a predetermined threshold, and by an ellipse or other elongated shape at vehicle speeds above the predetermined threshold. In other embodiments, positional uncertainty indicator 499 may have the same shape at all speeds, with the size of the shape fixed or speed-dependent. In some embodiments, positional uncertainty indicator 499 is a circle having a fixed radius corresponding to a 90% containment area for near or under-vehicle leaks. Such a containment area may be determined empirically, by comparing where confirmed locations of identified leaks are situated on a map relative to a recorded peak location. For example, positional uncertainty indicator 499 may have a radius between 10 and 30 feet, for example about 20 feet, for vehicle speeds below a threshold such as 30, 40, or 45 mph. For vehicle speeds above the threshold, and in particular above 45 mph, which are above those commonly used in leak surveys, positional uncertainty indicator 499 may be shaped as an ellipse, with the longer ellipse axis along the direction of motion reflecting the added positional uncertainty arising from imperfect synchronization between location and concentration measurements or other speed-dependent error source(s). For example, in some embodiments location and concentration measurements may be synchronized only to about 0.2-0.5 seconds, for example about 0.3 seconds, which corresponds to a significant positional uncertainty at high vehicle speeds. In some embodiments, positional uncertainty indicator 499 is centered at the location of an identified peak event; in some embodiments, positional uncertainty indicator 499 may be weighted toward the upwind direction, i.e. have a larger extent upwind and a lesser extent downwind from the associated peak location.

A measurement of concentration versus position involves the synthesis of data from two sources: a gas (e.g. methane) concentration analyzer, and a position determination system such as a GPS system. Both sub-systems measure their respective data with respect to time, and may have different reporting latencies, i.e. the time delays between the instant a measurement is made and the instant the measurement is reported a central computer or data acquisition system. The two measurements are synchronized in time in order to arrive at a result representing concentration as a function of geospatially-referenced position. Consequently, an uncertainty in the timing delay calibration between the two measurements will propagate as an uncertainty in the location where the peak concentration is detected.

In some embodiments, we found that a timing offset between concentration and position measurements can typically be found to a precision of 0.1 to 1 second. With a survey vehicle velocity of 5 to 10 meters per second, such a time offset translates into an error in the position of the detected gas peak ranging from about 0.5 meters to about 10 meters. Such a situation results in the possibility that leaks that lay on the path of the survey vehicle may appear to fall outside of a purely-angular area search area indicator, by appearing on a map to be downwind (behind) the peak concentration location as well as behind the angular search area wind indicator.

Furthermore, because of the finite accuracy of position measurement (GPS) systems, peak locations may tend to fall to the right or the left of the track of the survey vehicle by a distance reflecting the accuracy of the location measurement. In some embodiments, the position measurements can be made with an accuracy of about 1 meter or better. In addition, in some embodiments it was also found that, depending on the strength of the wind (especially in light-wind situations), leaks may be detected from distances of up to several meters downwind of the survey track, which can lead to a similar case as where the wind indicator alone does not cover the leak location. In addition, when depicting the location of the peak detection on a map or satellite image, another source of uncertainty arises from how well certain features or geo-referenced points in the image can be mapped to actual geographical coordinates. In one embodiment, we found that the magnitude of this error can be up to several meters, and can be the dominant source of error in the depiction of the measured peak detection position.

Such uncertainty in position may be addressed by considering a search area to include, in addition to angular wind direction indicator 78 (FIG. 20), a central positional indicator 499 centered at the peak detection position. In some embodiments, central positional indicator 499 may be shaped as an ellipse. In the following discussion, a circle may be considered to be a special case of an ellipse, i.e. an ellipse with equal axes. In some embodiments, one axis of the ellipse ($R_1$) is aligned with the instantaneous direction of motion of the survey vehicle at the location where the peak concentration is detected. The length of each axis of the ellipse may be chosen to be fixed or variable in a way that is suitable to account for one or more of the effects that lead to uncertainty in the detected peak gas location and/or uncertainty in leak location for near-vehicle leaks.

In some embodiments, the length of the axis of the ellipse that is aligned with the direction of motion ($R_1$) is scaled in proportion to the speed of the vehicle. A fixed timing-delay offset between the concentration and location measurements results in a positional error that scales directly with car speed. Consequently, scaling the ellipse axis with the vehicle speed reflects an expected positional uncertainty due to timing delay errors.

In some embodiments, the axis of the ellipse that is perpendicular to the direction of motion ($R_2$) is scaled according to data representative of wind speed, wind direction variability, and/or atmospheric stability. Such scaling reflects the observation that the distance at which upwind leaks may be detected can depend on the local wind speed as well as on the degree of atmospheric stability. If a fixed length is chosen for the axis perpendicular to the direction of vehicle motion, the length may be chosen to ensure that near-vehicle leaks fall within ellipse with a chosen frequency (probability) under typical survey conditions. In such case, a suitable value for $R_2$ may be chosen to be between about 1 and 10 meters, more particularly between about 3 and 8 meters, for example about 6 meters. In some embodiments an appropriate length may be chosen by driving multiple times upwind of a source at various distances, repeating the process for multiple sources, and constructing an appropriate probability distribution.

Scaling the minor and/or major axes is a way to account for how the likelihood of detecting the plume from a position upwind of the source changes as a function of the wind speed, variability of the wind direction, or atmospheric stability conditions. The lighter the wind and more variable the direction, the more likely it would be to detect the source from a position upwind with respect to the mean wind direction. Additionally, the likelihood of detecting the source from an upwind position may be a function of the degree of atmospheric stability. The more unstable the atmosphere (closer to stability class A), the more likely the plume dispersion is dominated by vertical mixing (as opposed to horizontal mixing) and the less likely it would be to detect the source from a position upwind of the source. In some embodiments, such scaling relationships may be determined empirically through systematic measurements.

In some embodiments, it may be desirable to require minimum values for the lengths of both axes, to ensure the ellipse does not collapse into a line or point. In an exemplary embodiment, the minimum length of each axis may have a value between 6 and 16 meters, for example about 12 meters (corresponding to a radius of 6 m in the case of a circle). In some embodiments it may be desirable to set an upper limit on the eccentricity of the ellipse, for example for visualization/aesthetic purposes. In an exemplary embodiment, the ratio of the lengths of the semimajor and semiminor axes may be limited to values between 1 and 4, with a preferred value of 2.

Survey Area Boundary Adjustments According to Wind and/or Position Uncertainties In some embodiments, the determination of a boundary of a survey area 80 as described above with reference to FIGS. 9-11 may take into account determined uncertainties in wind direction and measurement location determinations. The effect of including the measurement uncertainty on the probability density in FIG. 11 is to make the probability density distribution wider, such that a larger range of angles between theta min and theta max would be needed to fulfill the probability condition. If one maintains the same probability threshold as described above, the net effect is a reduction in the width of the field of view (FOV).

Figure 25:
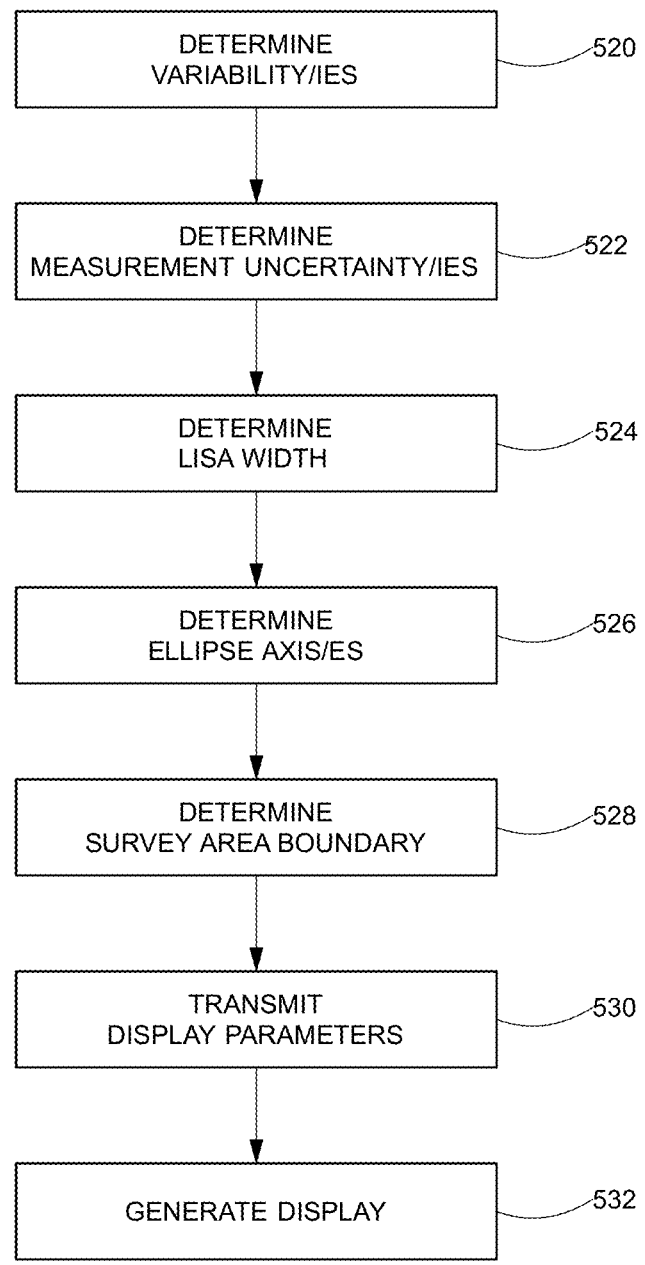
FIG. 25 shows an exemplary sequence of steps performed by at least one processor to generate a display according to determined variability and measurement uncertainty indicators, according to some embodiments of the present invention.

FIG. 25 shows an exemplary sequence of steps performed by at least one processor to generate a display according to determined variability and/or measurement uncertainty indicators, according to some embodiments of the present invention. In a step 520, one or more parameter variability indicators are determined as described above. In a step 522, one or more measurement uncertainty indicators are determined as described above. In a step 524, a width is determined for each search area indicator according to the determined variability and/or measurement uncertainty indicators as described above. In a step 526, the length(s) of one or both central LISA ellipse axes are determined according to the determined variability and/or measurement uncertainty indicators as described above. In a step 528, a survey area boundary is determined according to the determined variability and/or measurement uncertainty indicators as described above. In a step 530, determined display parameters are transmitted to a display device for display. In a step 532, the display device renders a display as shown above according to the received display parameters.

In some embodiments, the steps shown in FIG. 25 other than the final step 532 are performed on a cloud server or other device remotely connected to a display device present in a survey vehicle or other on-site location, while step 532 is performed on a local or remote display device. In some embodiments, at least parts of some of the steps prior to step 532 may also be performed locally, for example using a scripting language such as Javascript. In cases where there is no connection to the cloud (due to poor cell coverage, for example) the survey can still be conducted and the results still seen by the user in real time.

Tracking Changes in Emission Rates Over Time

In some embodiments, a sequence of measurements and associated analyses as described herein are used to track emission rates over time. The description below focuses primarily on identifying and characterizing natural gas leaks in an under- and above-ground transmission and distribution system, but the exemplary sequential analysis approaches described below may be applied to other systems in which understanding heterogeneous ground level emissions is useful. The end user of such a system may be an individual interested in gas leak detection and emissions quantification.

The ability to quantify the emissions rate of fugitive natural gas leaks on a distribution or transmission system is potentially useful to the industry in several ways. For example, the emission rate of a given leak (or leaking segment of pipeline) may be one factor affecting the hazard posed by the leak. Under certain circumstances, leaks with larger emissions rates may result in a high probability of gas migrating into a confined space, thereby presenting an explosion hazard. Additionally, when not burned, methane is a potent greenhouse gas (GHG). Gas utilities are interested in surveying their transmission and distribution systems to quantifying the emissions rates of individual leak and pipe segments so as to decide how to direct limited resources to repair and upgrade their systems to achieve maximal benefit in terms of improved safety and reduced GHG emissions.

Beyond the ability to quantify fugitive emissions rates at a given moment in time, the ability to track changes in the emissions rates of leaks or pipe segments also provides useful information. For example, slow trends in emissions rates may be used to identify and track the progression of leaks caused by corrosion. In some systems, especially those with significant amounts of old cast-iron pipes, fugitive leaks can either appear abruptly, or have a sudden and large increase in emissions rates as a result of acute outside forces damage, such as that caused by frost heave as the frozen ground swells and dislodges a pipe or joint. In some cities in the northeastern United States, frost-heave is responsible for dozens of catastrophic distribution integrity failures each winter. Measurements collected with methane sensors mounted on vehicles provide the ability to rapidly and repeatedly survey a distribution pipeline network to identify new leaks and mitigate the hazard they present as soon as possible after they occur.

Measuring the emission rate(s) of a leak is a challenging task. Direct methods, such as those where the concentration is measured inside a large bag or tent that attempts to capture over all the emission points, or those that require excavation, are time- and cost-intensive and may be impractical for surveying large distribution networks. Mobile methods that measure the downwind concentration of methane in a gas plume at one or more vertical locations can be used to estimate the emission rate. At the same time, the single-measurement precision of such methods can be noisy, with the best achievable precision being governed by the stochastic behavior of plume propagation in a locally-divergent turbulent atmosphere.

The emission rates of individual leaks may vary due to factors that don't represent changes in the severity of the damage to pipe. One such factor is pipeline pressure: for a given size hole in a pipe, the leak rate will vary directly with the pressure in the pipe. Furthermore, the rate at which gas escapes into the atmosphere may exhibit variability due to, e.g., changes in surface permeability driven by diurnal or seasonal temperature changes, by the moisture content of the soil, and/or by other factors.

Exemplary systems/methods described herein may automatically account for such inherent sources of variability occurring on a similar time scale as the interval between measurements, and allow calculation of a probability or confidence level with which a given measurement or group of measurements represents a change in emissions rate indicative of a possible change in the state of health of a leaking pipe.

In some embodiments, changes in the emission rate of a gas emission source are detected by performing sequential, time-series measurements of gas concentrations away from the source. The emission rate, or another quantity that is a statistical proxy for emission rate, of the gas emission source is measured for each of a plurality of measurement runs performed along the same or similar paths. In some embodiments, the measurement runs use a survey protocol that minimizes variability (noise) in the measurement due to factors such as the distance between the leak at the measurement location. The survey protocol may include driving the same lanes of the street at the same time of day on each subsequent round of measurements. A graphical user interface may be used to receive user input indicative of the geospatial location (e.g. identity of a current lane) of the vehicle at particular times, and to provide an operator with indicators of a recommended choice of lane at a current geospatial location, and/or indicators of real times associated with the current geospatial location during one or more prior measurement runs.

In post-acquisition data processing, different measurements are grouped together when determined to be likely to have originated from the same source. Such grouping allows associating each of the measurements with a given source. The measured emission rates or measured values of a statistical proxy are corrected to account for variability in the measurement caused by changes in conditions between measurements. The probability that a significant change in emissions rate occurred between any two groups of measurements that are sequential in time is quantified. An output is then generated that reports whether a change occurred, and, if a change did occur, at what time or within which range of times the change occurred, and a measure of the probability or statistical confidence that the change occurred.

In some embodiments, the measurements are taken onboard a moving vehicle recording geospatial position and time and primary gas concentration measured at one or more vertical measurement locations. The emission rate quantification technique may incorporate a gas flux chamber (an enclosure made of plastic or other impervious material placed over a suspected leak location) combined with a gas concentration detection apparatus. The emission rate quantification technique may also incorporate a tracer release method whereby tracer gas of known concentration is released at a known rate in close spatial proximity to an emission source with a different chemical composition than the tracer gas and having an unknown emission rate; the dispersion of the tracer gas concentration may be quantified to calculate the unknown emission rate of the source of interest from concentration measurements of the source gas.

In some embodiments, the emission rate measurement technique incorporates a mobile flux plane as described above. In some embodiments, a peak primary concentration enhancement above an ambient background level is used as an indicator or statistical proxy for emission rate. In some embodiments, a line flux defined as the integral of the product of the concentration enhancement and wind speed lateral to the path of the vehicle with respect to the distance traveled through a cross-section of the gas plume may be used as a statistical proxy for emission rate.

In some embodiments, measurements may be clustered according to the proximity of their associated measurement locations to each other, and an estimated source position may be taken as a representative position derived from the cluster. Such a representative position may be a location determined by spatially averaging the clustered locations. Associating measurements that likely originate from the same candidate source may be performed using a geo-spatial density clustering algorithm such as DBSCAN. In some embodiments, associating measurements with a candidate source may include associating all measurements taken within a given radius of an estimated source location.

In some embodiments, correcting the measured emission rates or values of the statistical proxy is accomplished using an atmospheric transport model and measurements of one or more of wind speed, air temperature, cloud cover fraction, cloud height, longwave radiation, shortwave radiation, ground surface temperature, or conductive heat flux through the ground. In some embodiments, correcting the measured emission rates or values of the statistical proxy is accomplished by normalizing the measured values by the average value of the emission rates or statistical proxy values measured for a set measurements made for one or more other sources in a window of time around which the measurement for the source interest is made. In some embodiments, correcting the measured emission rates or values of the statistical proxy is accomplished according to an empirically-determined relationship between the expectation value of the emission rates or values of the statistical proxy for a given source strength, measured wind speed, and range of possible downwind distances between the source and measurement locations.

In some embodiments, at least four measurements are available. The statistical test to be applied may be a Komolgorov-Smirnov test applied between groups of measurements that are sequential in time with each subset consisting of at least two measurements. Performing such a comparison may include comparing all possible combinations of two subsets of sequential measurements, each containing at least two sequential measurements. In some embodiments, subsets of measurements may be binned by wind direction, and statistical change analysis is performed independently on each of the binned subsets. The statistical test to be applied may make use of theoretical or empirically-estimated probability distributions of emission rate or emission-rate proxy over a range of leak rates, distances from the source, and measurement conditions combined with a prior probability distribution of leak rates. In some embodiments, a significant change may be determined to have occurred if the p-value of the statistical test for at least one pair of measurement sets being tested meets a threshold condition. In particular, a significant change may be determined to have occurred between the pair of measurement subsets with the smallest p-value that meets the threshold condition. The probability that a change occurred may be calculated using the same p-value, which represents that probability that the two measurement subsets were drawn from different underlying distributions. The time at which the change occurred may be defined by the earliest time range separating two subsets whose output of the statistical test meets the threshold condition.

Exemplary change-detection methods described below attempt to address the large variability in measured amplitudes that may be observed even in the absence of leak rate changes. Large variations in measured amplitudes for a fixed leak rate may be due a number of factors, including variability in atmospheric conditions, and local spatial variations in plume concentrations. In some instances, localized amplitudes detected from an unchanged leak source at similar locations were observed to vary by as much as a factor of ten between different measurement runs. Identifying leak rate changes can be particularly challenging in the context of such large variations between different measurement runs performed for an unchanging leak.

In some embodiments, identifying a change in emission rate may include quantifying an emission rate before and after a time boundary, and comparing the change in the emission rate estimates across the time boundary to a predetermined threshold. Such an approach may effectively use the mean and standard deviations of the two measurement value distributions. The measurement values may include amplitudes, values of flux, or values of statistical proxies for flux and/or amplitude such as amplitude or line integral results computed as described below. Such an approach may be particularly effective in the presence of relatively low variations in detected amplitudes between different measurement runs in the absence of emission rate changes, and/or if relatively high numbers (e.g. tens or hundreds) of measurement data points are available for a given emission source. Under such conditions, the intra-collection variabilities (e.g. the standard deviations or error bars of the measurements) may be lower than the inter-collection distances (e.g. differences between the means or other representative values). In other words, such an approach may work well if the error bars for the two collections of measurement values do not overlap substantially.

In some embodiments, determining that a significant change in emission rate has occurred may be performed without explicitly quantifying emission rates, by determining whether measurement values before and after a time boundary fit substantially different statistical models (distributions), each model corresponding to a different emission rate. Such an approach may effectively use all data points in each distribution, even if such a distribution is somewhat sparsely populated, rather than rely solely on global collection parameters such as mean and standard deviation. Such an approach may be particularly preferred when the error bars for the two collections of measurement values may overlap substantially, for example due to relatively high variations in detected amplitudes for a given emission rate, and/or if only relatively low numbers (e.g. single digit numbers) of measurement data points are available for a given leak.

Figure 26:
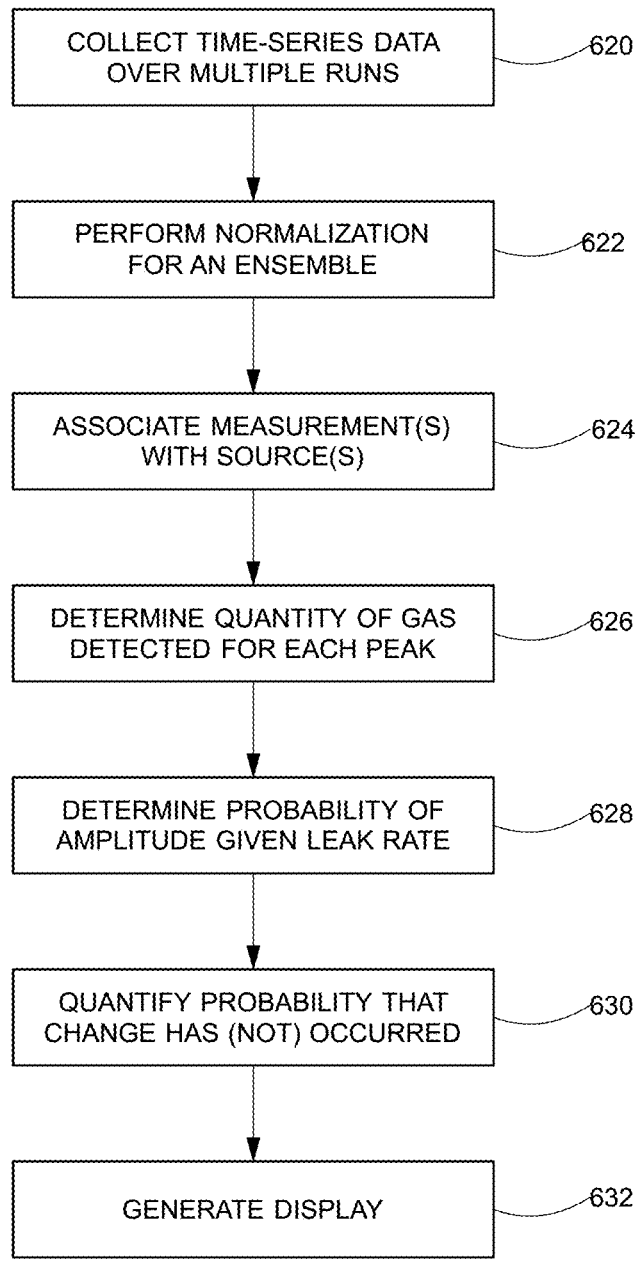
FIG. 26 shows an exemplary sequence of steps performed by at least one processor to track changes in measured emission rates over time according to some embodiments of the present invention.

FIG. 26 shows an exemplary sequence of steps performed by at least one processor to track changes in measured emission rates over time according to some embodiments of the present invention. In a step 620, concentration data as described above are recorded over multiple runs performed over the same or closely-spaced pathways to yield time-series data characterizing one or more natural gas emission sources. Step 620 may include taking measures to minimize variability in survey conditions between runs as described below. Survey conditions may include precise location/trajectory (including choice of lane for multi-lane roadways), time of day, and/or atmospheric conditions. In a step 622, a data normalization procedure is performed using data from an ensemble of leaks as described below. In a step 624, measured amplitudes are associated with each other and/or with emission source(s) and their geospatial locations.

In some embodiments, the process proceeds directly to a step 630 below, which may be performed using normalized amplitudes. In some embodiments, the process proceeds to a step 626, in which a quantity of gas detected for each detected concentration peak is determined, a step which may include calculating a flux and/or line integral as described below. In some embodiments, the process then proceeds directly to the step 630 below. In some embodiments, the process proceeds to a step 628, in which a set of probabilities of detecting observed amplitudes given certain emission rates are determined as described below. Such probabilities may provide useful information, even though computing such probabilities may not be necessary in order to statistically detect whether or not two groups of measurements are drawn from the same probability distribution. In a step 630, a set of probabilities that changes in emission rates have (or have not) occurred are quantified. In a step 632, display data representing evaluated changes in emission rates are generated and transmitted to one or more display devices for display.

In some embodiments, determining an emissions rate indicator or quantifying emissions attributed to a leak (step 626 in FIG. 26) comprises summing a set of measured concentration amplitudes over a surface or 1-D trajectory of interest. Such a summation may depend on the geometry of the sensor arrangement used to collect data. Collecting time-series data using moving vehicles may use various sensor configurations, including a multi-inlet configuration with inlets arranged vertically on a mast, a multi-inlet configuration with inlets arranged horizontally on a vehicle bumper or other vehicle-mounted structure, or a single-inlet configuration with an inlet disposed on a mast, bumper, or other vehicle structure, or on a device otherwise carried by the vehicle. The description below focuses on two exemplary configurations suitable for performing measurements with methane sensors mounted on moving vehicles: a multi-inlet configuration using a vertical mast mounted on a moving vehicle, and a single-inlet configuration.

Figure 27:
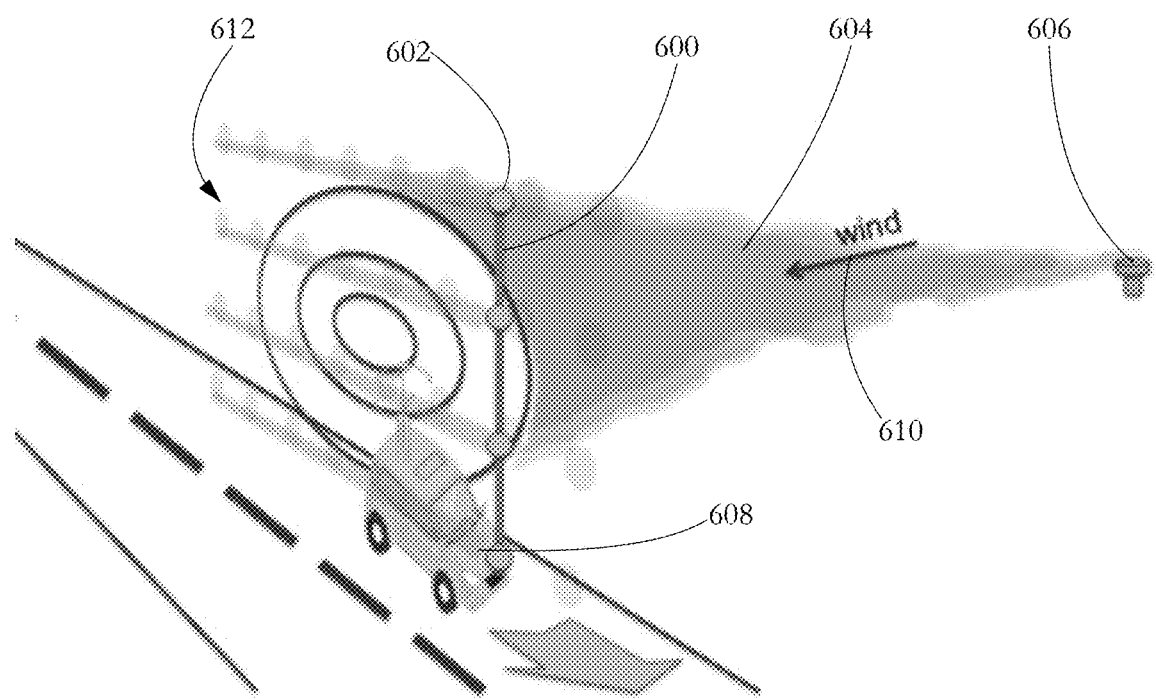
FIG. 27 illustrates an exemplary geometry of a 2-D integral used to estimate a flux of methane passing through a 2-D surface swept out by a collection mast according to some embodiments of the present invention.

FIG. 27 illustrates schematically a vertical mast 600 which includes multiple vertically-spaced inlet (measurement) ports 602, each sampling concentration independently and each corresponding to a measurement channel. In a single-inlet configuration, a single active inlet port is used to collect data. The mast is attached to a vehicle as described above, and driven through a gas plume originating at gas emission source. In some embodiments, the arrangement of the measurement ports can be changed using a servo system to toggle between two or more pre-determined measurement port configurations, or to a configuration where one or more of the measurement ports moves dynamically during a measurement run. In some embodiments, a configuration of measurement ports can include vertically separated measurement ports and one or more additional low-height measurement ports near ground level that can be used specifically to identify on-road below-the-vehicle leaks that are not sufficiently offset from the vehicle's axis of motion. In some embodiments, each of a plurality of inlets may be coupled to a dedicated corresponding spectrometer as described above. In some embodiments, a common spectrometer may be fluidically coupled to multiple inlet ports through a system including valves and long tubes forming gas storage chambers; in such a system, gas collected through multiple ports may be collected in parallel into corresponding gas storage chambers, and then released serially into the spectrometer to provide a delayed playback of the gas collection process.

Consider a method of sampling methane concentration using multiple inlets 602 arranged vertically on a mast 600 which is driven through a downwind transect of a gas plume 604 originating at a localized source 606, as illustrated in FIG. 27. Measurements of instantaneous wind speed and direction are made simultaneously using a wind sensor mounted onto a vehicle 608. The prevailing wind direction during the sampling period is shown at 610.

A flux-plane technique may be used to determine an estimate the flux of methane passing through a two-dimensional surface 612 swept out by the mast 600 according to $$Q = \int_A k(C(x,y) - C_0) \overrightarrow{u(x,y)} \cdot \hat{n} dA \qquad (7)$$

wherein $C(x,y)$ is the concentration at a given point in space on the surface A (shown at 612 in FIG. 27), $C_0$ is the background concentration of the target gas, $\overrightarrow{u(x,y)}$ is the velocity of the gas, and n is the normal to the surface element dA. The constant k may be used to convert volumetric flow in $m^3/s$ to moles/s, such that the unit of emission rate Q is, for example, moles/second. A flux computed according to eq. (7) provides an indicator of the corresponding emission rate, and may be substantially equal to the emission rate if the entire gas plume is captured by the swept surface. Eq. (7) implies that the transect is made at an instant in time, an assumption that is generally valid so long as the transect is performed at a driving speed that is fast compared to the component of wind speed normal to the two-dimensional surface. In some embodiments, it was found that the single-measurement precision of such a technique is limited by the nature of plume propagation in the atmosphere. Due to local divergence of the turbulence field, an individual measurement can result in emissions rate estimates that vary upward or downward from the true value by a factor of 2 to 3 or more, depending on the specific conditions of the measurement.

Figure 28:
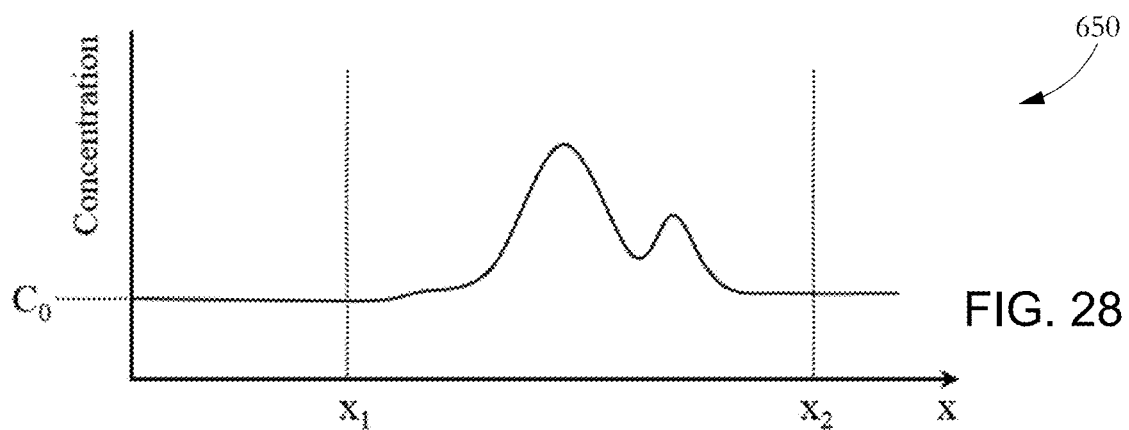
FIG. 28 illustrates an exemplary geometry of a line integral used to estimate a line flux according to some embodiments of the present invention.

In some embodiments, the downwind concentration enhancement may be measured at a single vertical measurement location, for example using a mast having a single active inlet. The concentration enhancement may be measured as peak height above the ambient background level, or as a line flux according to $$F = \int_{x_1}^{x_2} k(C(x) - C_0) \overrightarrow{u(x)} \cdot \hat{z} dx \qquad (8)$$

where F is the line flux, $\hat{z}$ is the horizontal unit vector perpendicular to the direction of travel, and the range of integration $x_1 < x < x_2$ is sufficiently large so as to cover the full extent of the plume transect. FIG. 28 illustrates at 650 the geometry of the integral of eq. (8) for an exemplary plume transect. As above, the line flux may be used as an indicator of the corresponding emission rate. The line flux of eq. (8) can be expected to be proportional to the 2-D flux of eq. (7). In some embodiments, the constant k may be chosen so that, on average, a result of using eq. (8) for a single-inlet system matches a 2-D flux computed using eq. (7) for a multi-inlet system using a mast. In an exemplary implementation, we found that a suitable value for k may be between 1 and 2 square meters, for example about 1.5 square meters.

In some embodiments, measurements of peak amplitude or line flux (eq. (8)) were observed to tend to exhibit larger single-measurement variability for a given fixed leak rate compared to those made with a flux plane (eq. (7)). In the case of amplitude-based measurements, the spread of single-measurement values can, however, be misleading as a metric of comparison to the flux-plane technique. In particular, the single-inlet technique can be particularly useful if P(a|Q), the function describing the probability of observing an amplitude a given a leak emissions rate Q, follows a log-normal distribution:

$$P(a \mid Q) = \frac{1}{a\sigma\sqrt{2\pi}} e^{\frac{-(\ln a - \mu)^2}{2\sigma^2}} \qquad (9)$$

which is a function of the amplitude a where exp(σ), the geometric standard deviation, is a constant, and where exp(μ) is the geometric mean of the distribution, where μ=μ(Q) is a logarithmic function of Q.

Observed differences in measured concentrations around a location of interest can reflect in principle two main causes: changes in the emission rate(s) of the relevant source(s), and changes in atmospheric, location, and/or other measurement conditions characterizing the different measurement runs. In some embodiments, a number of techniques are employed to minimize sampling variability as described below, so as to increase the relative impact of changes in source emission rates on detected differences in measured concentrations (relative to sampling variability). The better the single-measurement precision of a given technique, the easier it will be to detect significant changes in emissions rates. The ability of a single measurement to constrain the emissions of the source is reflected in the forward probability distribution, P(a|Q), which is in practice a function not only of Q but also of conditions, i.e. P(a|Q) =P(a|Q, $\vec{C}$) with the conditions represented by the vector $\vec{C}$. Such conditions can include one or more of the wind speed, the degree of atmospheric stability, the distance between the leak and the measurement location, and other factors such as local features of the landscape that can contribute to gas plume dispersion. The single measurement precision decreases the larger the range of $\vec{C}$ that is to be considered. Thus, detecting changes from one measurement to the next will be more precise when $\vec{C}$ can be held as constant as possible from one measurement to the next, or if the effects of variable $\vec{C}$ can somehow accounted for and removed. The description below focuses on two approaches for accomplishing this task. In one approach, the survey protocol is constrained so as to minimize the variability in conditions. In another approach, data processing is used to account for changes in measurement run conditions.

In some embodiments, P(a|Q,$\vec{C}$) is dependent at least to some extent on the distance between the leak and the measurement location. In the context of monitoring a distribution network where the gas delivery infrastructure is under or near the road, the variation in the distance between the source and the measurement location may be minimized by using the same driving pattern, and in particular the same sequence of roads and choices of lanes. For a given wind direction, closely replicating driving patterns should minimize variability in location where the plume transect is made.

Figure 29:
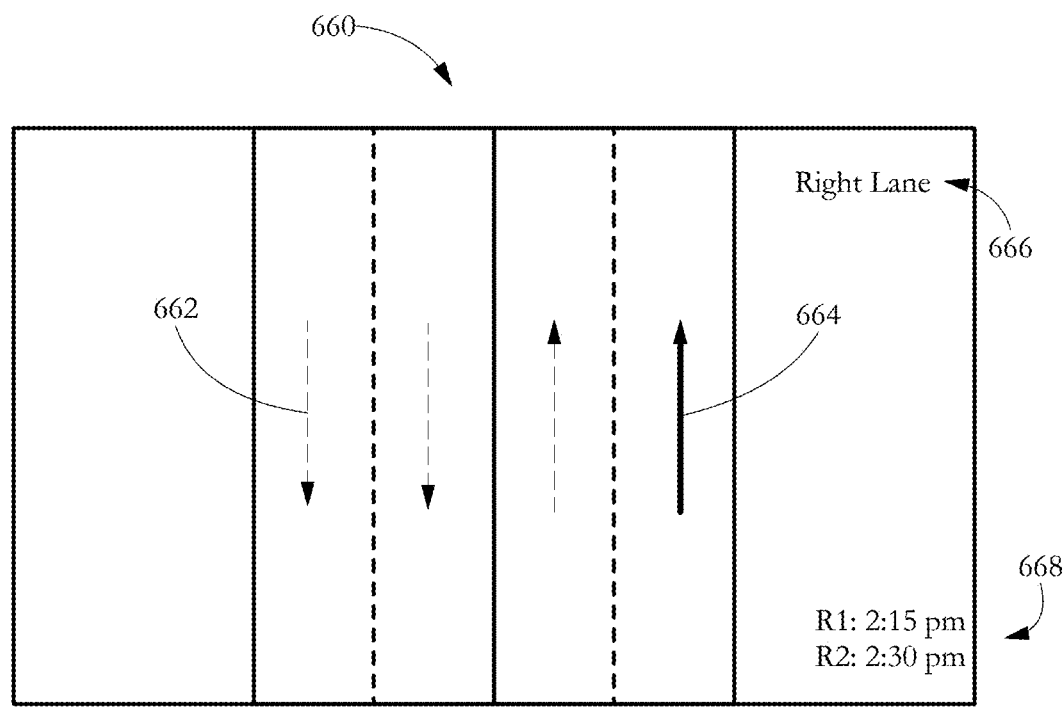
FIG. 29 shows a part of a graphical user interface used to display a roadway lane selection during a selected run of a sequence of temporally-spaced measurement runs according to some embodiments of the present invention.

In some embodiments, the user interface guiding the measurement operator is configured to display a recommended geospatially-referenced path including a visual indicator of a recommended street and, or multi-lane roadways, a visual indicator of a recommended lane. In some embodiments, such a user interface may also display a real time (time of day) characterizing a prior measurement run, to allow an operator to perform subsequent measurement runs at the same or closely-spaced time on a subsequent day. FIG. 29 shows an exemplary map display 660 including lane indicators 662 for multiple lanes of a current road that the measurement vehicle is traveling on, and a selected (recommended) lane indicator 664 identifying one of the lanes as a selected lane for the current road and current measurement run. The exemplary illustrated lane indicator 664 comprises an arrow overlaid onto a displayed map representation of the corresponding roadway. In some embodiments, a lane indicator may include another lane indicator, such as a textual lane indicator 666 (e.g. "Right lane," "Middle lane," or "Left lane" text) overlaid onto or displayed in association with a map display of the current roadway. A time-of-day indicator 668 indicates the time(s) of day that correspond to the current location during one or more previous measurement runs. The display of FIG. 29 may form part of a user interface such as the exemplary one illustrated with reference to FIGS. 4-7 and/or 24.

In some embodiments, a selected lane indicator is generated for each measurement run independently of location data acquired during prior measurement runs. For example, the right-most lane (or another predetermined lane) on any multi-lane road may be automatically selected in order to suggest the use of the right-most lane for all measurement runs, independently of past trajectories. In some embodiments, a selected lane indicator is generated for each measurement run according to location data acquired during prior measurement runs. Such location data may include geospatial data (e.g. GPS data), and/or manually-entered indicators of lanes employed on given roadways for particular past measurement runs. During each run, a real time (time-of-day and optionally date) may also be associated with each geospatial location along the run, and stored in a database for retrieval and display during future measurement runs along that geospatial location.

In some embodiments, the lanes of a given roadway may be identified and associated with geospatial (e.g. GPS) coordinates offline, by analyzing satellite/aerial map images which include associations between map and geospatial coordinates. In some embodiments, a given lane of a roadway may be identified and associated with geospatial coordinates during a measurement run, for example by receiving from an operator a current lane indicator (e.g. a textual input such as R (right), L (left) or M (middle)), entered on a graphical user interface during a measurement run, and associating the entered current lane indicator with the current roadway identified by the system's geospatial navigation device.

If the wind direction changes between measurements of a source that is located substantially upwind of the measurement location, the gas plume will likely be detected at a different location along the survey track and the distance between the leak and the measurement location will change. In some embodiments, such changes in detection distance and wind direction may be addressed by separating recorded concentration measurements into bins corresponding to different mean wind directions, and by conducting a time-series change analysis for each wind-direction bin independently. Depending on the range of wind directions encountered, following such a procedure could in theory result in the change-detection technique being less sensitive. In some embodiments, we found that the bias due to distance from the leak does not substantially affect the results for leaks detected at distances within 75-100 feet of the source location. Thus, it is often not particularly helpful or necessary to bin by wind direction when applying a time series change analysis as described herein in most urban survey situations. In some embodiments, binning by wind direction may be performed for leaks determined to be situated at distances exceeding a predetermined threshold (e.g. 50, 75 or 100 feet), while binning is not performed at leaks determined to be closer than the predetermined threshold.

In some embodiments, a normalization process (step 622 in FIG. 26) may be performed in order to minimize the effects on the change-detection analysis due to variability on the width of $P(a|Q,\vec{C})$ caused by changing atmospheric conditions. In particular, in some embodiments it was found to be effective to normalize each individual amplitude measurement by the mean amplitude for all emissions (leaks) measured across an ensemble of leaks taken over a span of time surrounding the measurement of the leak of interest. Such a normalization step is consonant with the prediction that a given atmospheric condition is likely to result in a general enhancement or diminishment of the signatures of all leaks in a similar way. When combined with a survey protocol that remains the same as much as possible from one monitoring cycle to the next, for a given normalization time window the ensemble of leaks being used to calculate the normalizing factor should be about the same from one measurement to the next. In some embodiments, the span of time used to calculate the normalization is chosen to be large enough that individual leak signatures do not significantly impact the result, but reflect the time-scale over which significant changes in atmospheric variability take place. In some embodiments, it was found that an effective time span ranges ±15 minutes about time of the measurement of interest to ±2 hours, with a window of ±30 minutes in preferred embodiments.

In some embodiments, a number of steps as described below may be used to associate given concentration measurements with a particular emissions source (step 628 in FIG. 26). Such an association may be of particular interest in areas with multiple emissions sources in relatively close proximity, where more than one source could in principle be responsible for a detected concentration peak. In some embodiments, such an association is performed before determining changes in the emissions rate for a particular source amongst observations of many sources.

In some embodiments, associating a given measurement with an emissions source is performed by using one or more spatial clustering algorithms, such as the density clustering algorithm DBSCAN. Given a set of points in a feature space, such a density clustering algorithm groups together points that are closely spaced together, and marks as outliers points that lie alone in low-density areas of the space. Each point may represent a geospatially-referenced location, such as a latitude/longitude coordinate pair on a map, where peak concentrations were detected. Grouped (non-outlier) points may be core points and reachable points. A point is a core point if at least a predetermined minimum number of points are within a predetermined distance of the point; such nearby points are said to be directly reachable from the point of interest. A more distant point is reachable from the original point if there is a path formed between the two points through directly-reachable connections. For a given core point, a cluster is formed by all points (core and non-core) reachable from the given core point. All points not reachable from at least another point are deemed outliers.

In some embodiments, such a clustering method uses as input two parameters: a physical distance scale expected for a cluster of observations tracing back to a single leak, and a minimum number of measurements needed to form a cluster. In some embodiments, it was found that a distance scale between 10 and 50 meters is appropriate for this application, with a choice of 20 or 30 meters in preferred embodiments. The minimum number of points may be set to equal the minimum number of measurements in each of the two distributions to be compared. In some embodiments, best results were achieved for choices ranging between 2 and 5, with a choice of 3 in preferred embodiments.

In some embodiments, the probability that a change in emission rate has (or has not) occurred given a set of time-series measurements is quantified as described below. Consider two distributions of measured line-fluxes or amplitudes associated with a source and containing two or more values each. In some embodiments, a statistical test such as a Kolmogorov-Smirnov (KS) test is applied to the two distributions in order to determine a probability that a change in emission rate has occurred. The KS test is a non-parametric test that can be used to quantify the probability that two distributions were drawn from the same underlying distribution, without requiring knowledge of the underlying distribution itself. The KS statistic quantifies a distance between an empirical distribution function of the sample of interest, and a cumulative distribution function of a reference distribution. When used to compare two measured distributions, the test statistic is the maximum distance between the two empirical cumulative distribution functions. The power of the test to reject the null hypothesis increases as the number of samples in each empirical distribution increases. In particular, if there is a high probability that the two distributions originated from the same underlying distribution, that means that no significant change in emission rate is considered to have occurred.

In some embodiments, given a set of N sequential measurements, $\{a_1, \ldots, a_N\}$ associated with a given emissions source, we can compare every possible pair of subsets containing at least two sequential observations using the KS test. For each pair of sets k comprising $\{a_1, \ldots a_k\}$, $\{a_{k+1}, \ldots a_N\}$, $2<k<N-2$, we calculate a p-value for each pair, $p_k$. For example, for an exemplary sequence of 8 measurements, we can consider the pairs of sets formed by the first two and the next six measurements, the first three and the next five, and so on until the first six and the last two, and we calculate a p-value for each pair of sets. A change in emissions rate may be considered to have occurred if any of the $p_k$ meets a threshold condition $P_k<P_{thresh}$. In some embodiments, it was found that values of $p_{thresh}$ ranging between 0.100 and 0.001 were successful at detecting significant changes when comparing sets of measured amplitudes for leaks on a cast iron distribution system, with $p_{thresh}$ of about 0.01 being preferred. In some embodiments, a change in emissions rate is said to have occurred in the time interval between measurements k and k+1 for the first $p_k$ that meets the threshold condition.

In some embodiments, a detected change in emission rate may be represented graphically by reporting a geospatially-referenced location (e.g. street address) corresponding to the location where we think the leak that underwent the change occurred. Reports may be generated as soon as the change is detected, and the time when the change occurred may indicated by the date/time of the report. In some embodiments, a display of a bubble or other emission change indicator may be generated on a map. The graphical size of the emission change indicator may be proportional to the change in emission rate, or the probability that a change in emission rate above a predetermined threshold has occurred. A time or time range when the change occurred may be displayed as an annotation or call-out. In some embodiments, emission rate change information may also be displayed in a table that includes the information above, indexed by latitude and longitude and/or street address.

Multi-Variable Leak Ranking Model(s)

In some embodiments, a risk score or ranking is assigned to a leak indication or group of leak indications, indicating a hazard level of the association leak(s). The terms ranking and grading are used herein to refer to both unique rankings and non-unique rankings. A unique ranking is one in which no two elements may share the same ranking; for example, ten leaks ranked from one to ten. A non-unique ranking is one in which two or more elements may share the same ranking; for example, ten leaks ranked by grade from A to F, or levels 1 to 3.

In one approach, determination of an individual leak's level of hazard is done by a grading procedure at the time the leak is found. For underground leaks, a probe placed underground at the location of the leak may be used to measure the gas concentration. An example of such a classification scheme is described below. As a skilled artisan appreciates, LEL denotes a Lower Explosive Limit, often considered to be the same as a Lower Flammability Limit (LFL), representing a concentration below which a gas mixture is too lean to burn. For example, methane has an LEL of 5%, and an atmosphere containing less than 5% methane will generally not explode even in the presence of a source of ignition.

| | |
|---|---|
| Grade 1 A leak that represents an existing or probable hazard to persons or property, and requires immediate repair or continuous action until the conditions are no longer hazardous | Any underground concentration reading within 5 feet of an outside wall. Underground concentration reading of greater than 80% LEL in a confined space, Any leak that can be seen, heard, or felt, and which is in a location that may endanger the general public or property. |
| Grade 2 A leak that is recognized as being non-hazardous at the time of detection, but justifies scheduled repair based on probable future hazard. | Underground concentration reading of 20-79% LEL in a confined space. Underground concentration reading greater than 20% gas within 30 feet of a building. |
| Grade 3 A leak that is non-hazardous at the time of detection and can be reasonably expected to remain non-hazardous | Any reading outside curb or shoulder more than 5 feet from a building. Leak from above-ground component that cannot vent into a confined space. Any leak not classified as Grade 1 or Grade 2. |

In some embodiments, if the grading criteria are based on a procedure where the leak is measured at its source, it may not be feasible or desirable to completely determine a leak grade based solely on a vehicle measurement in the downwind natural gas plume. The exemplary systems and methods described below allow using vehicle measurements to prioritize leak indications that are more likely to be associated with a hazardous leak (Grade 1 and Grade 2) and to minimize the reporting of indications that are associated with a non-hazardous leak (Grade 3).

Figure 30:
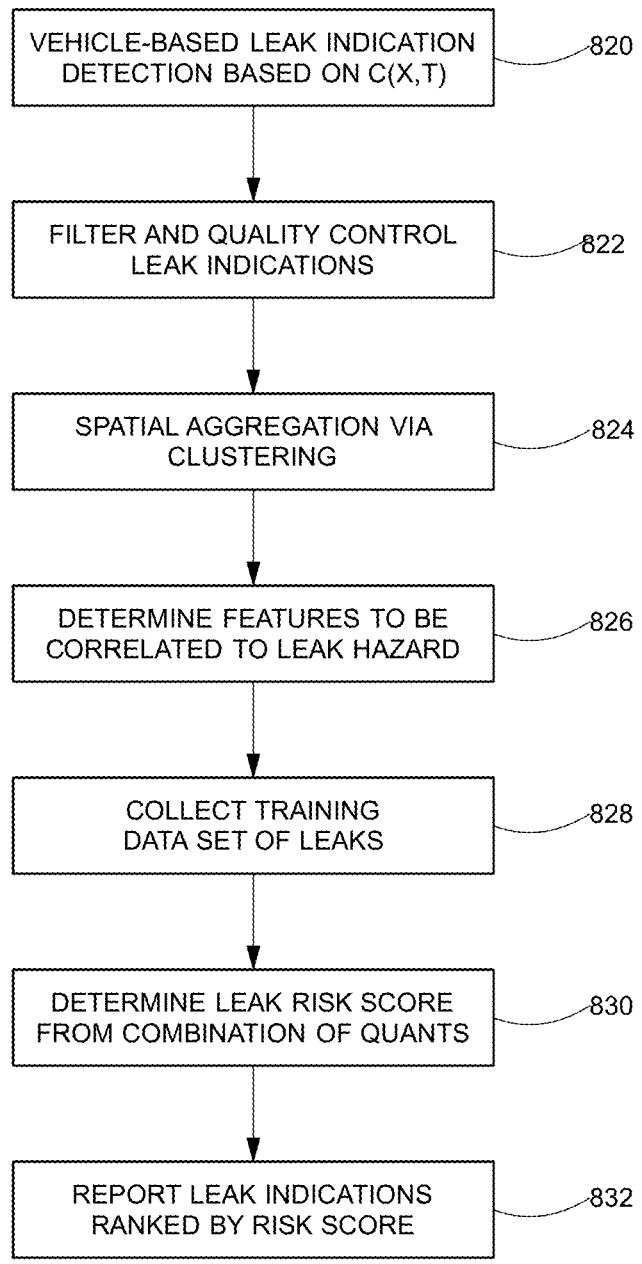
FIG. 30 shows an exemplary sequence of steps performed to rank leak indications by risk according to some embodiments of the present invention.

FIG. 30 shows a sequence of steps performed according to some embodiments of the present invention. As will be apparent from the description below, at least some of the steps described below may be performed using machine learning techniques, which involve using statistical methods to give computers the ability to improve performance on specific tasks without explicit programming. In particular, machine learning techniques allow building a model using sample inputs so as to match training data, as described below.

In a step 820, potential leak indications are detected automatically using a vehicle-based survey performing measurement of concentrations $C(x, t)$, as described above. In a step 822, filtering and quality control are performed on the potential leak indications, as described below. An exemplary method of filtering and/or quality control may include applying a variable- and/or high-background filter as described in US Patent Publication No. 2016/0011069 A1, published Jan. 14, 2016, entitled "Gas leak detection and event selection based on spatial concentration variability and other event properties," which is incorporated herein by reference. Another exemplary method may include evaluating inter-peak distances and/or peak-overlap conditions as described in U.S. Pat. No. 9,823,231 B1, issued Nov. 21, 2017, entitled "Systems and Methods for Assembling a Collection of Peaks Characterizing a Gas Leak Source and Selecting Representative Peaks for Display," which is incorporated herein by reference. In a step 824, spatial aggregation is performed on the leak indications using clustering techniques, to generate sets of spatially-aggregated leak indications (clusters).

In a step 826, a set of leak indication features to be correlated to leak hazard is determined. In some embodiments, step 826 includes performing a statistical analysis on the aggregated groups of leak indications, spatially associating each aggregated group of leak indications with nearby natural gas distribution infrastructure as identified by plats or other geospatially-referenced position data, and determining whether leak locations are within predefined high-consequence areas (HCAs). In a step 828, a training data set of leaks associated with each aggregated group of leak indications is collected. In a step 830, a leak-risk score model is formulated based on a linear and/or non-linear combination of quantities derived from the spatially-aggregated data and associated distribution infrastructure, so that the leak-risk score best describes the training data. In a step 832, the leak-risk score (hazard level) model is applied to new data, and aggregated leak indications are reported as ranked by risk score.

In some embodiments, the spatial aggregation step 824 may include applying one or more machine-learning algorithms, such as DBSCAN and/or a Markov clustering algorithm, as described below, to input data. Spatial clustering associates indications that are nearby in space and likely associated with a localized natural gas emission source. This goal of this process is to combine data from multiple plume detections to produce consolidated indications that provide the best possible prediction of leak location, emission rate and/or attribution. Two exemplary machine learning algorithms suitable for identifying spatial clusters of plume detections according to some embodiments are described below: (1) DBSCAN and (2) Markov Clustering.

DBSCAN is an acronym for Density Based Spatial Clustering of Applications with Noise. DBSCAN is based on the concept that clusters are dense groupings of points collocated in space. There are two input parameters to the algorithm: maximum distance scale, and minimum number of points per cluster. The algorithm randomly and recursively examines points in the data set searching for groupings of data that meet the input criteria. Once these basic groups have been identified, the spatial extent of each cluster is expanded to each remaining point in the data set until the criteria set by maximum distance scale is no longer satisfied. When this process is complete the data will be categorized into spatial clusters, while some points may be excluded from the dataset because they are outliers which do not fit into any of the identified groups.

Markov clustering is a graph based clustering method that uses a random walk approach to identify associated points in the input data set. The inputs to the algorithm are a non-direction graph network for the input data points, an expansion parameter, and an inflation parameter. A non-directional graph provides information about the relationship between all points in the input data. This kind of graph consists of the location of all nodes (data points) and the edges (connections between the nodes) subject to requirements that the edges are limited to a certain distance and permit bi-directional links. Random walks are then initialized for each node in the graph travelling along the edges and tracked as they move through the network. The expansion coefficient controls the length of the random walks. A larger expansion parameter corresponds to computing random walks of higher length, which means random walks with many steps. The inflation parameter controls the probabilities associated with the collection of random walks departing from one particular node, by favoring more probable walks over less probable walks. Increasing this parameter has increases the granularity or tightness of clusters.

In some embodiments, the input parameters for the clustering algorithm can be determined in several different ways. The distance scale parameter depends on the expected spatial separation between leaks in the survey area, and the density of survey transects. The distance scale parameter can be defined empirically based on data from representative surveys or determined from known distances between infrastructure sources. The distance scale parameter can also be determined from GIS data which encodes the location of individual infrastructure components that may leak. For example, in the application of monitoring leaks on well heads at a natural gas production facility, the spacing of well heads on the well pad may be used define the distance scale for the clustering algorithm.

Other clustering algorithms can take advantage not only of the location of the plume where the vehicle transected it, but the wind direction with respect to the ground at this time and location. This additional information may provide little benefit to the spatial aggregation algorithm when the wind is constant or the leaks are close to the vehicle, but can improve the performance of the algorithm when wind direction is variable and the leak is offset from the path of the vehicle. Consider the detection of a single leak during two measurement runs, for two different wind directions. The two indications are separated by a large distance along the path of the vehicle due to the difference in the downwind path of the plume; by incorporating both plume detection location and wind direction into the aggregation algorithm, the performance of the algorithm can be improved, both from the standpoint of combining two indicators from the same leak that would otherwise be rejected by an aggregation algorithm that employs only spatial information, and/or by helping to separate the indications from two leaks that would otherwise be combined. One way to incorporate wind direction into the aggregation algorithm is to further restrict the population of indications to those indications that occurred for a specific range of wind directions; each of these sub-populations can be processed using DBScan or Markov clustering as described above. The results may be presented separately or on the same map.

In some embodiments, the statistical analysis step 826 determines a set of features to be used to model the risk score. Exemplary features may include one or more of the following: maximum, minimum, mean, and median CH4/amplitude of the aggregated leak indications; estimated leak flow rate, determined from a Bayesian average of leak indications in a cluster; likelihood of leak being natural gas based on ethane/methane ratio; probability the leak was detected on a given pass; and estimated distance to the leak source.

In some embodiments, an approximate flow rate of a natural gas leak Q is calculated from the integrated product of the measured methane concentration c(x) (in units of mass per volume) multiplied by the lateral wind speed $u_{lat}(x)$ perpendicular to the vehicle.

$$Q = L \int_{x_s}^{x_e} c(x) u_{lat}(x) dx \qquad (10)$$

where $x_s$ and $x_e$ are the plume start and end locations, and L is a length scale which corresponds to the anticipated vertical dispersion of the plume. L may be determined empirically from controlled release experiments, as described in US Patent Publication No. 2015/0047416 A1, published Feb. 19, 2015, entitled "Scanned 1-D Gas Plume Profile and Flux Measurements Using Multiple Analysis Measurements," which is incorporated herein by reference. In some embodiments, a lower detection limit for leak flow rate estimation may be estimated to be about 0.1 SCFH, and flow rate estimates for leaks below this level are deemed to be unreliable. Such a value may be used as a quality control threshold. Equation (10) expresses the observation that, for a given set of measured concentrations, the corresponding leak flow rate is expected to be higher if the survey vehicle passed through the plume in a direction perpendicular to the wind, since the survey sampled a relatively small extent of the plume, and lower if the survey vehicle passed through the plume along or counter to the wind, since the survey samples a larger extent of the plume.

In some embodiments, the likelihood that a leak is a natural gas leak is determined according to a determined relationship between co-measured ethane and methane levels as represented for example by an ethane/methane ratio. In some embodiments, a Picarro P3300 Surveyor gas analyzer measures methane ($CH_4$), ethane ($C_2H_6$) and water vapor ($H_2O$) concurrently. The ethane to methane concentration ratio of the gas mixture measured during a Surveyor plume detection can be used to differentiate a natural gas source from a biogenic methane source (e.g. sewer or landfill gas). Although natural gas primarily consists of methane (>90% $CH_4$) trace amounts of other gasses are also present in the supply. The existence of ethane in a Surveyor plume measurement sample is often a good indication that the gas originated from a natural gas facility, while the absence of ethane in the mixture is an indication that the source of the plume is biogenic. The methane and ethane content of a natural gas supply depends on the geologic source of the gas, and the mixture of gas from various sources. Therefore, the ethane content in the natural gas is variable and quantified in terms of the ethane to methane ratio. Regular measurements of the natural gas composition from various locations may be made and used for source attribution.

In some embodiments, multiple measurements of methane and ethane concentration during a plume detection are used to calculate the distribution of ethane/methane ratio values for each indication. The distribution of ethane/methane ratios is compared with a threshold value provided for a given location to determine if the measured plume contained natural gas, biogenic gas or a mixture of both types. The concentration ratio distribution may be used to provide a confidence interval for the reported disposition, for example, 90% confidence that a particular indication is natural gas. Indications that are determined to be biogenic gas with a predetermined confidence interval (e.g. >90%) are flagged and excluded according to the quality control procedure.

In some embodiments, indicators other than ethane may be used to determine whether a particular methane detection is due to natural gas. Such indicators may include, for example, one or more concentrations of odorants found specific to natural gas, one or more isotope ratios (e.g. 13C/12C methane, 2H/1H methane), or non-detection of traces associated with other methane sources (e.g. carbon monoxide, ethylene, acetylene, other species emitted from mobile combustion sources).

In some embodiments, a probability that a leak was detected on a given set of measurement runs is determined by the number of times an indication was generated divided by the number of opportunities there were to generate an indication. The number of opportunities to generate an indication may be calculated as the number of times the vehicle passed within a given distance (e.g. 20 meters) of the geometrical center of the aggregated leak indications.

In some embodiments, an estimated distance to a leak source may be determined using (a) spatial-scale analysis of the plume detections within a cluster, and/or more coarsely, as (b) the relative distance between indications in a cluster. Indications generated from leaks far away from the vehicle are subject to varying wind conditions that cause them to be detected broadly along the vehicle path. Indications that are detected close together are more likely attributed to a nearby source. In this case, one parameter that can be used as a proxy for distance to the leak source is the median pairwise distance of all of the leak indications in the cluster.

Since it may be difficult to isolate a single leaking component using only vehicle-based measurements, it may be advantageous to consider the characteristics of nearby gas distribution infrastructure. For example, any distribution infrastructure within a certain distance (e.g. 200 feet) of the aggregated leak indications may be considered as a potential location of the leaking source. The leak indications can then be associated with attributes including component type (e.g. transmission main, distribution main, service line, connection, valve, regulator) as well as information about the individual component (e.g. material, age, size, repair history).

In some embodiments, a determination is made whether a leak indication is in a predetermined high-consequence area (HCA). High-consequence areas are populated areas containing a critical density of buildings intended for human occupancy, buildings that would be hard to evacuate (e.g., nursing homes, hospitals, schools), or buildings and outside areas occupied by a large number of people.

In some embodiments, a leak training data set generation step 828 is performed as described below. An input to the step may include a set of known true leak grades (hazard levels) for a population of leaks. A training or validation dataset contains at least the grade and spatial location (GPS coordinate or street address) of the leak found by investigating the optimized LISA from the aggregated leak indications according to a standardized protocol. The training dataset may also contain additional information such as: above-ground/below-ground classification; underground concentration reading; distance to nearest building; distance to nearest street; ground cover presence/type (e.g. grass, concrete); and leaking component type.

In some embodiments, the leak-risk score/model determination step 830 is performed as described below. In particular, a model may be determined as the combination of the data that best characterizes the training dataset. Such a combination may be a linear and/or non-linear combination of aggregated leak indication features. In one approach, linear regression may be used to identify a suitable linear combination. In a linear regression approach, the dependent variable (hazardous or non-hazardous) is expressed as a continuous value (e.g. a number characterizing non-probabilistically a magnitude of the hazard, representing an expected impact of the hazard), which depends on a linear combination of the explanatory (input) variables. Another approach is to apply a categorical analysis to attempt to classify indications as hazardous (Grade 1 and Grade 2) or non-hazardous (Grade 3). One example of such a classification algorithm is a generalized linear model such as logistic regression. Unlike in a linear regression, in a logistic regression, the dependent variable (hazardous or non-hazardous) is categorical rather than continuous. The output is the probability of an indication being from a hazardous leak as a function of the input variables as the form:

$$P_H = \frac{1}{1 + e^{-(\beta_0 + \beta_1 x_1 + \beta_2 x_2 + \ldots + \beta_n x_n)}}$$

where $x_n$ are the explanatory variables (e.g. concentration, leak flow rate, detection probability, distance estimator) and $\beta_n$ are the coefficients that are fit to the training dataset.

If the relationship between the predicted outcome and explanatory variables is not linear, a different technique, such as random forest regression may be used to describe the data. In a random forest learning algorithm, piecewise linear functions comprise an ensemble of decision trees to describe the data, in contrast to the global polynomial regression described above.

To create either a linear or non-linear model, the inputs are the explanatory variables, $x_n$, and the true classification, $y_n$, from the training dataset. After training (machine learning), the model can predict the probability that an unknown set of samples belongs to a particular classification. A decision threshold, e.g. 0.5, is the predicted probability at which a sample will be assigned to a particular class.

Figure 31:
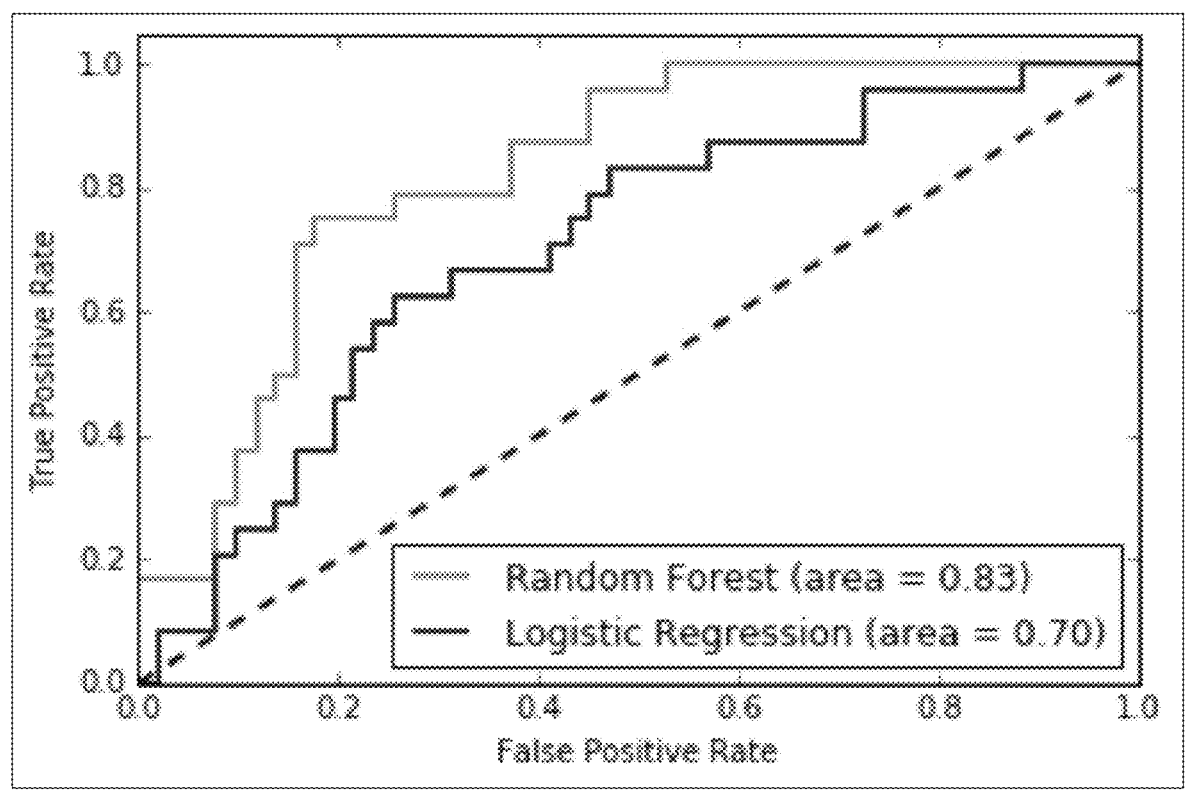
FIG. 31 shows exemplary Receiver Operator Characteristic (ROC) curves for logistic regression and random forest classification models according to some embodiments of the present invention.

The performance of a classification algorithm can be represented by the Receiver Operator Characteristic (ROC) curve. The ROC curve is a parametric curve showing the true positive rate (fraction of positive samples correctly predicted as positive) and the false positive rate (fraction of negative samples incorrectly predicted as positive, i.e. false alarm rate) as a function of decision threshold. The area under the curve is one measure of the model's performance, where an area of 1.0 is perfect classification performance and 0.5 is a random guess. FIG. 31 shows an exemplary ROC curve for logistic regression and random forest classification models as described above. In the illustrated case, the random forest model had better performance with an area of 0.83. The dashed blue line indicates a random guess.

In some embodiments, the score determination and/or reporting step 832 is performed as described below. In particular, a score may be reported as a probability that a leak indication is hazardous based on the employed risk model. Aggregated leak indications may be reported as a list ranked by risk score. An indication with $P_c > 0.5$ can be considered as "most likely hazardous" and an indication with $P_c < 0.5$ can be classified as "most likely not hazardous". Alternatively, a decision threshold or set of decision thresholds may be set based on performance requirements in terms of false positive and false negative rates. The following table is an example of a grouping of leak indications according to their risk score. In this example, the top-ranked group contains indications where the probability is greater than 90% of being a hazardous leak and the bottom-ranked group contains indications where the probability is less than 10% of being hazardous.

| Ranking Group | Decision Threshold (Pc) | True Positive Rate | False Positive Rate |
|---|---|---|---|
| 1 | 0.9 | 40% | 10% |
| 2 | 0.7 | 60% | 30% |
| 3 | 0.5 | 50% | 20% |
| 4 | 0.1 | 95% | 80% |

As Table 1 shows, setting a relatively high decision threshold leads to a low false positive rate (i.e. yield few false alarms), but may miss a higher fraction of true positives (i.e. may fail to detect some hazardous leaks). Conversely, a lower decision threshold will result in detecting a higher fraction of hazardous leaks, but may lead to a higher false alarm rate.

It will be clear to one skilled in the art that the above embodiments may be altered in many ways without departing from the scope of the invention. For example, gas leaks may include, but are not limited to: leaks from gas pipes or transportation systems (e.g., natural gas leaks), leaks from gas processing or handling facilities, and emissions from gas sources into the environment (e.g., pollution, gas emission from landfills, etc.). Gas concentration measurements are preferably performed rapidly (e.g., at a rate of 0.2 Hz or greater, more preferably 1 Hz or greater, for example 4 Hz or greater). This enables the concept of driving a vehicle at normal surface street speeds (e.g., 35 miles per hour) while accumulating useful gas concentration and wind measurement data. However, embodiments of the invention do not depend critically on the gas detection technology employed. Any gas concentration measurement technique capable of providing gas concentration measurements can be employed in some embodiments.

Although the gas concentration measurements are preferably performed while the gas measurement device is moving, at least some gas concentration measurements can be performed while the gas concentration measurement device is stationary. Such stationary gas concentration measurements may be useful for checking background gas concentrations, for example. While real-time measurements are preferred, post analysis of more sparsely sampled data, e.g., via vacuum flask sampling and later analysis via gas chromatography or other methods, may be used in some embodiments. Optionally, measurements can be made on different sides of the road or in different lanes to provide more precise localization of the leak source. Optionally, the present approaches can be used in conjunction with other conventional methods, such as visual inspection and/or measurements with handheld meters to detect emitted constituents, to further refine the results. Optionally, measurements can be made at reduced speed, or with the vehicle parked near the source, to provide additional information on location and/or source attribution.

Optionally, the system can include a source of atmospheric meteorological information, especially wind direction, but also wind speed or atmospheric stability conditions, either on-board the vehicle or at a nearby location. The stability of the atmospheric conditions can be estimated simply from the wind speed, the time of day, and the degree of cloudiness, all of which are parameters that are available either on the vehicle or from public weather databases. Optionally, the apparatus can include an on-board video camera and logging system that can be used to reject potential sources on the basis of the local imagery collected along with the gas concentration and wind data. For example, a measured emissions spike could be discounted if a vehicle powered by natural gas passed nearby during the measurements. Optionally, repeated measurements of a single location can be made to provide further confirmation (or rejection) of potential leaks.

In some embodiments, a hazard-level ranking/determination method/apparatus may employ a detection module for analyzing the data collected on the mobile platform for automatically detecting the presence of nearby gas leaks natural gas infrastructure into the atmosphere; and a ranking module that takes as input measurements from the vehicle associated with a leak, including concentration amplitude, leak emission rate, leak location, distance from vehicle, is optimized using a data set consisting of similar leaks that have been both measured by the mobile platform and graded for hazard level in-situ, and produce as output a set or subset of detected leaks that are sorted by hazard likelihood (risk) score. The mobile platform may provide a measurement of ambient wind speed relative to earth. A module may associate the gas measurements from multiple vehicle passes to a given set of potential leaks. For multiple pass measurements, quantities used by the ranking module may include: detection frequency: # detections vs # total passes by the leak; improved estimates of emission rate, amplitude, and the other single pass measurements; and variability in the estimates of emission rate, amplitude, position, and other parameters.

Accordingly, the scope of the invention should be determined by the following claims and their legal equivalents.

What is claimed is:
1. A system comprising:
    a vehicle-borne gas concentration measurement device configured to perform a sequence of geospatially-referenced mobile gas concentration measurements along one or more survey paths to collect data including gas concentration and location; and
    at least one hardware processor coupled to the gas concentration measurement device and configured to:
        automatically analyze the collected data to identify a plurality of natural gas leaks, each leak corresponding to a cluster of leak identifications in the collected data; and
        generate a list of leaks sorted by hazard level by applying a risk model to the collected data.
2. The system of claim 1, wherein analyzing the collected data comprises applying a filter to a set of leak detections to filter out a subset of leak detection, the filter including at least one filter selected from a filter based on a background level of natural gas, and a filter based on an inter-peak distance for leak detections.

3. The system of claim 1, wherein analyzing the collected data comprises spatially aggregating leak indications of the collected data into a plurality of clusters, each cluster comprising a plurality of leak indications, each cluster representing a corresponding leak.

4. The system of claim 3, wherein generating the plurality of clusters comprises performing density-based spatial clustering using a maximum distance scale and a minimum number of points per cluster as input parameters to distinguish between members and non-members of each cluster.

5. The system of claim 3, wherein generating the plurality of clusters comprises carrying out Markov clustering by performing a random walk through points representing leak indications to distinguish between members and non-members of each cluster.

6. The system of claim 3, wherein generating the plurality of clusters comprises employing wind directions values corresponding to leak indications to distinguish between members and non-members of each cluster.

7. The system of claim 1, wherein the risk model embodies training data characterizing known leaks and associated hazard levels.

8. The system of claim 1, wherein applying the risk model comprises determining values for a plurality of hazard-predictive features for a leak according to the collected data, and determining a hazard level for the leak according to the determined values.

9. The system of claim 8, wherein the plurality of hazard-predictive features includes a maximum concentration, a minimum concentration, and a representative concentration for the leak, determined from a cluster of leak indications assigned to the leak.

10. The system of claim 8, wherein the plurality of hazard-predictive features includes an estimated leak flow rate for the leak.

11. The system of claim 8, wherein the plurality of hazard-predictive features includes an estimated likelihood of the leak being a natural gas leak, the estimated likelihood determined according to a relationship between ethane and methane concentration values in the collected data.

12. The system of claim 8, wherein the plurality of hazard-predictive features includes an estimated distance between a leak indication and a corresponding leak source.

13. The system of claim 8, wherein the risk model is selected from a linear regression model yielding continuous values representing hazard levels, a logistic regression model yielding probabilities that leaks fit within predefined categories of hazard, and a random forest model.

14. The system of claim 1, wherein the hazard level for a leak represents an estimated probability that the leak fits within a predefined category of hazard.

15. A method comprising:
employing a vehicle-borne gas concentration measurement device to perform a sequence of geospatially-referenced mobile gas concentration measurements along one or more survey paths to collect data including gas concentration and location; and
employing at least one hardware processor coupled to the gas concentration measurement device to:
automatically analyze the collected data to identify a plurality of natural gas leaks, each leak corresponding to a cluster of leak identifications in the collected data; and
generate a list of leaks sorted by hazard level by applying a risk model to the collected data.

16. A non-transitory computer-readable medium encoding instructions which, when executed by a computer system comprising a hardware processor and an associated memory, cause the computer system to:
receive data collected by a vehicle-borne gas concentration measurement device performing a sequence of geospatially-referenced mobile gas concentration measurements along one or more survey paths, the collected data including gas concentration and location; and
employ at least one hardware processor coupled to the gas concentration measurement device to:
automatically analyze the collected data to identify a plurality of natural gas leaks, each leak corresponding to a cluster of leak identifications in the collected data; and
generate a list of leaks sorted by hazard level by applying a risk model to the collected data.

17. A method comprising:
collecting a set of training data for training a risk model configured to rank natural gas leaks by hazard level, the training data including a hazard level value and values of a set of hazard-predictive features for each of a plurality of natural gas leaks, the values of the set of hazard-predictive features being determined according to data collected by a vehicle-borne gas concentration measurement device performing a sequence of geospatially-referenced mobile gas concentration measurements along one or more survey paths, the collected data including gas concentration and location; and
configuring a set of parameters of the risk model according to the training data to generate predicted hazard level values for the plurality of natural gas leaks that match hazard level values in the training data.

18. The method of claim 17, wherein the plurality of hazard-predictive features for a leak includes a maximum concentration, a minimum concentration, and a representative concentration characterizing a plurality of leak indications assigned to the leak.

19. The method of claim 17, wherein the plurality of hazard-predictive features for a leak includes an estimated leak flow rate for the leak.

20. The method of claim 17, wherein the plurality of hazard-predictive features for a leak includes an estimated likelihood of the leak being a natural gas leak, the estimated likelihood determined according to a relationship between ethane and methane concentration values in the collected data.

21. The method of claim 17, wherein the plurality of hazard-predictive features for a leak includes an estimated distance between a leak indication and a corresponding leak source.

22. The method of claim 17, wherein the risk model is selected from a linear regression model yielding continuous values representing hazard levels, a logistic regression model yielding probabilities that leaks fit within predefined categories of hazard, and a random forest model.

23. The method of claim 17, wherein the hazard level for a leak represents an estimated probability that the leak fits within a predefined category of hazard.

24. A non-transitory computer-readable medium encoding instructions which, when executed by a computer system comprising a hardware processor and an associated memory, cause the computer system to:

collect a set of training data for training a risk model configured to rank natural gas leaks by hazard level, the training data including a hazard level value and values of a set of hazard-predictive features for each of a plurality of natural gas leaks, the values of the set of hazard-predictive features being determined according to data collected by a vehicle-borne gas concentration measurement device performing a sequence of geospatially-referenced mobile gas concentration measurements along one or more survey paths, the collected data including gas concentration and location; and configure a set of parameters of the risk model according to the training data to generate predicted hazard level values for the plurality of natural gas leaks that match hazard level values in the training data.

* * * * *